(12) United States Patent
Haynes et al.

(10) Patent No.: US 6,969,757 B2
(45) Date of Patent: Nov. 29, 2005

(54) DIFFERENTIAL LABELING FOR QUANTITATIVE ANALYSIS OF COMPLEX PROTEIN MIXTURES

(75) Inventors: Paul Haynes, Encinitas, CA (US); Jing Wei, San Diego, CA (US); John Yates, San Diego, CA (US); Nancy Andon, Cardiff-By-The-Sea, CA (US)

(73) Assignee: Syngenta Participations AG, Basel (CH)

( * ) Notice: Subject to any disclaimer, the term of this patent is extended or adjusted under 35 U.S.C. 154(b) by 90 days.

(21) Appl. No.: 10/057,789

(22) Filed: Jan. 25, 2002

(65) Prior Publication Data

US 2003/0082522 A1 May 1, 2003

Related U.S. Application Data

(60) Provisional application No. 60/305,232, filed on Jul. 13, 2001, and provisional application No. 60/264,576, filed on Jan. 26, 2001.

(51) Int. Cl.[7] .................. C07C 235/00; C07K 7/06; C07K 7/08; G01N 33/68
(52) U.S. Cl. .................. 530/327; 530/323; 530/345; 564/155; 564/157
(58) Field of Search .................. 530/300, 323, 530/324, 327, 328, 329, 345; 564/153, 155, 157

(56) References Cited

U.S. PATENT DOCUMENTS

| | | | |
|---|---|---|---|
| 5,130,538 A | 7/1992 | Fenn et al. | 250/282 |
| 5,470,753 A | 11/1995 | Sepetov et al. | 436/89 |
| 5,538,897 A | 7/1996 | Yates | 436/89 |
| 5,608,217 A | 3/1997 | Franzen et al. | 250/288 |
| 5,625,184 A | 4/1997 | Vestal et al. | 250/287 |
| 5,734,161 A | 3/1998 | Köster | 250/287 |
| 5,760,393 A | 6/1998 | Vestal et al. | 250/282 |
| 5,777,324 A | 7/1998 | Hillenkamp | 250/288 |
| 5,869,240 A | 2/1999 | Patterson | 435/6 |
| 6,017,693 A | 1/2000 | Yates, III et al. | 435/5 |
| 6,027,890 A | 2/2000 | Ness et al. | 435/5 |
| 6,057,543 A | 5/2000 | Vestal et al. | 250/282 |
| 6,107,623 A | 8/2000 | Bateman et al. | 250/282 |
| 6,147,344 A | 11/2000 | Annis et al. | 250/281 |
| 6,225,047 B1 | 5/2001 | Hutchens et al. | 435/5 |
| 2003/0068825 A1 * | 4/2003 | Washburn et al. | 436/86 |

FOREIGN PATENT DOCUMENTS

| | | |
|---|---|---|
| WO | WO 97/35887 | 10/1997 |
| WO | WO99/12040 | 3/1999 |
| WO | WO 00/11208 | 3/2000 |
| WO | WO 01/96539 A2 | 12/2001 |
| WO | WO 01/96539 | 12/2001 |
| WO | WO 02/059144 A2 | 8/2002 |

OTHER PUBLICATIONS

U.S. Appl. No. 60/305,169, filed Jul. 13, 2001.*
Cai et al., "Recombinant Phycobiliproteins", Analytical Biochemistry, 2001, vol. 290(2), pp 186–204.

Gygi et al., "Quantitative Analysis of Complex Protein Mixtures Using Isotope–Coded Affinity Tags", Nature Biotechnology, Oct. 1999, vol. 17, No. 10, pp 994–999.
Higashiura et al., "The Chemical Conversion of Carboxyl–Terminal Glycines in Peptides into Taurine", Journal of the Chemical Society Chemical Communications No. 9, 1989, pp 521–522.
Kapust and Waugh, "Controlled Intracellular Processing of Fusion Proteins by TEV Protease", 2000, vol. 19(2), pp 312–318.
Vingiello et al., Organic Preparations and Procedures International, 1972, pp 43–47, vol. 4, No. 1.
Boucherie et al., Two–dimensional gel protein database of *Saccharamyces cerevisiae, Electrophoresis* 17:1683–1699 (1996).
Dongr'e et al., Emerging tandem–mass–spectrometry techniques for the rapid identification of proteins, *Trends Biotechnol* 15:418–425 (1997).
Ducret et al., High throughput protein characterization by automated reverse–phase chromatography/electrospray tandem mass spectrometry, *Prot Sci* 7:706–719 (1998).
Eng et al., An approach to correlate tandem mass spectral data of peptides with amino acid sequences in a protein database, *J Am Soc Mass Spectrom* 5:976–980 (1994).
Figeys and Aebersold, High sensitivity analysis of proteins and peptides by capillary electrophoresis–tandem mass spectrometry: Recent developments in technology and applications, *Electrophoresis* 19:885–892 (1998).
Figeys et al., A microfabricated device for rapid protein identification by microelectrospray ion trap mass spectometry, *Anal Chem* 69:3153–3160 (1977).
Figeys et al., Protein identification by solid phase microextraction—capillary zone electrophoresis—microelectrospray—tandem mass spectrometry, *Nature Biotech* 14:1579–1583 (1996).
Garrels et al., Proteome studies of *Saccharomyces cerevisiae:* Identification and characterization of abundant proteins, *Electrophoresis* 18:1347–1360 (1997).
Gygi et al., Quantitative analysis of complex protein mixtures using isotope–coded affinity tags, *Nature Biotechnol* 17:994–999 (1999).
Gygi et al., Correlation between protein and mRNA abundance in yeast, *Cell Biol* 19:1720–1730 (1999).

(Continued)

Primary Examiner—Jeffrey Edwin Russel
(74) Attorney, Agent, or Firm—Jenkins, Wilson & Taylor, P.A.

(57) ABSTRACT

The present invention relates to a method of simultaneously identifying and determining the levels of expression of cysteine-containing proteins in normal and perturbed cells, a method for proteomic analysis, a process for preparing fusion proteins, and compounds of Formula II and III:

(II) Acyl-NH—X-[Epitope Tag Site]$_A$-Y-[Protease Cleavage Site]-Z-Link (III) Acyl-NH—X-alk-O-Ph-CH$_2$—Z-Link and reagents related thereto.

2 Claims, 9 Drawing Sheets

OTHER PUBLICATIONS

Gygi et al., Protein analysis by mass spectrometry and sequence database searching: Tools for cancer research in the post–genomic era, *Electrophoresis* 20:310–319 (1999).

Haynes et al., Identification of gel–separated proteins by liquid chromotography–electrospray tandem mass spectrometry: Comparison of Methods and their limitations, *Electrophoresis* 19:939–945 (1998).

Link et al., Identifying the major proteome components of *Haemophilus influenzae* type–strain NCTC 8143, *Electrophoresis* 18:1314–1334 (1997).

Link et al., Direct analysis of protein complexes using mass spectrometry, *Nat Biotech,* 17:676–682 (1999).

Mann and Wilm, Error–tolerant identification of peptides in sequence databases by peptide sequence tags, *Anal Chem* 66:4390–4399 (1994).

Opitek et al., Comprehensive on–line LC/LC/MS of proteins, *Anal Chem* 69:1518–1524 (1997).

Pennington et al., Proteome analysis: from protein characterization to biological function, *Trends Cell Bio* 7:168–173 (1997).

Shalon et al.. A DNA microarray system for analyzing complex DNA samples using two–color fluorescent probe hybridization, *Genome Res* 6:639–645 (1996).

Shevchenko et al., Mass spectrometric sequencing of proteins from silver–strained polyacrylamide gels, *Anal Chem* 68:850–858 (1996).

Shevchenko et al., Linking genome and proteome by mass spectrometry: large–scale identification of yeast proteins from two dimensional gels, *Proc Natl Acad Sci USA* 93:14440–14445 (1996).

Velculescu et al., Characterization of the Yeast Transcriptome, *Cell* 88:243–251 (1997).

Yates et al., Method to correlate tandem mass spectra of modified peptides to amino acid sequences in the protein database, *Anal Chem* 67:1426–1436 (1995).

Invitation to Pay Additional Fees for PCT/IB 03/03863, dated Apr. 7, 2004.

Wetzel et al., "A General Method for Highly Selective Cross–Linking of Unprotected Polypeptides via pH–Controlled Modification of N–Terminal α–Amino Groups," *Bioconjugate Chem.* 1(2): 114–122 (1990).

PCT Written Opinion for PCT/US02/02487 dated Sep. 8, 2004.

International Preliminary Examination Report for corresponding PCT Appl. No. PCT/IB 03/03863 dated Dec. 1, 2004.

International Preliminary Examination Report for Corresponding PCT Appl. No. PCT/IB 03/03863 dated Nov. 16, 2004.

International Preliminary Examination Report for corresponding PCT Appl. No. PCT/US02/02487 dated Jan. 28, 2005.

* cited by examiner

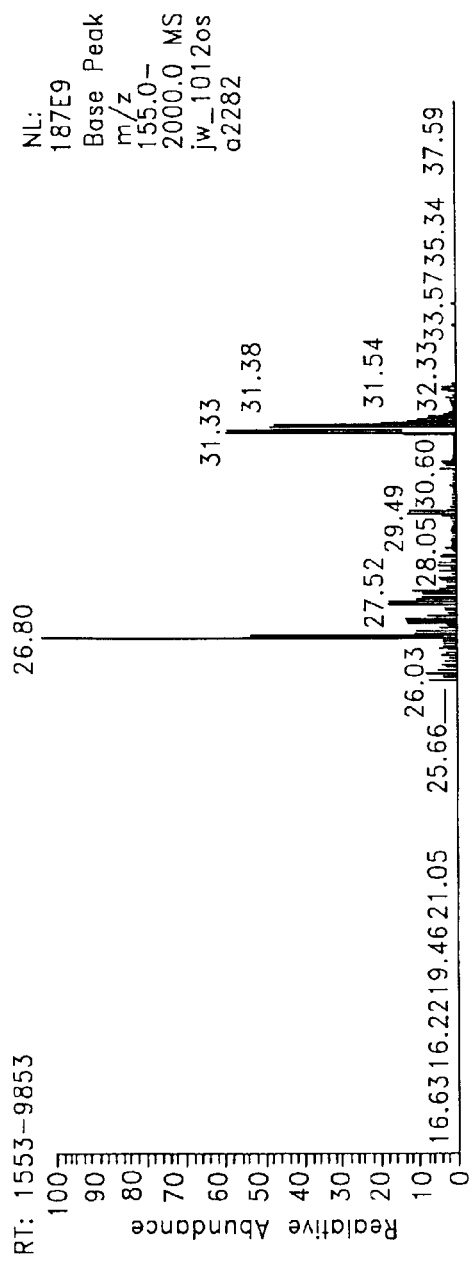
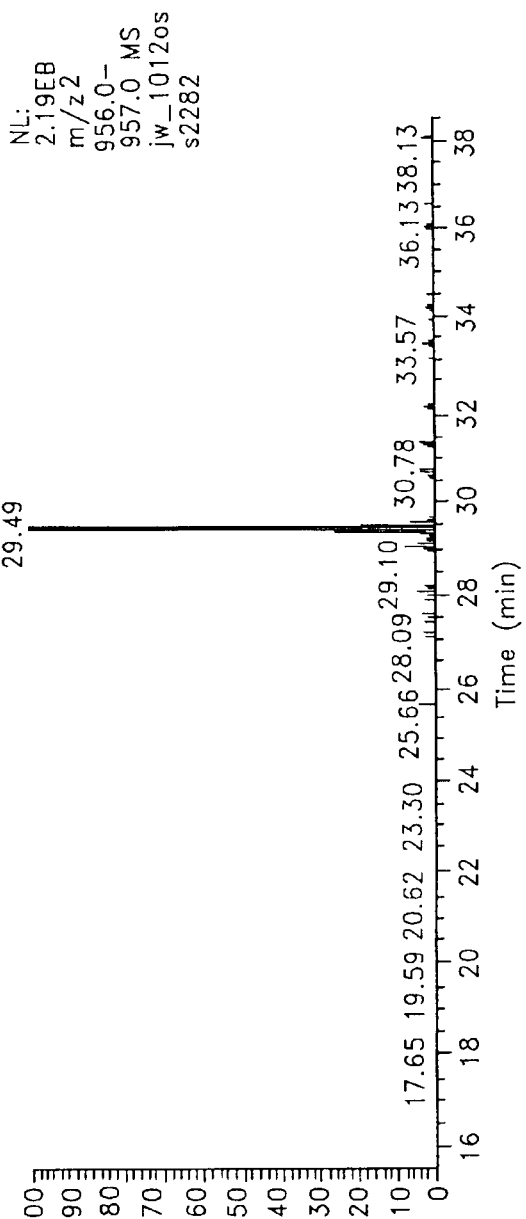
FIG. 4A
FIG. 4B

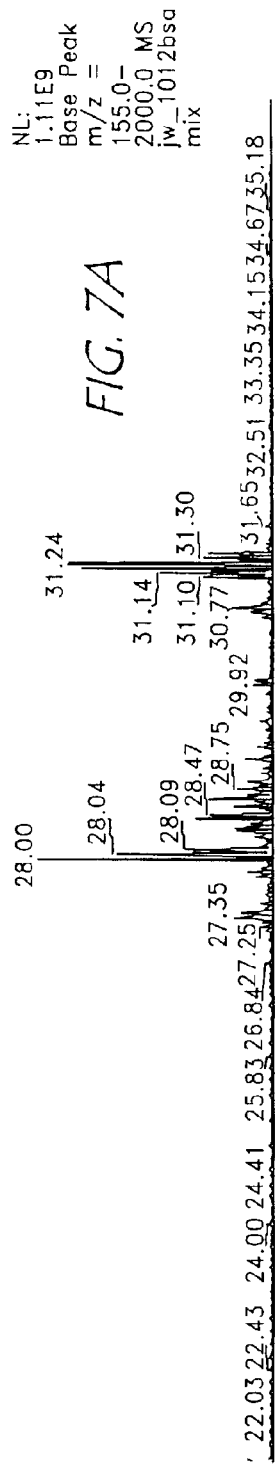
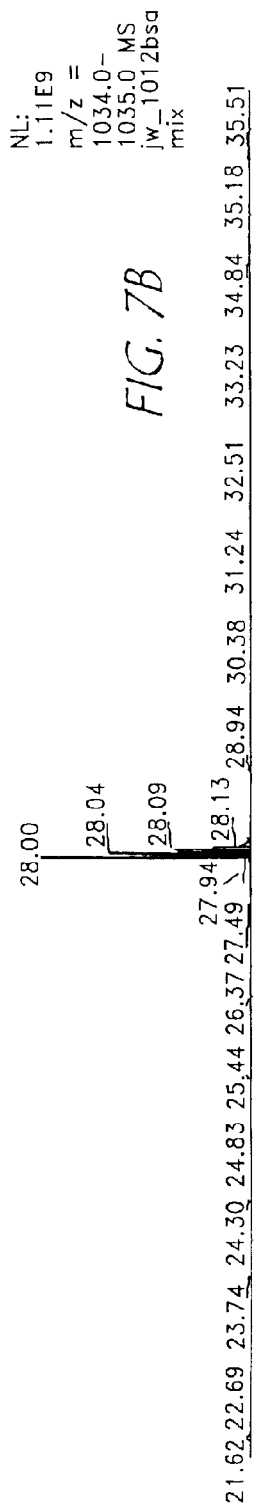
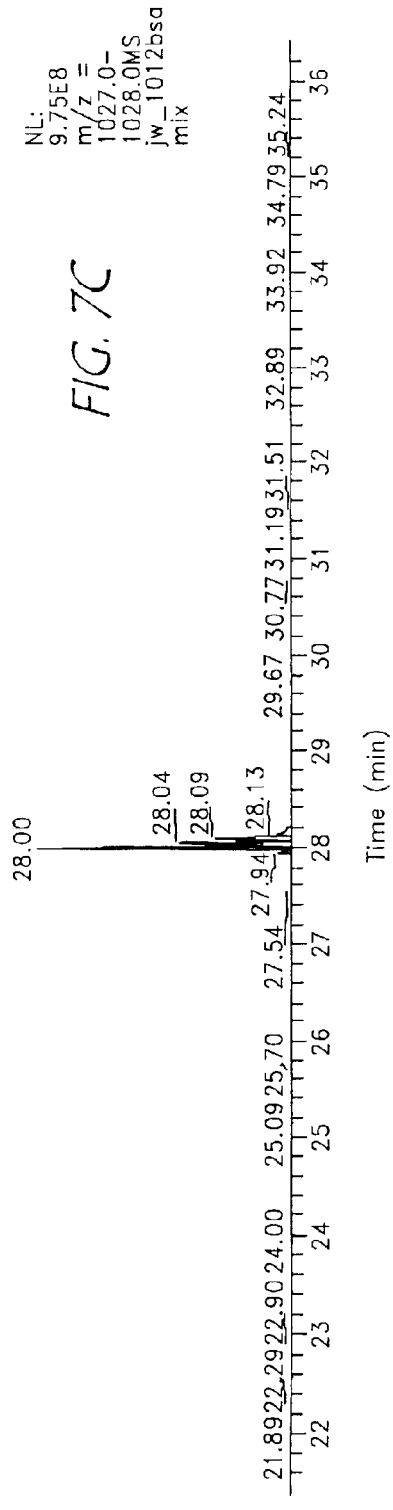
FIG. 7A
FIG. 7B
FIG. 7C

DIFFERENTIAL LABELING FOR QUANTITATIVE ANALYSIS OF COMPLEX PROTEIN MIXTURES

RELATED APPLICATIONS

The present application claims priority to the U.S. Provisional Application Ser. No. 60/305,232, filed Jul. 13, 2001, by Haynes, et al., and entitled "DIFFERENTIAL LABELING FOR QUANTITATIVE ANALYSIS OF COMPLEX PROTEIN MIXTURES", and to U.S. Provisional Application Ser. No. 60/264,576, filed Jan. 26, 2001, by Haynes, et al., entitled "DIFFERENTIAL LABELING FOR QUANTITATIVE ANALYSIS OF COMPLEX PROTEIN MIXTURES", both of which are incorporated by reference herein in their entirety including any drawings.

BACKGROUND OF THE INVENTION

Genomic technology has advanced to a point at which, in principle, it has become possible to determine complete genomic sequences and to quantitatively measure the mRNA levels for each gene expressed in a cell. For some species the complete genomic sequence has now been determined, and for one strain of the yeast *Saccharomyces cerevisiae*, the mRNA levels for each expressed gene have been precisely quantified under different growth conditions (Velculescu et al., *Cell* 88:243–251 (1997)). Comparative cDNA array analysis and related technologies have been used to determine induced changes in gene expression at the mRNA level by concurrently monitoring the expression level of a large number of genes (in some cases all the genes) expressed by the investigated cell or tissue (Shalon et al., *Genome Res* 6:639–645 (1996)). Furthermore, biological and computational techniques have been used to correlate specific function with gene sequences. The interpretation of the data obtained by these techniques in the context of the structure, control and mechanism of biological systems has been recognized as a considerable challenge. In particular, it has been extremely difficult to explain the mechanism of biological processes by genomic analysis alone.

Proteins are essential for the control and execution of virtually every biological process. The rate of synthesis and the half-life of proteins and thus their expression level are also controlled post-transcriptionally. Furthermore, the activity of proteins is frequently modulated by post-translational modifications, in particular protein phosphorylation, and dependent on the association of the protein with other molecules including DNA and proteins. Neither the level of expression nor the state of activity of proteins is therefore directly apparent from the gene sequence or even the expression level of the corresponding mRNA transcript. It is therefore essential that a complete description of a biological system include measurements that indicate the identity, quantity and the state of activity of the proteins which constitute the system. The large-scale (ultimately global) analysis of proteins expressed in a cell or tissue has been termed proteome analysis (Pennington et al., *Trends Cell Bio* 7:168–173 (1997)).

At present no protein analytical technology approaches the throughput and level of automation of genomic technology. The most common implementation of proteome analysis is based on the separation of complex protein samples most commonly by two-dimensional gel electrophoresis (2DE) and the subsequent sequential identification of the separated protein species (Ducret et al., *Prot Sci* 7:706–719 (1998); Garrels et al., *Electrophoresis* 18:1347–1360 (1997); Link et al., *Electrophoresis* 18:1314–1334 (1997); Shevchenko et al., *Proc Natl Acad Sci USA* 93:14440–14445 (1996); Gygi et al., *Electrophoresis* 20:310–319 (1999); Boucherie et al., *Electrophoresis* 17:1683–1699 (1996)). This approach has been assisted by the development of powerful mass spectrometric techniques and the development of computer algorithms which correlate protein and peptide mass spectral data with sequence databases and thus rapidly identify proteins (Eng et al., *J Am Soc Mass Spectrom* 5:976–980 (1994); Mann and Wilm, *Anal Chem* 66:4390–4399 (1994); Yates et al., *Anal Chem* 67:1426–1436 (1995)). This technology (two-dimensional mass spectrometry) has reached a level of sensitivity which now permits the identification of essentially any protein which is detectable by conventional protein staining methods including silver staining (Figeys and Aebersold, *Electrophoresis* 19:885–892 (1998); Figeys et al., *Nature Biotech* 14:1579–1583 (1996); Figeys et al., *Anal Chem* 69:3153–3160 (1997); Shevchenko et al., *Anal Chem* 68:850–858 (1996)). However, the sequential manner in which samples are processed limits the sample throughput, the most sensitive methods have been difficult to automate and low abundance proteins, such as regulatory proteins, escape detection without prior enrichment, thus effectively limiting the dynamic range of the technique. In the 2DE/(MS)$^n$ method, proteins are quantified by densitometry of stained spots in the 2DE gels.

The development of methods and instrumentation for automated, data-dependent electrospray ionization (ESI) tandem mass spectrometry (MS)$^n$ in conjunction with microcapillary liquid chromatography ($\mu$LC) and database searching has significantly increased the sensitivity and speed of the identification of gel-separated proteins. As an alternative to the 2DE/(MS)$^n$ approach to proteome analysis, the direct analysis by tandem mass spectrometry of peptide mixtures generated by the digestion of complex protein mixtures has been proposed (Dongr'e et al., *Trends Biotechnol* 15:418–425 (1997)). $\mu$LC-MS/MS has also been used successfully for the large-scale identification of individual proteins directly from mixtures without gel electrophoretic separation (Link et al., *Nat Biotech*, 17:676–682 (1999); Opitek et al., *Anal Chem* 69:1518–1524 (1997)). While these approaches accelerate protein identification, the quantities of the analyzed proteins cannot be easily determined, and these methods have not been shown to substantially alleviate the dynamic range problem also encountered by the 2DE/(MS)$^n$ approach. Therefore, low abundance proteins in complex samples are also difficult to analyze by the $\mu$LC/MS/MS method without their prior enrichment.

It is therefore apparent that current technologies, while suitable to identify a portion of the components of protein mixtures, are neither capable of measuring the quantity nor the state of activity of the protein in a mixture. Even improvements of the current approaches are unlikely to advance their performance sufficiently to make routine quantitative and functional proteome analysis a reality.

This invention provides methods and reagents that can be employed in proteome analysis which overcome the limitations inherent in traditional techniques The basic approach described can be employed for the quantitative analysis of protein expression in complex samples (such as cells, tissues, and fractions thereof), the detection and quantitation of specific proteins in complex samples, and the quantitative measurement of specific enzymatic activities in complex samples.

In this regard, a multitude of analytical techniques are presently available for clinical and diagnostic assays which detect the presence, absence, deficiency or excess of a protein or protein function associable with a normal or disease state. While these techniques are quite sensitive, they do not necessarily provide chemical separation of products and may, as a result, be difficult to use for assaying several proteins or enzymes simultaneously in a single sample. Current methods may not distinguish among aberrant expression of different enzymes or their malfunctions which lead to a common set of clinical symptoms. The methods and reagents herein can be employed in clinical and diagnostic assays for simultaneously (multiplex) monitoring of multiple proteins and protein reactions.

Complex mixtures of proteins give rise to even more complex mixtures of peptides after proteolytic digestion. One way to reduce this complexity is to label a particular amino acid and then enrich for only those peptides containing the labeled amino acid. One good example of a selective peptide label is the use of iodoacetamido functional groups to specifically react with cysteine residues. Approximately 85–90% of all proteins contain at least one cysteine residue, which makes the labeling method applicable to almost all proteins present in a complex mixture. We have designed trifunctional synthetic peptide based reagents that can be used for reducing the complexity of peptide mixtures by labeling peptides with iodoacetamido groups and then selectively enriching only those peptides containing labeled cysteine residues.

SUMMARY OF THE INVENTION

In the First Aspect, the Invention Provides a Compound of Formula I (I) Immobilization Site-Cleavage Site-Link where:
Immobilization Site is selected from the group consisting of an epitope tag, a linker to a solid surface, a metal chelating site, and a magnetic site, or a combination thereof;
Cleavage Site is selected from the group consisting of a protease cleavage site, a photocleavable linker, a restriction enzyme cleavage site, a chemical cleavage site, and a thermal cleavage site, or a combination thereof;
Link is selected from the group consisting of an amino acid reactive site and a mass variance site, or a combination thereof.

In another aspect, the invention provides a compound of Formula II or III:

(II) Acyl-NH—X-[Epitope Tag Site]$_A$-Y-[Protease Cleavage Site]-Z-Link (III) Acyl-NH—X-alk-O-Ph-CH$_2$—Z-Link where:
A is an integer from 0 to 12;
X is selected from the group consisting of an amide bond of formula —C(O)—NR—, a carbonyl of formula —C(O)—, and an amino acid sequence comprising between 0 to 50 amino acids, where R is hydrogen or lower alkyl;
Y is an amide bond of formula —C(O)—NR—, where R is hydrogen or lower alkyl, or Y is an amino acid sequence comprising between 0 to 50 amino acids;
Z is selected from the group consisting of an amide bond of formula —(CH$_2$)$_B$—C(O)—NR—, an amide bond of formula —(CH$_2$)$_B$—NR—C(O)—, and an amino acid sequence comprising between 0 to 10 amino acids, where R is hydrogen or lower alkyl, and where B is an integer from 0 to 20;
alk is straight or branched chain of alkylene comprising between 0 and 20 carbon atoms;
Ph is a phenyl group optionally substituted with one or more electron withdrawing groups ortho or para to the —CH$_2$— group;
Link is selected from the group consisting of —(CH$_2$)$_C$—I, —(CH$_2$)$_D$—CH(—(CH$_2$)$_E$CH$_3$)—(CH$_2$)$_F$—X—I, Lys-ε-iodoacetamide, Arg-δ-iodoacetamide, and Orn-δ-iodoacetamide
where C, D, E, and F are each independently an integer from 0 to 20;
Epitope Tag Site is a sequence of amino acids,
where when A is two or more, the amino acid sequence of each Epitope Tag Site can be the same or different; and
Protease Cleavage Site is a sequence of amino acids that is a cleavage site for a highly specific protease enzyme.

In another aspect, the invention provides for a method for simultaneously identifying and determining the levels of expression of cysteine-containing proteins in normal and perturbed cells, comprising:
a) preparing a first protein sample or a first peptide sample from the normal cells;
b) reacting the first protein sample or the first peptide sample with a reagent of Formula II or III:

(II) Acyl-NH—X-[Epitope Tag Site]$_A$-Y-[Protease Cleavage Site]-Z-Link (III) Acyl-NH—X-alk-O-Ph-CH$_2$—Z-Link where:
A is an integer from 0 to 12;
X is selected from the group consisting of an amide bond of formula —C(O)—NR—, a carbonyl of formula —C(O)—, and an amino acid sequence comprising between 0 to 50 amino acids, where R is hydrogen or lower alkyl;
Y is an amide bond of formula —C(O)—NR—, where R is hydrogen or lower alkyl, or Y is an amino acid sequence comprising between 0 to 50 amino acids;
Z is selected from the group consisting of an amide bond of formula —(CH$_2$)$_B$—C(O)—NR—, an amide bond of formula —(CH$_2$)$_B$—NR—C(O)—, and an amino acid sequence comprising between 0 to 10 amino acids,
where R is hydrogen or lower alkyl, and
where B is an integer from 0 to 20;
alk is straight or branched chain of alkylene comprising between 0 and 20 carbon atoms;
Ph is a phenyl group optionally substituted with one or more electron withdrawing groups ortho or para to the —CH$_2$—group;
Link is selected from the group consisting of —(CH$_2$)$_C$—I, —(CH$_2$)$_D$—CH(—(CH$_2$)$_E$CH$_3$)—(CH$_2$)$_F$—X—I, Lys-ε-iodoacetamide, Arg-δ-iodoacetamide, and Orn-δ-iodoacetamide
where C, D, E, and F are each independently an integer from 0 to 20;
Epitope Tag Site is a sequence of amino acids,
where when A is two or more, the amino acid sequence of each Epitope Tag Site can be the same or different; and
Protease Cleavage Site is a sequence of amino acids that is a cleavage site for a highly specific protease enzyme;
c) preparing a second protein sample or a second peptide sample from the perturbed cells;
d) reacting the second protein sample or the second peptide sample of step c) with a second reagent of Formula II or III:

(II) Acyl-NH—X-[Epitope Tag Site]$_A$-Y-[Protease Cleavage Site]-Z-Link (III) Acyl-NH—X-alk-O-Ph-CH$_2$—Z-Link where:
A is an integer from 0 to 12;

X is selected from the group consisting of an amide bond of formula —C(O)—NR—, a carbonyl of formula —C(O)—, and an amino acid sequence comprising between 0 to 50 amino acids, where R is hydrogen or lower alkyl;

Y is an amide bond of formula —C(O)—NR—, where R is hydrogen or lower alkyl, or Y is an amino acid sequence comprising between 0 to 50 amino acids;

Z is selected from the group consisting of an amide bond of formula —$(CH_2)_B$—C(O)—NR—, an amide bond of formula —$(CH_2)_B$—NR—C(O)—, and an amino acid sequence comprising between 0 to 10 amino acids, where R is hydrogen or lower alkyl, and where B is an integer from 0 to 20;

alk is straight or branched chain of alkylene comprising between 0 and 20 carbon atoms;

Ph is a phenyl group optionally substituted with one or more electron withdrawing groups ortho or para to the —$CH_2$— group;

Link is selected from the group consisting of —$(CH_2)_C$—I, —$(CH_2)_D$—CH(—$(CH_2)_E CH_3$)—$(CH_2)_F$—X—I, Lys-ϵ-iodoacetamide, Arg-δ-iodoacetamide, and Orn-δ-iodoacetamide where C, D, E, and F are each independently an integer from 0 to 20;

Epitope Tag Site is a sequence of amino acids, where when A is two or more, the amino acid sequence of each Epitope Tag Site can be the same or different; and Protease Cleavage Site is a sequence of amino acids that is a cleavage site for a highly specific protease enzyme, such that the molecular weight of the first reagent and the molecular weight of the second reagent are different by an integer multiple of 14 atomic mass units;

e) combining the reacted first and the second protein samples or the reacted first and the second peptide sample from steps b) and d);

f) subjecting the combined protein samples or the combined peptide samples from step e) to proteolysis at a site on the protein samples or at a site on the peptide samples, the site being other than the Protease Cleavage Site;

g) subjecting the proteolyzed combined protein samples or the proteolyzed peptide samples from step f) to an affinity chromatography system comprising a second amino acid sequence attached to a solid, thereby forming bound proteins and non-bound proteins, where the Epitope Tag Site of the reagent and the second amino acid sequence bind with high specificity to each other;

h) eluting the non-bound proteins from the affinity chromatography system;

i) subjecting the affinity chromatography system from step h) to a protease specific for the Protease Cleavage Site, thereby forming a cleaved protein mixture;

j) eluting the cleaved protein mixture from the affinity chromatography system of step i);

k) isolating the eluted protein mixture obtained from step j);

l) subjecting the eluted protein mixture from step k) to chromatographic separation, followed by mass analysis;

m) comparing the results of step 1) to:

1) determining the ratio of amounts of compounds in the two samples, where the molecular weights thereof are separated by an integer multiple of 14 atomic mass units; and 2) comparing the results obtained for each compound to protein databases containing chromatographic and molecular weight correlations.

In another aspect, the invention provides for a method for simultaneously identifying and determining the levels of expression of cysteine-containing proteins in normal and perturbed cells, comprising:

a) preparing a first protein sample or a first peptide sample from the normal cells;

b) subjecting the first protein sample or the first peptide sample from step a) to proteolysis;

c) reacting the proteolyzed first protein sample or the proteolyzed first peptide sample with a reagent of Formula II or III:

(II) Acyl-NH—X-[Epitope Tag Site]$_A$-Y-[Protease Cleavage Site]-Z-Link (III) Acyl-NH—X-alk-O-Ph-$CH_2$—Z-Link where:

A is an integer from 0 to 12;

X is selected from the group consisting of an amide bond of formula —C(O)—NR—, a carbonyl of formula —C(O)—, and an amino acid sequence comprising between 0 to 50 amino acids, where R is hydrogen or lower alkyl;

Y is an amide bond of formula —C(O)—NR—, where R is hydrogen or lower alkyl, or Y is an amino acid sequence comprising between 0 to 50 amino acids;

Z is selected from the group consisting of an amide bond of formula —$(CH_2)_B$—C(O)—NR—, an amide bond of formula —$(CH_2)_B$—NR—C(O)—, and an amino acid sequence comprising between 0 to 10 amino acids, where R is hydrogen or lower alkyl, and where B is an integer from 0 to 20;

alk is straight or branched chain of alkylene comprising between 0 and 20 carbon atoms;

Ph is a phenyl group optionally substituted with one or more electron withdrawing groups ortho or para to the —$CH_2$— group;

Link is selected from the group consisting of —$(CH_2)_C$—I, —$(CH_2)_D$—CH(—$(CH_2)_E CH_3$)—$(CH_2)_F$—X—I, Lys-ϵ-iodoacetamide, Arg-δ-iodoacetamide, and Orn-δ-iodoacetamide where C, D, E, and F are each independently an integer from 0 to 20;

Epitope Tag Site is a sequence of amino acids, where when A is two or more, the amino acid sequence of each Epitope Tag Site can be the same or different; and Protease Cleavage Site is a sequence of amino acids that is a cleavage site for a highly specific protease enzyme;

d) preparing a second protein sample or a second peptide sample from the perturbed cells;

e) subjecting the second protein sample or the second peptide sample from step d) to proteolysis;

f) reacting the proteolyzed second protein sample or the proteolyzed second peptide sample of step e) with a second reagent of Formula II or III:

(II) Acyl-NH—X-[Epitope Tag Site]$_A$-Y-[Protease Cleavage Site]-Z-Link (III) Acyl-NH—X-alk-O-Ph-$CH_2$—Z-Link where:

A is an integer from 0 to 12;

X is selected from the group consisting of an amide bond of formula —C(O)—NR—, a carbonyl of formula —C(O)—, and an amino acid sequence comprising between 0 to 50 amino acids, where R is hydrogen or lower alkyl;

Y is an amide bond of formula —C(O)—NR—, where R is hydrogen or lower alkyl, or Y is an amino acid sequence comprising between 0 to 50 amino acids;

Z is selected from the group consisting of an amide bond of formula —(CH$_2$)$_B$—C(O)—NR—, an amide bond of formula —(CH$_2$)$_B$—NR—C(O)—, and an amino acid sequence comprising between 0 to 10 amino acids,
where R is hydrogen or lower alkyl, and
where B is an integer from 0 to 20;
alk is straight or branched chain of alkylene comprising between 0 and 20 carbon atoms;
Ph is a phenyl group optionally substituted with one or more electron withdrawing groups ortho or para to the —CH$_2$— group;
Link is selected from the group consisting of —(CH$_2$)$_C$—I, —(CH$_2$)$_D$—CH(—(CH$_2$)$_E$CH$_3$)—(CH$_2$)$_F$—X—I, Lys-ε-iodoacetamide, Arg-δ-iodoacetamide, and Orn-δ-iodoacetamide
where C, D, E, and F are each independently an integer from 0 to 20;
Epitope Tag Site is a sequence of amino acids,
where when A is two or more, the amino acid sequence of each Epitope Tag Site can be the same or different; and
Protease Cleavage Site is a sequence of amino acids that is a cleavage site for a highly specific protease enzyme,
such that the molecular weight of the first reagent and the molecular weight of the second reagent are different by an integer multiple of 14 atomic mass units;
g) combining the reacted the first and the second protein samples or the reacted the first and the second peptide sample from steps c) and f);
h) subjecting the combined protein samples or the combined peptide samples from step e) to proteolysis at a site on the protein samples or at a site on the peptide samples, the site being other than the Protease Cleavage Site;
i) subjecting the proteolyzed combined protein samples or the proteolyzed peptide samples from step f) to an affinity chromatography system comprising a second amino acid sequence attached to a solid, thereby forming bound proteins and non-bound proteins,
where the Epitope Tag Site of the reagent and the second amino acid sequence bind with high specificity to each other;
j) eluting the non-bound proteins from the affinity chromatography system;
k) subjecting the affinity chromatography system from step j) to a protease specific for the Protease Cleavage Site, thereby forming a cleaved protein mixture;
l) eluting the cleaved protein mixture from the affinity chromatography system of step k);
m) isolating the eluted protein mixture obtained from step l);
n) subjecting the eluted protein mixture from step m) to chromatographic separation, followed by mass analysis;
o) comparing the results of step n) to:
  1) determining the ratio of amounts of compounds in the two samples, where the molecular weights thereof are separated by an integer multiple of 14 atomic mass units; and
  2) comparing the results obtained for each compound to protein databases containing chromatographic and molecular weight correlations.

Another aspect of the present invention relates to a method for proteomic analysis, comprising:
a) preparing a protein sample or a peptide sample from cells;
b) reacting the protein sample or the peptide sample with a reagent of the formula:

Acyl-NH—X-[Epitope Tag Site]$_A$-Y-[Protease Cleavage Site]-Z-Link where:
A is an integer from 1 to 12;
X is an amide bond of formula —C(O)—NR—, where R is hydrogen or lower alkyl, or X is an amino acid sequence comprising between 0 to 50 amino acids;
Y is an amide bond of formula —C(O)—NR—, where R is hydrogen or lower alkyl, or Y is an amino acid sequence comprising between 0 to 50 amino acids;
Z is an amide bond of formula —C(O)—NR—, where R is hydrogen or lower alkyl, or Z is an amino acid sequence comprising between 0 to 10 amino acids;
Link is selected from the group consisting of Lys-ε-iodoacetamide, Arg-δ-iodoacetamide, and Orn-δ-iodoacetamide;
Epitope Tag Site is a sequence of amino acids, and
Protease Cleavage Site is a sequence of amino acids that is a cleavage site for a highly specific protease enzyme;
c) subjecting the reacted proteins or peptides from step b) to proteolysis at a site on the protein samples or at a site on the peptide samples, the site being other than the Protease Cleavage Site;
d) subjecting the proteolyzed reacted proteins or the proteolyzed reacted peptides from step c) to an affinity chromatography system comprising a second amino acid sequence attached to a solid support, thereby forming bound proteins and non-bound proteins,
where the Epitope Tag Site of the reagent and the second amino acid sequence bind with high specificity to each other;
e) eluting the non-bound proteins from the affinity chromatography system;
f) subjecting the affinity chromatography system from step e) to a protease specific for the Protease Cleavage Site, thereby forming a cleaved protein mixture;
g) eluting the cleaved protein mixture from the affinity chromatography system of step f);
h) isolating the cleaved protein mixture obtained from step g);
i) subjecting the cleaved protein mixture from step h) to chromatographic separation, followed by mass analysis;
j) comparing the results of step i) to:
  1) determine the ratio of amounts of compounds in the sample separated by a molecular weight of 14 atomic mass units; and
  2) identify the various modified proteins by comparing the results obtained for each modified protein to protein databases containing chromatographic and molecular weight correlations.

Yet another aspect of the invention relates to a process for preparing a fusion protein of the formula:

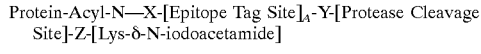
Protein-Acyl-N—X-[Epitope Tag Site]$_A$-Y-[Protease Cleavage Site]-Z-[Lys-δ-N-iodoacetamide]

comprising,
a) preparing a fusion protein sample from cells having the formula Protein-Acyl-NH—X-[Epitope Tag Site]$_A$-Y-[Protease Cleavage Site]-Z-Lys-δ-NHCOCH$_2$;
b) reacting the protein sample with an iodoacetamide, where:
A is an integer from 1 to 12;
X is an amide bond of formula —C(O)—NR—, where R is hydrogen or lower alkyl, or X is an amino acid sequence comprising between 0 to 50 amino acids;
Y is an amide bond of formula —C(O)—NR—, where R is hydrogen or lower alkyl, or Y is an amino acid sequence comprising between 0 to 50 amino acids;
Z is an amide bond of formula —C(O)—NR—, where R is hydrogen or lower alkyl, or Z is an amino acid sequence comprising between 0 to 10 amino acids;
Epitope Tag Site is a sequence of amino acids, and
Protease Cleavage Site is a sequence of amino acids that is a cleavage site for a highly specific protease enzyme.

In another aspect, the invention relates to a process for preparing a fusion protein of the formula:

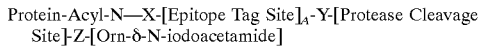
Protein-Acyl-N—X-[Epitope Tag Site]$_A$-Y-[Protease Cleavage Site]-Z-[Orn-δ-N-iodoacetamide]

comprising,
a) preparing a fusion protein sample from cells having the formula Protein-Acyl-NH—X-[Epitope Tag Site]$_A$-Y-[Protease Cleavage Site]-Z-Orn-δ-NHCOCH$_2$;
b) reacting the protein sample with an iodoacetamide, where:
A is an integer from 1 to 12;
X is an amide bond of formula —C(O)—NR—, where R is hydrogen or lower alkyl, or X is an amino acid sequence comprising between 0 to 50 amino acids;
Y is an amide bond of formula —C(O)—NR—, where R is hydrogen or lower alkyl, or Y is an amino acid sequence comprising between 0 to 50 amino acids;
Z is an amide bond of formula —C(O)—NR—, where R is hydrogen or lower alkyl, or Z is an amino acid sequence comprising between 0 to 10 amino acids;
Epitope Tag Site is a sequence of amino acids, and
Protease Cleavage Site is a sequence of amino acids that is a highly specific cleavage site for a protease enzyme.

BRIEF DESCRIPTION OF THE DRAWINGS

FIG. 3a is a printout wherein peaks are cysteinyl tryptic peptides from tagged BSA, which are captured by HA matrix and cleaved off by TEV.

FIGS. 4a,b show the μLC MS/MS analysis of PEPTag captured BSA peptides. FIG. 4a is a printout showing the base peak ion current profiles of all peptides released by TEV protease. FIG. 4b is a printout showing the reconstructed ion chromatograms from A (m/z 956.0–957.0) of the eluted peptide, which is doubly charged ion (m/z=956.4).

FIG. 5a is a printout showing the full-scan (600–1,500 m/z) mass spectrum at time 29.49 min of μLC-MS and μLC-MS/MS analysis.

FIGS. 7a–c show the μLC-MS/MS analysis of captured peptides labeled by differential PEPTags. FIG. 7a is a printout showing base peak ion current profiles of all the peptides released by TEV protease from combined two protein mixtures. FIG. 7b is a printout showing the reconstructed ion chromatograms (m/z 1034.0–1035.0) of a cysteinyl peptide labeled by PEPTag 1a FIG. 7c is a printout showing the reconstructed ion chromatograms (m/z 1027.0–1028.0) of the same cysteinyl peptide labeled by PEPTag 1b.

DETAILED DESCRIPTION OF THE PREFERRED EMBODIMENTS

Figure 1:
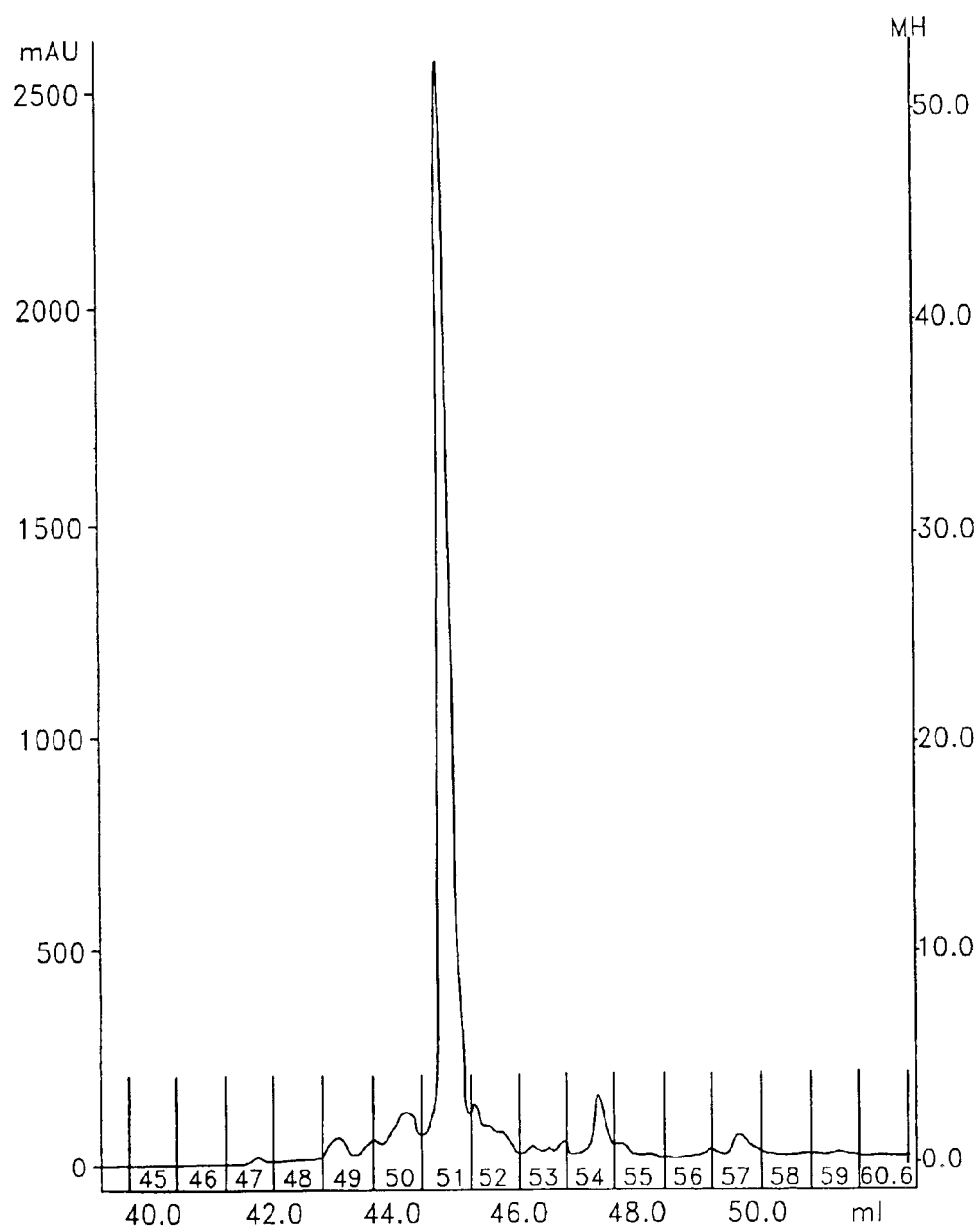
FIG. 1 is a chart showing the FPLC spectrum from the purification the synthesized PEPTag.
Figure 2A:
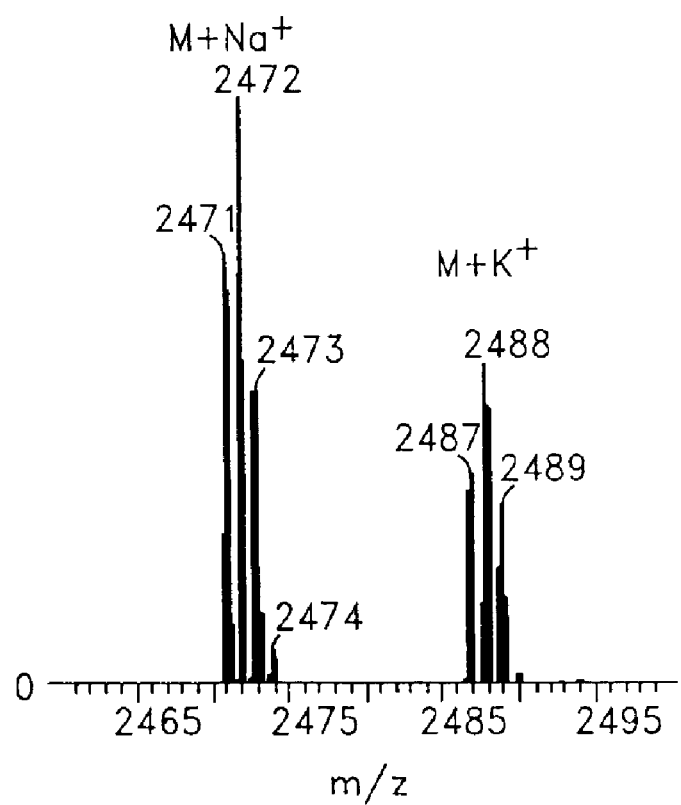
FIG. 2a is a printout showing the mass spectrum of the synthesized PEPTag.
Figure 2B:
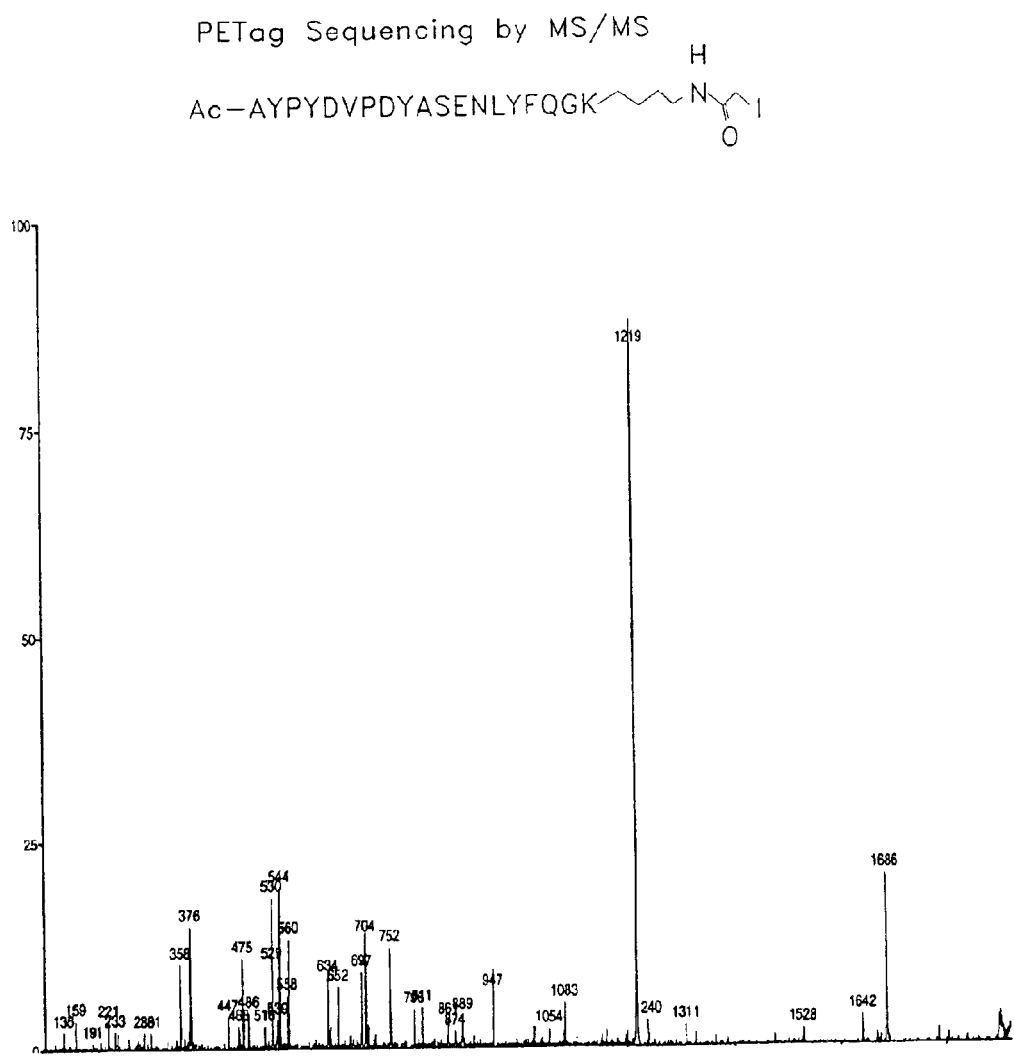
FIG. 2b is a printout showing the mass spectrum from MS/MS experiment to sequence PEPTag (SEQ ID NO.: 2).
Figures 3A, 3B:
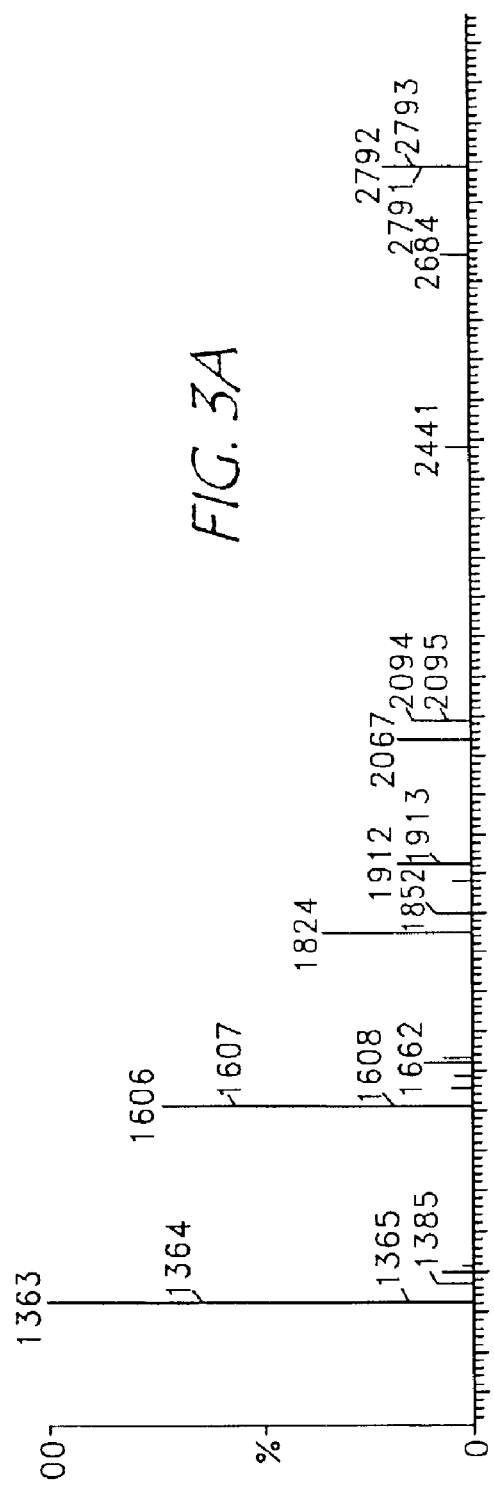
FIGS. 3a,b show printouts of the MALDI MS analysis of PEPTag captured BSA peptides.
FIG. 3b is a printout showing a control analysis of untagged BSA. The main peak in this spectrum is from TEV protease.
Figures 5A, 5B:
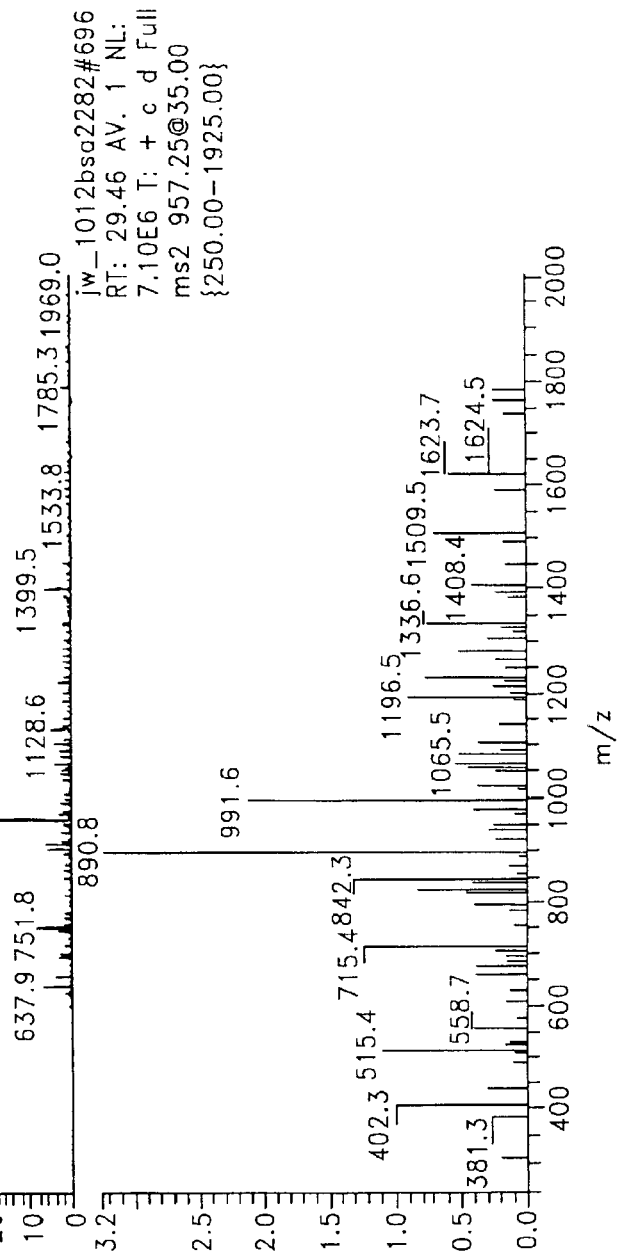
FIGS. 5a,b show the MS and MS/MS spectra of the PEPTag modified peptide.
FIG. 5b is a printout showing the tandem mass spectrum (250–1925 m/z) of the $(M+2H)^{2+}$ of the eluted peptide (m/z=957.25).

Embodiments of this invention provide analytical reagents and mass spectrometry-based methods using these reagents for the rapid and quantitative analysis of proteins or protein function in mixtures of proteins. The analytical method can be used for qualitative and particularly for quantitative analysis of global protein expression profiles in cells and tissues, i.e., the quantitative analysis of proteomes. The method can also be employed to screen for and identify proteins whose expression level in cells, tissue or biological fluids is affected by a stimulus (e.g., administration of a drug or contact with a potentially toxic material), by a change in environment (e.g., nutrient level, temperature, passage of time) or by a change in condition or cell state (e.g., disease state, malignancy, site-directed mutation, gene knockouts) of the cell, tissue or organism from which the sample originated. The proteins identified in such a screen can function as markers for the changed state. For example, comparisons of protein expression profiles of normal and malignant cells can result in the identification of proteins whose presence or absence is characteristic and diagnostic of the malignancy.

In an exemplary embodiment, the methods herein can be employed to screen for changes in the expression or state of enzymatic activity of specific proteins. These changes may be induced by a variety of chemicals, including pharmaceutical agonists or antagonists, or potentially harmful or toxic materials. The knowledge of such changes may be useful for diagnosing enzyme-based diseases and for investigating complex regulatory networks in cells.

The methods herein can also be used to implement a variety of clinical and diagnostic analyses to detect the presence, absence, deficiency or excess of a given protein or protein function in a biological fluid (e.g., blood), or in cells or tissue. The method is particularly useful in the analysis of complex mixtures of proteins, i.e., those containing 5 or more distinct proteins or protein functions.

One method employs affinity-labeled protein reactive reagents that allow for the selective isolation of peptide fragments or the products of reaction with a given protein (e.g., products of enzymatic reaction) from complex mixtures. The isolated peptide fragments or reaction products are characteristic of the presence of a protein or the presence of a protein function, e.g., an enzymatic activity, respectively, in those mixtures. Isolated peptides or reaction products are characterized by mass spectrometric (MS) techniques. In particular, the sequence of isolated peptides can be determined using tandem MS $(MS)^n$ techniques, and by application of sequence database searching techniques, the protein from which the sequenced peptide originated can be identified.

I. Reagents of the Invention

Embodiments of the present invention provide trifunctional synthetic reagents that can be used for reducing the complexity of peptide mixtures by labeling peptides at a specific amino acid residue and then selectively enriching only those peptides containing the labeled amino acid. By preparing this reagent in two forms with detectably different masses, this technique can be used to provide accurate relative quantification of peptide amounts using mass spectrometry.

The amino acids used in the reagents of the present invention may be the D isomer or the L isomer of the amino acid. Thus, the one-letter designation "A" or the three-letter designation "ala," for example, refers to both D-alanine and L-alanine. In addition, the amino acids used in the reagents of the present invention may be naturally occurring or synthetic. Thus, for example, the one-letter designation "A" or the three-letter designation "ala," refers to both the naturally occurring alanine, having the formula $^+H_3N$—CH$(CH_3)$—COO$^-$, or any chemically modified analog thereof.

In some embodiments of the invention, the peptide labeling moiety consists of a lysine residue modified with an iodoacetamide functional group on the $\epsilon$-amino group of the side chain. The synthetic peptides contain two additional motifs: a peptide epitope tag for high affinity purification; and a highly specific protease site for releasing the affinity purified labeled peptides from the affinity matrix. In addition, these synthetic peptides can readily be prepared as isoforms of two different masses by the simple expedient of using an ornithine in place of lysine to introduce a 14 mass unit difference in the carboxyl terminal acid.

In other embodiments of the invention, the peptide labeling moiety consists of a molecule modified with an iodo-containing organic substituent, which may be an iodide on a primary carbon, an acid iodide, or an iodoacetamide functional group. In addition, the peptide labeling moiety comprises a substituted benzyl moiety, which undergoes heterolytic cleavage upon exposure to light of a certain wavelength. In addition, these molecules can readily be prepared as isoforms of two different masses by the simple expedient of using an alkylene chain that has additional methylene groups or is missing methylene groups to introduce an integer multiple of 14 mass unit difference in the carboxyl terminal acid.

Thus, in a First Aspect, the Invention Provides a Compound of Formula I (I) Immobilization Site-Cleavage Site-Link where:
Immobilization Site is selected from the group consisting of an epitope tag, a linker to a solid surface, a metal chelating site, a magnetic site, and a specific oligonucleotide sequence, or a combination thereof;
Cleavage Site is selected from the group consisting of a protease cleavage site, a photocleavable linker, a restriction enzyme cleavage site, a chemical cleavage site, and a thermal cleavage site, or a combination thereof;
Link is selected from the group consisting of an amino acid reactive site and a mass variance site, or a combination thereof.

At some point during their use, the compounds of the present invention are immobilized on, for example, a surface, such that they do not move when washed with a fluid. The surface on which the compounds are immobilized may be a solid surface. Examples, without limitation of solid surfaces include beads (glass, plastic or other material), plastic, glass, silicon chip, multi-well plates, and membranes (such as PVDF or nylon).

There are a number of ways by which the compounds of the invention may be immobilized. For instance, the solid surface may comprise an amino acid sequence. The Immobilization Site of the compounds of the present invention will then comprise another amino acid sequence which is the epitope tag of the amino acid sequence on the surface. An epitope tag binds exclusively to its target amino acid sequence.

In other embodiments, the solid surface may comprise a metal chelating column, comprising for example nickel atoms. The Immobilization Site of the compounds of the invention may then comprise, for example, amino acid residues, such as histidines, or other residues, such as ethylenediaminetetraacetate, that will chelate to the metal atom on the column. The solid surface can be an oligonucleotide and the Immobilization Site can be the complimentary oligonucleotide. Those skilled in the art and familiar with metal affinity chromatography will know which chelating groups are best used with which metals on the column to be used.

In other embodiments of the present invention, the solid surface may comprise magnetic residues. In this case, the Immobilization Site of the compounds of the present invention will also comprise magnetic residues that are designed to bind magnetically to the magnetic residues of the solid surface.

In certain other embodiments, the Immobilization Site is a direct link between the solid surface and the compounds of the present invention. The direct link may be an acyl group or other chemical moieties that are capable of reacting with the solid surface, in some cases reversibly, so that the compounds of the present invention are immobilized on the surface.

The Cleavage Site is a part of the compound of the present invention that is capable of breaking the molecule in two different parts: One part of the molecule remains immobilized on the solid surface, while the other part of the molecule can move away from the solid surface by a wash fluid.

In certain embodiments, the Cleavage Site may be an amino acid sequence, comprising at least one amino acid residue, which is a cleavage site for a protease.

In other embodiments, the Cleavage Site may be a photocleavable linker. A photocleavable linker is a residue that breaks in two parts, either heterolytically or homolytically, when exposed to light of a certain wavelength, whether visible, infrared, or ultraviolet.

Other embodiments of the invention include a Cleavage Site which comprises a polynucleotide residue, of at least two nucleotides in length, that can be cleaved with restriction enzyme.

In certain other embodiments, the Cleavage Site is a site that can be chemically cleaved, for example, by addition of an acid or a base.

In other embodiments, the Cleavage Site may be cleaved thermally. This embodiment may include a Cleavage Site that comprises a polynucleotide reside that can hybridize to another polynucleotide residue connected to the Immobilization Site. Heating the compounds can then result in the hybridized polynucleotides to "melt" and separate, as a DNA double helix would.

The Link comprises a residue that can react with an amino acid. The Link may react with a side-chain of an amino acid, or with the N- or C-terminus of a polypeptide. Thus, the Link residue comprises a reactive group. The reactive group may be a moiety that can undergo nucleophilic substitution with a portion of the amino acid, or can form an amide or an ester bond with the amino acid. However, in general, the invention contemplates any reactive group that can form a bond with any part of an amino acid.

Optionally, the Link comprises a portion that allows mass variance to be introduced into a series of molecules. Thus, for example, the Link residue comprises a alkylene group, which may be a methylene in one embodiment, an ethylene in another embodiment, and a propylene in yet another embodiment, thereby introducing a mass difference of a multiple of 14 mass units between the different embodiments. The mass variance portion of the Link residue may be a series of methylene residues, or a series of —NH— residues, or a series of amide bonds, —NH—C(O)—. Any other repeating unit may work for introducing mass variance. The mass variance may be a variance that is measurable under the conditions of the experiment. Thus, mass variances in the range of 1 to 1000 mass units, or in the range of about 1 to about 500 mass units, or in the range of about 1 to about 250 mass units, or in the range of about 1 to about 100, or in the range of about 1 to about 50, or in the range of about 1 to about 30, or in the range of about 1 to about 20, or in the range of about 3 to about 20, or in the range of about 4 to about 20 are contemplated. In general, the mass variance portion of the Link affects chromatographic properties of the compound of the invention consistently.

In another aspect, the invention provides a compound of Formula II or III:

(II) Acyl-NH—X-[Epitope Tag Site]$_A$-Y-[Protease Cleavage Site]-Z-Link (III) Acyl-NH—X-alk-O-Ph-CH$_2$—Z-Link where:

A is an integer from 0 to 12;

X is selected from the group consisting of an amide bond of formula —C(O)—NR—, a carbonyl of formula —C(O)—, and an amino acid sequence comprising between 0 to 50 amino acids, where R is hydrogen or lower alkyl;

Y is an amide bond of formula —C(O)—NR—, where R is hydrogen or lower alkyl, or Y is an amino acid sequence comprising between 0 to 50 amino acids;

Z is selected from the group consisting of an amide bond of formula —(CH$_2$)$_B$—C(O)—NR—, an amide bond of formula —(CH$_2$)$_B$—NR—C(O)—, and an amino acid sequence comprising between 0 to 10 amino acids, where R is hydrogen or lower alkyl, and where B is an integer from 0 to 20;

alk is straight or branched chain of alkylene comprising between 0 and 20 carbon atoms;

Ph is a phenyl group optionally substituted with one or more electron withdrawing groups ortho or para to the —CH$_2$— group;

Link is selected from the group consisting of —(CH$_2$)$_C$—I, —(CH$_2$)$_D$—CH(—(CH$_2$)$_E$CH$_3$)—(CH$_2$)$_F$—X—I, Lys-ε-iodoacetamide, Arg-δ-iodoacetamide, and Orn-δ-iodoacetamide where C, D, E, and F are each independently an integer from 0 to 20;

Epitope Tag Site is a sequence of amino acids, where when A is two or more, the amino acid sequence of each Epitope Tag Site can be the same or different; and Protease Cleavage Site is a sequence of amino acids that is a cleavage site for a highly specific protease enzyme.

By "Acyl" it is meant a chemical substituent of the formula R—C(O)—, where R is an organic group selected from the group consisting of straight chain, branched, or cyclic alkyl, aryl, and five-membered or six-membered heteroaryl, each being optionally substituted with one or more protected substituents, which are selected from the group consisting of hydroxyl (—OH), sulfhydryl (—SH), amino (—NH$_2$), nitro (—NO$_2$), carboxyl (—COOH), ester (—COOR), and carboxamido (—CONH$_2$). These substituents may be protected by any common organic protecting group as set forth in, for example, Greene & Wutts, Protective Groups in Organic Chemistry, 3$^{rd}$ Ed., John Wiley & Sons, New York, N.Y., 1999.

Electron withdrawing groups are well-known to those of skill in the art. These groups include, without limitation, —OH, —OR, —NO$_2$, —N(CH$_3$)$_3$$^+$, —CN, —COOH, —COOR, —SO$_3$H, —CHO, and —CRO. In general, these groups are the ones that increase the rate of nucleophilic aromatic substitution when they are located at the ortho or para position with respect to the site of attack.

One of the functional groups of the compounds is the Epitope Tag Site. Suitable Epitope Tag Sites bind selectively either covalently or non-covalently and with high affinity to a capture reagent. The "capture reagent" is an amino acid sequence bound to solid support. The solid support, with the capture reagent attached thereto, are packed into a column, preferably a column for chromatography. The amino acid sequence of the capture reagent and the amino acid sequence of the Epitope Tag Site are designed to bind to each other with high selectivity and high affinity. The binding may be either covalently or non-covalently. Examples of non-covalent binding include ionic interactions, van der Waals interactions, and hydrophobic or hydrophilic interactions. The binding between the Epitope Tag Site and the capture reagent may be similar to the binding of an antibody to an epitope of a protein for which the antibody is specific.

The interaction or bond between the Epitope Tag Site and the capture agent preferably remains intact after extensive and multiple washings with a variety of solutions to remove non-specifically bound components. The Epitope Tag Site binds minimally or preferably not at all to components in the assay system, except the capture agent, and does not significantly bind to surfaces of reaction vessels. Any non-specific interaction of the Epitope Tag Site with other components or surfaces should be disrupted by multiple washes that leave Epitope Tag Site-capture agent interaction intact. Further, the interaction of Epitope Tag Site and the capture agent can be disrupted to release peptide, substrates or reaction products, for example, by addition of a displacing ligand or by changing the temperature or solvent conditions. Preferably, neither capture agent nor Epitope Tag Site react chemically with other components in the assay system and both groups should be chemically stable over the time period of an assay or experiment.

The Epitope Tag Site is preferably soluble in the sample liquid to be analyzed and the capture reagent should remain soluble in the sample liquid even though attached to an insoluble resin such as Agarose. In the case of the capture reagent, the term "soluble" means that the capture reagent is sufficiently hydrated or otherwise solvated such that it functions properly for binding to the Epitope Tag Site. The capture reagent or capture reagent-containing conjugates should not be present in the sample to be analyzed, except when added to capture the Epitope Tag Site.

A displacement ligand is optionally used to displace the Epitope Tag Site from the capture reagent. Suitable displacement ligands are not typically present in samples unless added. The displacement ligand should be chemically and enzymatically stable in the sample to be analyzed and should not react with or bind to components (other than the capture reagent) in samples or bind non-specifically to reaction vessel walls. The displacement ligand preferably does not undergo peptide-like fragmentation during mass spectral analysis, and its presence in sample should not significantly suppress the ionization of tagged peptide, substrate or reaction product conjugates.

Another functional group of the compounds disclosed herein is the Protease Cleavage Site. This site is an amino acid sequence, which in some embodiments comprises between 1 and 15 amino acids, and in other embodiments comprises between 4 and 8 amino acids, while in certain other embodiments comprises at least four amino acids. In one embodiment, the Protease Cleavage Site is an amino acid sequence of formula ENLYFQG (SEQ ID NO: 1).

The Protease Cleavage Site is designed to be cleaved once it is exposed to a highly specific protease enzyme. In certain embodiments, the protease enzyme is selected from the group consisting of TEV protease, chymotrypsin, endoproteinase Arg-C, endoproteinase Asp-N, trypsin, *Staphylococcus aureus* protease, thermolysin, and pepsin. In other embodiments, the protease enzyme is TEV protease. Preferably, the Protease Cleavage Site is not cleaved by the enzyme for the initial proteolysis of the lysed cell sample, nor would the cleavage site be lysed by any contaminating proteases from the cell sample.

The third functional group of the compounds disclosed herein is the protein reactive group, designated as "Link" in the above formula. This group may selectively react with certain protein functional groups or may be a substrate of an enzyme of interest. Any selectively reactive protein reactive group should react with a functional group of interest that is present in at least a portion of the proteins in a sample. Reaction of Link with functional groups on the protein should occur under conditions that do not lead to substantial degradation of the compounds in the sample to be analyzed. Examples of selectively reactive Links suitable for use in the affinity tagged reagents include those which react with sulfhydryl groups to tag proteins containing cysteine, those that react with amino groups, carboxylate groups, ester groups, phosphate reactive groups, and aldehyde and/or ketone reactive groups or, after fragmentation with CNBr, with homoserine lactone.

Thiol reactive groups include epoxides, α-haloacyl groups, nitrites, sulfonated alkyls or aryl thiols and maleimides. Amino reactive groups tag amino groups in proteins and include sulfonyl halides, isocyanates, isothiocyantes, active esters, including tetrafluorophenyl esters, and N-hydroxysuccinimidyl esters, acid halides, and acid anyhydrides. In addition, amino reactive groups include aldehydes or ketones in the presence or absence of $NaBH_4$ or $NaCNBH_3$.

Carboxylic acid reactive groups include amines or alcohols in the presence of a coupling agent such as dicyclohexylcarbodiimide, or 2,3,5,6-tetrafluorophenyl trifluoroacetate and in the presence or absence of a coupling catalyst such as 4dimethylaminopyridine; and transition metal-diamine complexes including Cu(II)phenanthroline.

Ester reactive groups include amines which, for example, react with homoserine lactone.

Phosphate reactive groups include chelated metal where the metal is, for example Fe(III) or Ga(III), chelated to, for example, nitrilotriacetiac acid or iminodiacetic acid.

Aldehyde or ketone reactive groups include amine plus $NaBH_4$ or $NaCNBH_3$, or these reagents after first treating a carbohydrate with periodate to generate an aldehyde or ketone.

The Link group should be soluble in the sample liquid to be analyzed and it should be stable with respect to chemical reaction, e.g., substantially chemically inert, with components of the sample as well as the Epitope Tag Site, Protease Cleavage Site, and the capture reagent groups. The Link group when bound to the molecule should not interfere with the specific interaction of the Epitope Tag Site with the capture reagent or interfere with the displacement of the Epitope Tag Site from the capture reagent by a displacing ligand or by a change in temperature or solvent. The Link group should bind minimally or preferably not at all to other components in the system, to reaction vessel surfaces or to the capture reagent. Any non-specific interactions of the Link group should be broken after multiple washes which leave the Epitope Tag Site-capture reagent complex intact.

The Link group may be selected from a group of substituents that differ from one another by the presence or absence of one or more repeating units, such as methylene ($—CH_2—$) groups. Thus, groups that contain straight chain alkylene moieties within them are particularly well-suited for this purpose.

In certain embodiments, the invention contemplates using lysine, ornithine, or arginine, coupled with iodoacetamide, as the Link group. "Orn" is the three letter designation for "L-ornithine," which is (S)—(+)-2,5-diaminopentanoic acid, $H_2N(CH_2)_3CH(NH_2)COOH$. "Iodoacetamide" is an organic substituent group with the structure $I—CH_2—C(O)—NH—$. When an amino acid group of a compound is derivatized by the iodoacetamide group, the iodoacetamide group is chemically bound to the side-chain amino group of the amino acid moiety. Thus, the designation "ε" or "δ" following the amino acids in the above formula designate the position at which the amino acid is derivatized by the iodoacetamide group. For example, Lys-ε-iodoacetamide has the formula

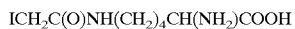

It is also understood within the context of the invention that the incorporation of the designation "ε" or "δ" is optional. Therefore, Lys-ε-iodoacetamide and Lys-iodoacetamide (K-iodoacetamide), Arg-δ-iodoacetamide and Arg-iodoacetamide (R-iodoacetamide), and Orn-δ-iodoacetamide and Orn-iodoacetamide refer to the same compound or moiety, respectively.

Specific embodiments provided herein include, but are in no way limited to, the following compounds:

Acyl-NH-AYPYDVPDYASENLYFQGK-iodoacetamide (SEQ ID NO: 2),
Acyl-NH-AYPYDVPDYASENLYFQGGK-iodoacetamide (SEQ ID NO: 3),
Acyl-NH-AYPYDVPDYASENLYFQGAK-iodoacetamide (SEQ ED NO: 4),
Acyl-NH-AYPYDVPDYASENLYFQG(GABA)K-iodoacetamide (SEQ ID NO: 5),
Acyl-NH-AYPYDVPDYASENLYFQGVK-iodoacetamide (SEQ ID NO: 6),
Acyl-NH-AYPYDVPDYASENLYFQGOrn-iodoacetamide (SEQ ID NO: 7),
Acyl-NH-AYPYDVPDYASENLYFQGGOrn-iodoacetamide (SEQ ID NO: 8),
Acyl-NH-AYPYDVPDYASENLYFQGAOrn-iodoacetamide (SEQ ID NO: 9),
Acyl-NH-AYPYDVPDYASENLYFQG(GABA)Orn-iodoacetamide (SEQ ID NO: 10),
Acyl-NH-AYPYDVPDYASENLYFQGVOrn-iodoacetamide (SEQ ID NO: 11),
Acyl-NH-AYPYDVPDYASENLYFQGR-iodoacetamide (SEQ ID NO: 12),
Acyl-NH-AYPYDVPDYASENLYFQGGR-iodoacetamide (SEQ ID NO: 13),
Acyl-NH-AYPYDVPDYASENLYFQGAR-iodoacetamide (SEQ ID NO: 14),
Acyl-NH-AYPYDVPDYASENLYFQG(GABA)R-iodoacetamide (SEQ ID NO: 15), and
Acyl-NH-AYPYDVPDYASENLYFQGVR-iodoacetamide (SEQ ID NO: 16).

Other specific embodiments include:
Acyl-NH-CASENLYFQGK-$CH_2CH_2CH_2CH_2$—NH—C(O)—$CH_2I$ (SEQ ID NO: 41),
Acyl-NH-CASENLYFQGOrn-$CH_2CH_2CH_2$—NH—C(O)—$CH_2I$ (SEQ ID NO: 42), Acyl-NH-CASENLYFQGPK-CH₂CH₂CH₂CH₂—NH—C(O)CH₂I (SEQ ID NO: 43), and Acyl-NH-CASENLYFQGPOrn-CH₂CH₂CH₂CH₂—NH—C(O)—CH₂I (SEQ ID NO: 44).

Other embodiments of the invention include compounds in which the Link moiety is a non-amino acid organic group. In these embodiments, the Link moiety is —(CH₂)$_C$—I or —(CH₂)$_D$—CH(—(CH₂)$_E$CH₃)—(CH₂)$_F$—X—I, where C, D, E, and F are each independently an integer from 0 to 20, and X is as defined herein. In some embodiments, the Link group is iodoacetamide. In other embodiments, the Link group is selected from the group consisting of —CH(CH₂C(O)I)CH₂CH₃, —C(C(O)I)CH₂CH₂CH₃, —CH(CH₂I)CH₂CH₃, —CH₂CH(CH₂I)CH₂CH₂CH₃.

In other embodiments, the invention relates to a compound of Formula Ill. In some embodiments, alk is a straight or branched chain of alkylene comprising between 0 and 20, between 0 and 15, between 0 and 10, between 0 and 5, or between 0 and 3 carbon atoms carbon atoms. In some embodiments alk is a straight chain of alkylene. alk may be selected from the group consisting of methylene, ethylene, propylene, n-butylene, and n-pentylene. In certain embodiments, alk is propylene.

In some embodiments Ph is a substituted phenyl group. It may be substituted with electron withdrawing groups. The substitutions may take place at positions ortho or para to the methylene group to which Ph is connected. In certain embodiments, the substituents on Ph are methoxy or nitro. In some embodiments, Ph is the following:

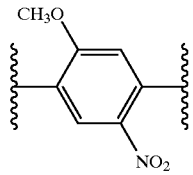

The Ph groups is such that when the molecule is exposed to a light of certain wavelength, for example ultraviolet light, the bond between the CH₂ group and Z undergoes heterolytic cleavage. Therefore, the substituents on Ph are situated to stabilize the resulting benzylic free radical.

In embodiments, Z is an amino acid sequence comprising between 1 and 3 amino acids. In certain embodiments, Z is a single amino acid. It may be any of the natural or synthetic amino acids known in the art. In some embodiments, Z is selected from the group consisting of glycine, alanine, and valine. In certain other embodiments, Z may be a synthetic amino acid, where the amino group in a position other than α to the carboxyl group. For instance, the amino group may be β, δ, ε, φ, or γ, or any other position, to the carboxyl group. In some embodiments Z is γ-aminobutyric acid.

Certain other specific embodiments of the invention include, without limitation, Acyl-CH₂CH₂CH₂—O-Ph-CH₂—G—NH—C(O)—CH₂I, Acyl-CH₂CH₂CH₂—O-Ph-CH₂—A—NH—C(O)—CH₂I, Acyl-CH₂CH₂CH₂—O-Ph-CH₂-γ-aminobutyric acid-NH—C(O)—CH₂I, and Acyl-CH₂CH₂CH₂—O-Ph-CH₂—V—NH—C(O)—CH₂I,

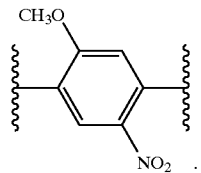

where Ph is

II. Determination of Levels of Expression

In another aspect, the invention provides for a method for simultaneously identifying and determining the levels of expression of cysteine-containing proteins in normal and perturbed cells, comprising:

a) preparing a first protein sample or a first peptide sample from the normal cells;

b) reacting the first protein sample or the first peptide sample with a reagent of Formula II or III:

(II) Acyl-NH—X-[Epitope Tag Site]$_A$-Y-[Protease Cleavage Site]-Z-Link (III) Acyl-NH—X-alk-O-Ph-CH₂—Z-Link where:

A is an integer from 0 to 12;

X is selected from the group consisting of an amide bond of formula —C(O)—NR—, a carbonyl of formula —C(O)—, and an amino acid sequence comprising between 0 to 50 amino acids, where R is hydrogen or lower alkyl;

Y is an amide bond of formula —C(O)—NR—, where R is hydrogen or lower alkyl, or Y is an amino acid sequence comprising between 0 to 50 amino acids;

Z is selected from the group consisting of an amide bond of formula —(CH₂)$_B$—C(O)—NR—, an amide bond of formula —(CH₂)$_B$—NR—C(O)—, and an amino acid sequence comprising between 0 to 10 amino acids, where R is hydrogen or lower alkyl, and where B is an integer from 0 to 20;

alk is straight or branched chain of alkylene comprising between 0 and 20 carbon atoms;

Ph is a phenyl group optionally substituted with one or more electron withdrawing groups ortho or para to the —CH₂— group;

Link is selected from the group consisting of —(CH₂)$_C$—I, —(CH₂)$_D$—CH(—(CH₂)$_E$CH₃)—(CH₂)$_F$—X—I, Lys-ε-iodoacetamide, Arg-δ-iodoacetamide, and Orn-δ-iodoacetamide where C, D, E, and F are each independently an integer from 0 to 20;

Epitope Tag Site is a sequence of amino acids, where when A is two or more, the amino acid sequence of each Epitope Tag Site can be the same or different; and Protease Cleavage Site is a sequence of amino acids that is a cleavage site for a highly specific protease enzyme;

c) preparing a second protein sample or a second peptide sample from the perturbed cells;

d) reacting the second protein sample or the second peptide sample of step c) with a second reagent of Formula II or III:

(II) Acyl-NH—X-[Epitope Tag Site]$_A$-Y-[Protease Cleavage Site]-Z-Link (III) Acyl-NH—X-alk-O-Ph-CH₂—Z-Link where:

A is an integer from 0 to 12;

X is selected from the group consisting of an amide bond of formula —C(O)—NR—, a carbonyl of formula —C(O)—, and an amino acid sequence comprising between 0 to 50 amino acids, where R is hydrogen or lower alkyl;

Y is an amide bond of formula —C(O)—NR—, where R is hydrogen or lower alkyl, or Y is an amino acid sequence comprising between 0 to 50 amino acids;

Z is selected from the group consisting of an amide bond of formula —(CH$_2$)$_B$—C(O)—NR—, an amide bond of formula —(CH$_2$)$_B$—NR—C(O)—, and an amino acid sequence comprising between 0 to 10 amino acids, where R is hydrogen or lower alkyl, and where B is an integer from 0 to 20;

alk is straight or branched chain of alkylene comprising between 0 and 20 carbon atoms;

Ph is a phenyl group optionally substituted with one or more electron withdrawing groups ortho or para to the —CH$_2$— group;

Link is selected from the group consisting of —(CH$_2$)$_C$—I, —(CH$_2$)$_D$—CH(—(CH$_2$)$_E$CH$_3$)—(CH$_2$)$_F$—X—I, Lys-ε-iodoacetamide, Arg-δ-iodoacetamide, and Orn-δ-iodoacetamide where C, D, E, and F are each independently an integer from 0 to 20;

Epitope Tag Site is a sequence of amino acids, where when A is two or more, the amino acid sequence of each Epitope Tag Site can be the same or different; and Protease Cleavage Site is a sequence of amino acids that is a cleavage site for a highly specific protease enzyme, such that the molecular weight of the first reagent and the molecular weight of the second reagent are different by an integer multiple of 14 atomic mass units;

e) combining the reacted first and the second protein samples or the reacted first and the second peptide sample from steps b) and d);

f) subjecting the combined protein samples or the combined peptide samples from step e) to proteolysis at a site on the protein samples or at a site on the peptide samples, the site being other than the Protease Cleavage Site;

g) subjecting the proteolyzed combined protein samples or the proteolyzed peptide samples from step f) to an affinity chromatography system comprising a second amino acid sequence attached to a solid, thereby forming bound proteins and non-bound proteins, where the Epitope Tag Site of the reagent and the second amino acid sequence bind with high specificity to each other;

h) eluting the non-bound proteins from the affinity chromatography system;

i) subjecting the affinity chromatography system from step h) to a protease specific for the Protease Cleavage Site, thereby forming a cleaved protein mixture;

j) eluting the cleaved protein mixture from the affinity chromatography system of step i);

k) isolating the eluted protein mixture obtained from step j);

l) subjecting the eluted protein mixture from step k) to chromatographic separation, followed by mass analysis;

m) comparing the results of step l) to:
  1) determining the ratio of amounts of compounds in the two samples, where the molecular weights thereof are separated by an integer multiple of 14 atomic mass units; and
  2) comparing the results obtained for each compound to protein databases containing chromatographic and molecular weight correlations.

In another aspect, the invention provides for a method for simultaneously identifying and determining the levels of expression of cysteine-containing proteins in normal and perturbed cells, comprising:

a) preparing a first protein sample or a first peptide sample from the normal cells;

b) subjecting the first protein sample or the first peptide sample from step a) to proteolysis;

c) reacting the proteolyzed first protein sample or the proteolyzed first peptide sample with a reagent of Formula II or III:

(II) Acyl-NH—X-[Epitope Tag Site]$_A$-Y-[Protease Cleavage Site]-Z-Link (III) Acyl-NH—X-alk-O-Ph-CH$_2$—Z-Link where:

A is an integer from 0 to 12;

X is selected from the group consisting of an amide bond of formula —C(O)—NR—, a carbonyl of formula —C(O)—, and an amino acid sequence comprising between 0 to 50 amino acids, where R is hydrogen or lower alkyl;

Y is an amide bond of formula —C(O)—NR—, where R is hydrogen or lower alkyl, or Y is an amino acid sequence comprising between 0 to 50 amino acids;

Z is selected from the group consisting of an amide bond of formula —(CH$_2$)$_B$—C(O)—NR—, an amide bond of formula —(CH$_2$)$_B$—NR—C(O)—, and an amino acid sequence comprising between 0 to 10 amino acids, where R is hydrogen or lower alkyl, and where B is an integer from 0 to 20;

alk is straight or branched chain of alkylene comprising between 0 and 20 carbon atoms;

Ph is a phenyl group optionally substituted with one or more electron withdrawing groups ortho or para to the —CH$_2$— group;

Link is selected from the group consisting of —(CH$_2$)$_C$—I, —(CH$_2$)$_D$—CH(—(CH$_2$)$_E$CH$_3$)—(CH$_2$)$_F$—X—I, Lys-ε-iodoacetamide, Arg-δ-iodoacetamide, and Orn-δ-iodoacetamide where C, D, E, and F are each independently an integer from 0 to 20;

Epitope Tag Site is a sequence of amino acids, where when A is two or more, the amino acid sequence of each Epitope Tag Site can be the same or different; and Protease Cleavage Site is a sequence of amino acids that is a cleavage site for a highly specific protease enzyme;

d) preparing a second protein sample or a second peptide sample from the perturbed cells;

e) subjecting the second protein sample or the second peptide sample from step d) to proteolysis;

f) reacting the proteolyzed second protein sample or the proteolyzed second peptide sample of step e) with a second reagent of Formula II or III:

(II) Acyl-NH—X-[Epitope Tag Site]$_A$-Y-[Protease Cleavage Site]-Z-Link (III) Acyl-NH—X-alk-O-Ph-CH$_2$—Z-Link where:

A is an integer from 0 to 12;

X is selected from the group consisting of an amide bond of formula —C(O)—NR—, a carbonyl of formula —C(O)—, and an amino acid sequence comprising between 0 to 50 amino acids, where R is hydrogen or lower alkyl;

Y is an amide bond of formula —C(O)—NR—, where R is hydrogen or lower alkyl, or Y is an amino acid sequence comprising between 0 to 50 amino acids;

Z is selected from the group consisting of an amide bond of formula —(CH$_2$)$_B$—C(O)—NR—, an amide bond of formula —(CH$_2$)$_B$—NR—C(O)—, and an amino acid sequence comprising between 0 to 10 amino acids,
where R is hydrogen or lower alkyl, and
where B is an integer from 0 to 20;
alk is straight or branched chain of alkylene comprising between 0 and 20 carbon atoms;
Ph is a phenyl group optionally substituted with one or more electron withdrawing groups ortho or para to the —CH2— group;
Link is selected from the group consisting of —(CH$_2$)$_C$—I, —(CH$_2$)$_D$—CH(—(CH$_2$)$_E$CH$_3$)—(CH$_2$)$_F$—X—I, Lys-ε-iodoacetamide, Arg-δ-iodoacetamide, and Orn-δ-iodoacetamide
where C, D, E, and F are each independently an integer from 0 to 20;
Epitope Tag Site is a sequence of amino acids,
where when A is two or more, the amino acid sequence of each Epitope Tag Site can be the same or different; and
Protease Cleavage Site is a sequence of amino acids that is a cleavage site for a highly specific protease enzyme,
such that the molecular weight of the first reagent and the molecular weight of the second reagent are different by an integer multiple of 14 atomic mass units;
g) combining the reacted the first and the second protein samples or the reacted the first and the second peptide sample from steps c) and f);
h) subjecting the combined protein samples or the combined peptide samples from step e) to proteolysis at a site on the protein samples or at a site on the peptide samples, the site being other than the Protease Cleavage Site;
i) subjecting the proteolyzed combined protein samples or the proteolyzed peptide samples from step f) to an affinity chromatography system comprising a second amino acid sequence attached to a solid, thereby forming bound proteins and non-bound proteins,
where the Epitope Tag Site of the reagent and the second amino acid sequence bind with high specificity to each other;
j) eluting the non-bound proteins from the affinity chromatography system;
k) subjecting the affinity chromatography system from step j) to a protease specific for the Protease Cleavage Site, thereby forming a cleaved protein mixture;
l) eluting the cleaved protein mixture from the affinity chromatography system of step k);
m) isolating the eluted protein mixture obtained from step l);
n) subjecting the eluted protein mixture from step m) to chromatographic separation, followed by mass analysis;
o) comparing the results of step n) to:
  1) determining the ratio of amounts of compounds in the two samples, where the molecular weights thereof are separated by an integer multiple of 14 atomic mass units; and
  2) comparing the results obtained for each compound to protein databases containing chromatographic and molecular weight correlations.

In certain embodiments, if in step c) in the above method Link is Lys-ε-iodoacetamide, then in step f) Link is Orn-δ-iodoacetamide. Alternatively, if in step c) Link is Orn-δ-iodoacetamide, then in step f) Link is Lys-ε-iodoacetamide. In another embodiment, the Z substituent in the first reagent, i.e., in step c) has a molecular weight that is an integer multiple of 14 atomic mass units different than the Z substituent in the second reagent, i.e., in step f). For example, and without limitation, the Z in the first reagent contains valine whereas the Z in the second reagent contains leucine instead of valine, all the other amino acids in Z, if any, remaining the same between the two reagents.

In an embodiment, the reagent of step c) is selected from the group consisting of
Acyl-NH-AYPYDVPDYASENLYFQGK-iodoacetamide (SEQ ID NO: 17),
Acyl-NH-AYPYDVPDYASENLYFQGGK-iodoacetamide (SEQ ID NO: 18),
Acyl-NH-AYPYDVPDYASENLYFQGAK-iodoacetamide (SEQ ID NO: 19),
Acyl-NH-AYPYDVPDYASENLYFQG(GABA)K-iodoacetamide (SEQ ID NO: 20),
Acyl-NH-AYPYDVPDYASENLYFQGVK-iodoacetamide (SEQ ID NO: 21),
Acyl-NH-AYPYDVPDYASENLYFQGR-iodoacetamide (SEQ ID NO: 22),
Acyl-NH-AYPYDVPDYASENLYFQGGR-iodoacetamide (SEQ ID NO: 23),
Acyl-NH-AYPYDVPDYASENLYFQGAR-iodoacetamide (SEQ ID NO: 24),
Acyl-NH-AYPYDVPDYASENLYFQG(GABA)R-iodoacetamide (SEQ ID NO: 25),
Acyl-NH-AYPYDVPDYASENLYFQGVR-iodoacetamide (SEQ ID NO: 26),
Acyl-NH-AYPYDVPDYASENLYFQGOrn-iodoacetamide (SEQ ID NO: 27),
Acyl-NH-AYPYDVPDYASENLYFQGGOrn-iodoacetamide (SEQ ID NO: 28),
Acyl-NH-AYPYDVPDYASENLYFQGAOrn-iodoacetamide (SEQ ID NO: 29),
Acyl-NH-AYPYDVPDYASENLYFQG(GABA)Orn-iodoacetamide (SEQ ID NO: 30), and
Acyl-NH-AYPYDVPDYASENLYFQGVOrn-iodoacetamide (SEQ ID NO: 31).

Therefore, by way of example only, if the reagent of step c) is
Acyl-NH-AYPYDVPDYASENLYPQGK-iodoacetamide (SEQ ID NO: 32) the reagent of step f) would be
Acyl-NH-AYPYDVPDYASENLYPQGOrn-iodoacetamide (SEQ ID NO: 33); and if the reagent of step c) is
Acyl-NH-AYPYDVPDYASENLYPQGOrn-iodoacetamide (SEQ ID NO: 34), the reagent of step f) would be
Acyl-NH-AYPYDVPDYASENLYPQGK-iodoacetamide (SEQ ID NO: 35).

Preferably, the reagent of step c) or of step f) reacts with the reactive side chain of one or more of the amino acid residues of the proteins in the first or second protein sample. By "reactive side chain" it is meant the amino acid side chain that is functionalized, or an amino acid side chain that is other than straight chain or branched alkyl. Therefore, the reagent reacts with the first or second protein at an amino acid residue selected from the group consisting of tyrosine, tryptophan, cysteine, methionine, proline, serine, threonine, lysine, histidine, arginine, aspartic acid, glutamic acid, asparagine, and glutamine. In certain embodiments, the reagent reacts at an amino acid residue selected from the group consisting of tyrosine, cysteine, proline, and histidine. In another embodiment, the site of reaction is a cysteine.

In some embodiments of the present invention, the chromatographic separation of step 1) is a multi-dimensional liquid chromatographic separation, which may be a two-dimensional liquid chromatographic separation or a three-dimensional liquid chromatographic separation. The dimensions of the multidimensional liquid chromatographic separation are selected from the group consisting of size differentiation, charge differentiation, hydrophobicity, hydrophilicity, and polarity. In some embodiments, at least one dimension of the multi-dimensional liquid chromatographic separation is separation using size differentiation. Embodiments of the invention include those in which one dimension of the multi-dimensional liquid chromatographic separation is separation using charge differentiation. In other embodiments, one dimension of the multi-dimensional liquid chromatographic separation is separation using hydrophobicity or hydrophilicity.

In another embodiment the mass analysis of step n) is a multi-dimensional mass analysis, which may be a two-dimensional mass analysis (i.e., tandem mass spectrometry).

It is well-known in the art to separate fragments of a solution using chromatography and, in tandem thereto, analyze the mass spectra of each fragment. The technique is formally known in the art as LC-MS or LC-MS/MS analysis. Multi-dimensional chromatography is also well-known in the art, where multiple columns are used in tandem, or the same column is packed with segments of different material that can separate the sample using different criteria See, for example, Link et al., (1999) or Opitek et al. (1997), above. Multi-dimensional mass analysis is a technique known to those skilled in the art as well. In this technique, following an initial ionization, an ion of interest is selected. The selected ion is fragmented and each fragment (known as "daughter ion" or "progeny ion") is now capable of being either analyzed or be subjected to further fragmentation. The technique is fully described in Siuzdak, Mass Spectrometry for Biotechnology, Academic Press, San Diego, Calif., 1996, which is incorporated by reference herein in its entirety.

In certain embodiments, the preparation of proteins from step a) is subjected to orthogonal chromatography before proceeding with the labeling in step c). Orthogonal chromatography is a technique well-known in the art.

Quantitative relative amounts of proteins in one or more different samples containing protein mixtures (e.g., biological fluids, cell or tissue lysates, etc.) can be determined using chemically similar, affinity tagged and differentially labeled reagents to affinity tag and differentially label proteins in the different samples. The label may be differentiated by having additional methylene groups, which would result in the mass of the two labels be different by an integer multiple of 14.

In this method, each sample to be compared is treated with a different labeled reagent to tag certain proteins therein with the affinity label. The treated samples are then combined, preferably in equal amounts, and the proteins in the combined sample are enzymatically digested, if necessary, to generate peptides. Some of the peptides are affinity tagged and in addition tagged peptides originating from different samples are differentially labeled. As described above, affinity labeled peptides are isolated, released from the capture reagent and analyzed by (LC/MS). Peptides characteristic of their protein origin are sequenced using $(MS)^n$ techniques allowing identification of proteins in the samples. The relative amounts of a given protein in each sample is determined by comparing relative abundance of the ions generated from any differentially labeled peptides originating from that protein. The method can be used to assess relative amounts of known proteins in different samples. The method is described in U.S. Pat. No. 5,538,897, issued Jul. 23, 1996, to Yates et al., which is incorporated herein by reference in its entirety, including any drawings.

Further, since the method does not require any prior knowledge of the type of proteins that may be present in the samples, it can be used to identify proteins which are present at different levels in the samples examined. More specifically, the method can be applied to screen for and identify proteins which exhibit differential expression in cells, tissue or biological fluids. It is also possible to determine the absolute amount of specific proteins in a complex mixture. In this case, a known amount of internal standard, one for each specific protein in the mixture to be quantified, is added to the sample to be analyzed. The internal standard is an affinity tagged peptide that is identical in chemical structure to the affinity tagged peptide to be quantified except that the internal standard is differentially labeled, either in the peptide or in the affinity tagged portion, to distinguish it from the affinity tagged peptide to be quantified. The internal standard can be provided in the sample to be analyzed in other ways. For example, a specific protein or set of proteins can be chemically tagged with a labeled affinity tagging reagent. A known amount of this material can be added to the sample to be analyzed. Alternatively, a specific protein or set of proteins may be labeled with additional methylene groups and then derivatized with an affinity tagging reagent.

Also, it is possible to quantify the levels of specific proteins in multiple samples in a single analysis (multiplexing). For example, a set of five different samples can be reacted with one of SEQ ID NO:27–SEQ ID NO:31, then follow with subsequent steps as described herein. In this case, affinity tagging reagents used to derivatize proteins present in different affinity tagged peptides from different samples can be selectively quantified by mass spectrometry. This may be achieved by using reagents whose molecular mass varies from one sample to another by an integer multiple of 14. So, for example, the Link group in one reagent may feature ornithine whereas the Link group in another reagent may feature arginine or lysine. Similarly, the Z groups in the different reagent may vary such that the molecular mass of the reagent varies by an integer multiple of 14. It is also understood that other amino acids may also be featured. For example, the lighter reagent may have valine whereas the heavier reagent may feature leucine or isoluecine in its stead. The same would be true for having asparagine in the lighter reagent and glutamine in the heavier reagent, or aspartic acid in the lighter reagent and glutamic acid in the heavier reagent.

In this aspect of the invention, the method provides for quantitative measurement of specific proteins in biological fluids, cells or tissues and can be applied to determine global protein expression profiles in different cells and tissues. The same general strategy can be broadened to achieve the proteome-wide, qualitative and quantitative analysis of the state of modification of proteins, by employing affinity reagents with differing specificity for reaction with proteins. The method and reagents can be used to identify low abundance proteins in complex mixtures and can be used to selectively analyze specific groups or classes of proteins such as membrane or cell surface proteins, or proteins contained within organelles, sub-cellular fractions, or biochemical fractions such as immunoprecipitates. Further, these methods can be applied to analyze differences in expressed proteins in different cell states. For example, the methods and reagents herein can be employed in diagnostic assays for the detection of the presence or the absence of one or more proteins indicative of a disease state, such as cancer.

The methods described herein can also be applied to determine the relative quantities of one or more proteins in two or more protein samples. The proteins in each sample are reacted with affinity tagging reagents which are substantially chemically identical but differentially labeled. The samples are combined and processed as one. The relative quantity of each tagged peptide which reflects the relative quantity of the protein from which the peptide originates is determined by the integration of the respective mass peaks by mass spectrometry.

The methods described herein can be applied to the analysis or comparison of multiple different samples. Samples that can be analyzed by methods of this invention include cell homogenates; cell fractions; biological fluids including urine, blood, and cerebrospinal fluid; tissue homogenates; tears; feces; saliva; lavage fluids such as lung or peritoneal ravages; mixtures of biological molecules including proteins, lipids, carbohydrates and nucleic acids generated by partial or complete fractionation of cell or tissue homogenates.

The methods described herein employ MS and $(MS)^n$ methods. While a variety of MS and $(MS)^n$ are available and may be used in these methods, Matrix Assisted Laser Desorption Ionization MS (MALDI/MS) and Electrospray ionization MS (ESI/MS) methods are preferred.

III. Proteomic Analysis

Another aspect of the present invention relates to a method for proteomic analysis, comprising:
a) preparing a protein sample or a peptide sample from cells;
b) reacting the protein sample or the peptide sample with a reagent of the formula:

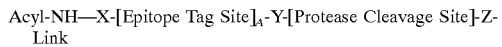

Acyl-NH—X-[Epitope Tag Site]$_A$-Y-[Protease Cleavage Site]-Z-Link where:
A is an integer from 1 to 12;
X is an amide bond of formula —C(O)—NR—, where R is hydrogen or lower alkyl, or X is an amino acid sequence comprising between 0 to 50 amino acids;
Y is an amide bond of formula —C(O)—NR—, where R is hydrogen or lower alkyl, or Y is an amino acid sequence comprising between 0 to 50 amino acids;
Z is an amide bond of formula —C(O)—NR—, where R is hydrogen or lower alkyl, or Z is an amino acid sequence comprising between 0 to 10 amino acids;
Link is selected from the group consisting of Lys-ε-iodoacetamide, Arg-δ-iodoacetamide, and Orn-δ-iodoacetamide;
Epitope Tag Site is a sequence of amino acids, and
Protease Cleavage Site is a sequence of amino acids that is a cleavage site for a highly specific protease enzyme;
c) subjecting the reacted proteins or peptides from step b) to proteolysis at a site on the protein samples or at a site on the peptide samples, the site being other than the Protease Cleavage Site;
d) subjecting the proteolyzed reacted proteins or the proteolyzed reacted peptides from step c) to an affinity chromatography system comprising a second amino acid sequence attached to a solid support, thereby forming bound proteins and non-bound proteins,
where the Epitope Tag Site of the reagent and the second amino acid sequence bind with high specificity to each other;
e) eluting the non-bound proteins from the affinity chromatography system;
f) subjecting the affinity chromatography system from step e) to a protease specific for the Protease Cleavage Site, thereby forming a cleaved protein mixture;
g) eluting the cleaved protein mixture from the affinity chromatography system of step f);
h) isolating the cleaved protein mixture obtained from step g);
i) subjecting the cleaved protein mixture from step h) to chromatographic separation, followed by mass analysis;
j) comparing the results of step i) to:
  1) determine the ratio of amounts of compounds in the sample separated by a molecular weight of 14 atomic mass units; and
  2) identify the various modified proteins by comparing the results obtained for each modified protein to protein databases containing chromatographic and molecular weight correlations.

The term "proteomic analysis" refers to identifying the proteome of a cell. The "proteome" of a cell is the collection of all the proteins expressed by the cell at the time the proteomic analysis is undertaken. It is understood that, unlike the genome of a cell, which is invariable, the proteome of a cell varies depending on many factors, including the age of the cell, the environmental conditions surrounding the cell, and the position of the cell in its life cycle.

In the above methods, the reagent reacts with the reactive side chain of one or more of the amino acid residues of the first or second protein. Therefore, the reagent reacts with the protein at an amino acid residue selected from the group consisting of tyrosine, tryptophan, cysteine, methionine, proline, serine, threonine, lysine, histidine, arginine, aspartic acid, glutamic acid, asparagine, and glutamine. In certain embodiments, the reagent reacts at an amino acid residue selected from the group consisting of tyrosine, cysteine, proline, and histidine. In another preferred embodiment, the site of reaction is a cysteine.

In some embodiments of the present invention, the chromatographic separation of step i) is a multi-dimensional liquid chromatographic separation, which may be a two-dimensional liquid chromatographic separation or a three-dimensional liquid chromatographic separation. The dimensions of the multi-dimensional liquid chromatographic separation are selected from the group consisting of size differentiation, charge differentiation, hydrophobicity, hydrophilicity, and polarity. In some embodiments, at least one dimension of the multi-dimensional liquid chromatographic separation is separation using size differentiation. Embodiments of the invention include those in which one dimension of the multi-dimensional liquid chromatographic separation is separation using charge differentiation. In other embodiments, one dimension of the multi-dimensional liquid chromatographic separation is separation using hydrophobicity or hydrophilicity.

In another embodiment the mass analysis of step i) is a multi-dimensional mass analysis, which more preferably, may be a two-dimensional mass analysis.

In certain embodiments, the preparation of proteins from step a) is subjected to orthogonal chromatography before proceeding with the labeling in step b).

In one aspect, the invention provides a mass spectrometric method for identification and quantification of one or more proteins in a complex mixture which employs affinity labeled reagents in which the Link group is a group that selectively reacts with certain groups that are typically found in peptides (e.g. sulfhydryl, amino, carboxy, homoserine, or lactone groups). One or more affinity labeled reagents with different Link groups are introduced into a mixture containing proteins and the reagents react with certain proteins to tag them with the affinity label. It may be necessary to pretreat the protein mixture to reduce disulfide bonds or otherwise facilitate affinity labeling. After reaction with the affinity labeled reagents, proteins in the complex mixture are cleaved, e.g., enzymatically, into a number of peptides. This digestion step may not be necessary, if the proteins are relatively small. Peptides that remain tagged with the affinity label are isolated by an affinity isolation method, e.g., affinity chromatography, via their selective binding to the capture reagent. Isolated peptides are released from the capture reagent by displacement of the Epitope Tag Site or cleavage of the linker, and released materials are analyzed by liquid chromatography/mass spectrometry (LC/MS). The sequence of one or more tagged peptides is then determined by $(MS)^n$ techniques. At least one peptide sequence derived from a protein will be characteristic of that protein and be indicative of its presence in the mixture. Thus, the sequences of the peptides typically provide sufficient information to identify one or more proteins present in a mixture.

IV. Quantitative Proteome Analysis

The method comprises the following steps:

Reduction. Disulfide bonds of proteins in the sample and reference mixtures are chemically reduced to free SH groups. The preferred reducing agent is tri-n-butylphosphine which is used under standard conditions. Alternative reducing agents include mercaptoethanol, 2-methylthioethanol, 2-methylthio-1-hexanol, and dithiothreitol. If required, this reaction can be performed in the presence of solubilizing agents including high concentrations of urea and detergents to maintain protein solubility. The reference and sample protein mixtures to be compared are processed separately, applying identical reaction conditions.

Derivatization of SH groups with an affinity tag. Free SH groups of the sample protein are derivatized with a reagent of the invention. The reagent reacts with the free SH group through the Link group.

Each sample is derivatized with a different reagent having a different mass. Derivatization of SH groups is preferably performed under slightly basic conditions (pH 8.5) for 90 min at about room temperature. For the quantitative, comparative analysis of two samples, one sample each (termed "reference sample" and "sample") are derivatized with two different reagents, whose molecular mass differs by an integer multiple of 14. For the comparative analysis of several samples one sample is designated a reference to which the other samples are related.

Combination of labeled samples. After completion of the affinity tagging reaction defined aliquots of the samples labeled with different reagents are combined and all the subsequent steps are performed on the pooled samples. Combination of the differentially labeled samples at this early stage of the procedure eliminates variability due to subsequent reactions and manipulations. Preferably equal amounts of each sample are combined.

Removal of excess affinity tagged reagent. Excess reagent is adsorbed, for example, by adding an excess of SH-containing beads to the reaction mixture after protein SH groups are completely derivatized. Beads are added to the solution to achieve about a 5-fold molar excess of SH groups over the reagent added and incubated for 30 min at about room temperature. After the reaction the beads are removed by centrifugation.

Protein digestion. The proteins in the sample mixture are digested, typically with trypsin. Alternative proteases are also compatible with the procedure as in fact are chemical fragmentation procedures. In cases in which the preceding steps were performed in the presence of high concentrations of denaturing solubilizing agents, the sample mixture is diluted until the denaturant concentration is compatible with the activity of the proteases used. This step may be omitted in the analysis of small proteins.

Affinity isolation of the affinity tagged peptides by interaction with a capture reagent. The tagged peptides are isolated on anti-HA antibodies-agarose. After digestion the pH of the peptide samples is lowered to 6.5 and the tagged peptides are immobilized on beads coated with anti-HA. The beads are extensively washed. The last washing solvent includes 10% methanol to remove residual SDS.

Release of the captured peptides with specific protease. A solution of TEV in TRIS at pH 7.5 is added to the column and digestion is allowed to proceed. The bound peptides are cleaved from the column by incubation at 30° C. for 6 hours.

Analysis of the isolated, derivatized peptides by $\mu$LC-$(MS)^n$ or CE-$(MS)^n$ with data dependent fragmentation. Methods and instrument control protocols well-known in the art and described, for example, in Ducret et al. (1998); Figeys and Aebersold (1998); Figeys et al. (1996); or Haynes et al. (*Electrophoresis* 19:939–945 (1998)) are used.

In this last step, both the quantity and sequence identity of the proteins from which the tagged peptides originated can be determined by automated multistage MS. This is achieved by the operation of the mass spectrometer in a dual mode in which it alternates in successive scans between measuring the relative quantities of peptides eluting from the capillary column and recording the sequence information of selected peptides. Peptides are quantified by measuring in the MS mode the relative signal intensities for pairs of peptide ions of identical sequence that are tagged with the lighter or heavier forms of the reagent, respectively, and which therefore differ in mass by the mass differential encoded within the affinity tagged reagent. Peptide sequence information is automatically generated by selecting peptide ions of a particular mass-to-charge (m/z) ratio for collision-induced dissociation (CID) in the mass spectrometer operating in the $(MS)^n$ mode. (Link et al. *Electrophoresis* 18:1314–1334 (1997); Gygi et al. *Nature Biotechnol* 17:994–999 (1999); Gygi et al., *Cell Biol* 19:1720–1730 (1999)). The resulting CID spectra are then automatically correlated with sequence databases to identify the protein from which the sequenced peptide originated. Combination of the results generated by MS and $(MS)^n$ analyses of affinity tagged and differentially labeled peptide samples therefore determines the relative quantities as well as the sequence identities of the components of protein mixtures in a single, automated operation.

This method can also be practiced using other affinity tags and other protein reactive groups, including amino reactive groups, carboxyl reactive groups, or groups that react with homoserine lactones.

The approach employed herein for quantitative proteome analysis is based on two principles. First, a short sequence of contiguous amino acids from a protein contains sufficient information to uniquely identify that protein. Protein identification by $(MS)^n$ is accomplished by correlating the sequence information contained in the CID mass spectrum with sequence databases, using sophisticated computer searching algorithms (Yates, III et al. U.S. Pat. No. 5,538,897). Second, pairs of peptides tagged with lighter and heavier Link groups or Z groups, respectively, are chemically similar and therefore serve as mutual internal standards for accurate quantification. The MS measurement readily differentiates between peptides originating from different samples, representing for example different cell states, because of the difference between the distinct reagents attached to the peptides. The ratios between the intensities of the differing weight components of these pairs or sets of peaks provide an accurate measure of the relative abundance of the peptides (and hence the proteins) in the original cell pools.

Specifically, the peptide labeling moiety consists of a lysine residue modified with an iodoacetamido functional group on the ε-amino side chain. The synthetic chemistry necessary for this modification reaction is readily available in the literature. The synthetic peptides contain two additional motifs: a peptide epitope tag for high affinity purification; and a highly specific protease site for releasing the affinity purified labeled peptides from the affinity matrix. In addition, these synthetic peptides can readily be prepared as isoforms of two different masses by the simple expedient of using an ornithine in place of lysine to introduce a 14 mass unit difference in the carboxyl terminal acid.

Examples of the reagents (SEQ ID NO: 36 and SEQ ID NO: 37) are thus:

```
Ala-[Tyr-Pro-Tyr-Asp-Val-Pro-Asp-Tyr-Ala]-Ser-(Glu-Asn-Leu-Tyr-Phe-Gln-Gly)-----Iodoacetamide
                 |                              |                            Lys (Epitope Tag Site)        (Protease Cleavage Site)
                 |                              |
Ala-[Tyr-Pro-Tyr-Asp-Val-Pro-Asp-Tyr-Ala]-Ser-(Glu-Asn-Leu-Tyr-Phe-Gln-Gly)-----Iodoacetamide
                                                                             Orn
```

The peptide sequence in the square brackets is an Epitope Tag Site and the sequence in parentheses is a Protease Cleavage Site. In the case shown here, the peptide sequence YPYDVPDYA (SEQ ID NO: 38) is an influenza hemagglutinin (HA) epitope tag. This part of the reagent could be replaced by any other epitope tag, or multiple copies of a single tag for higher efficiency purification, or parallel copies of different tags for higher specificity purification. Examples of other Epitope Tag Sites include Flag, His-6, and c-myc.

The protease cleavage site shown here is that of TEV protease, which is commercially available. This enzyme has been shown to cleave at only one protein site in the entire yeast genome, thus indicating that the enzyme is highly specific for an extremely rare sequence. This part of the reagent could be replaced by any other highly specific protease cleavage site, either commercially available, such as Factor Xa, or Pharmacia Prescission Enzyme, or one that is newly discovered. The amino acid indicated in bold is used to provide a site of attachment for the iodoacetamide group, hence we have used lysine which contains an ε-amino side chain that is suitable for the purpose. This amino acid is also used to introduce a differential mass between the two reagents, and this can be readily accomplished by using ornithine in place of lysine. Ornithine is commercially available and differs from lysine only by the presence of one additional methyl group, which makes it 14 amu (atomic mass unit) heavier than lysine. Arginine is also commercially available and its molecular weight is 28 amu (i.e., 2×14) heavier than lysine. This part of the reagent could be replaced with any other amino acid or similar molecule that provided an attachment site for the iodoacetamide group. Finally, the integral difference of 14 amu could be further enhanced by the choice of two amino acids differing by 14 amu (e.g., valine and leucine) in the Z portion of the peptide labeling moiety.

V. Qualitative Proteome Analysis

In addition to the above methods, the methods of the invention may be used to determine the proteomic differences in an organism or cell based on the change in the cell's environmental condition. Thus, for example, one may compare the proteome of the cells of two plants of the same species, one having encountered high salt concentrations and the other low salt concentrations, thereby determining the effect of salt concentration on the plant's proteome.

It is also within the scope of the present invention that the two modes of analysis discussed herein, i.e., the qualitative and quantitative proteome analyses, are exercised in conjunction with each other. Thus, by way of example only, one may compare the proteome of the cells of two plants of the same species, one having encountered higher temperatures than the other, thereby not only determining the effect of heat on the proteome in terms of which proteins are expressed, but also determining the effect of heat on the level of expression of each protein of interest.

In practicing the present invention to achieve the above end, one may use a number of different compounds of the present invention, having different masses (yet all within an integer multiple of 14 from each other), and mark different proteins of the cells with the different reagents. By applying the multidimensional LC/MS techniques described herein, one is able to determine which proteins, and to what extent, are expressed in the cells.

IV. Fusion Proteins

Another aspect of the invention relates to a process for preparing a fusion protein of Formula IV or V:

(IV) Protein-Acyl-N—X-[Epitope Tag Site]$_A$-Y-[Protease Cleavage Site ]-Z-[Lys-δ-N-iodoacetamide]

(V) Protein-Acyl-NH—X-alk-O-Ph-CH$_2$—Z-Link where A, X, Y, Z, alk, Ph, Link, Epitope Tag Site, and Protease Cleavage Site are as defined herein comprising, a) preparing a fusion protein sample of Formula II or III from cells (II) Protein-Acyl-NH—X-[Epitope Tag Site]$_A$-Y-[Protease Cleavage Site]-Z-Orn-δ-NHCOCH$_2$ (III) Acyl-NH—X-alk-O-Ph-CH$_2$—Z—NHCOCH$_2$ b) reacting the protein sample with a Link or with iodoacetamide.

In another aspect, the invention relates to a process for preparing a fusion protein of Formula VI:

(VI) Protein-Acyl-N—X-[Epitope Tag Site]$_A$-Y-[Protease Cleavage Site ]-Z-[Lys-δ-N-iodoacetamide]

where A, X, Y, Z, alk, Ph, Link, Epitope Tag Site, and Protease Cleavage Site are as defined herein comprising, a) preparing a fusion protein sample of Formula VII from cells (VII) Protein-Acyl-NH—X-[Epitope Tag Site]$_4$-Y-[Protease Cleavage Site]-Z-Lys-δ-NHCOCH$_2$ b) reacting the protein sample with iodoacetamide.

Markers that are useful in plant breeding, genetics, and diagnostics are disclosed in U.S. Provisional Patent Application No. 60/264,226, entitled "Cereal Simple Sequence Repeat Markers," filed on Jan. 26, 2001, which is hereby incorporated by reference in its entirety.

VI. Databases

Aspects of the invention not only include the chemical compounds and MS data described above, but also include data files (e.g.: databases) corresponding to these compounds and data. For example, the amino acid sequences of the labeled compounds can be created and manipulated in silico. These data files can be stored in a conventional computer system on any type of temporary or permanent storage. Examples of such storage include Read Only Memory, Random Access Memory, Hard Disk, Floppy Disk, CD-ROM and the like.

In addition to data relating to the modified amino acid sequences, aspects of the invention include data files of the MS data itself. A data file of, for example, a cell that has been subjected to high salt conditions, can be stored to a database and thereafter compared to other data files of cells having different treatments. Thus, aspects of the invention contemplate analyzing the differences between organisms or cells by comparing MS data gathered from the methods described above.

EXAMPLES

Examples are provided below to illustrate different aspects and embodiments of the present invention. These examples are not intended in any way to limit the disclosed invention. Rather, they illustrate the compounds and the methodology by which the protein analysis of the invention may be practiced.

The following proteins and reagents were purchased from Sigma, St. Louis, Mo., USA: rabit glyceraldehydes-3-phosphate dehydrogenase, *E.Coli* β-galactosidase, rabbit phosphorylase b, chicken ovalbumin, bovine β-lactoglobulin, bovine a-lactalbumin, bovine serum albumin, dimethylformamide (DMF), Iodoacetic anhydride, Urea, tris-hydrochloride, acid washed glass beads, and diisopropylethylamine (DEA). Tributyl phosphine was purchased from BioRad (Hercules, Calif.). Synthetic peptides were custom made by QCB/Biosource International (Hopkinton, Mass.). HA affinity matrix and Lys-C were from Roche Diagnostics (Indianapolis, Ind.), and PreScission protease was from Amersham Pharmcia Biotech (Uppsala, Sweden). HPLC grade acetonitrile (ACN) and HPLC grade methanol was purchased from Fischer Scientific (Fair Lawn, N.J.). Yeast extract were products of BD Biosciences (Sparks, Md.). Heptaflourobutyric acid (HFBA) was obtained from Pierce (Rockford, Ill.). SPEC Plus PT C18 solid phase extraction pipette tips were purchased from Ansys Diagnostics (Lake Forest, Calif.). Glacial acetic acid was purchased from Malinckrodt Baker Inc. (Paris, Ky.).

Example 1

Synthesis of Peptide Labeling Moiety (or Peptide Encoded Tags. "PEPTaps")

A pair of PEPTags, described generally above, was synthesized from peptides with following sequences: Ac-AYPYDVPDYASENLYFQGK (SEQ ID NO: 39) and AYPYDVPDYASENLYFQGOrn (SEQ ID NO: 40). In dry DMF containing excess (2–3 molar equivalents) DIEA, each of the peptides was mixed with two molar equivalents of iodoacetic anhydride for 10 min at room temperature under N$_2$ gas, to give Lys-PEPTag and Orn-PEPTag, respectively. The reaction was terminated by adding acetic acid. Solvent was removed by vacuum centrifugation, and the product was purified by reverse-phase FPLC, and analyzed by MALDI MS (TofSpec 2E, Micromass, Beverly, Mass.) and ESI MS/MS (API 3, PE Sciex, Foster City, Calif.).

In order to demonstrate that the mass spectrometric ionization efficiency of the two synthesized peptide tags was essentially equal, the two products were mixed in different ratios and analysed by LC-MS. The ratio of the measured peak areas gave the data shown in the following table.

| Amount of tag1 (pmol) | Amount of tag2 (pmol) | Calculated ratio | Measured ratio |
|---|---|---|---|
| 30 | 3 | 10:1 | 11.95:1 |
| 15 | 3 | 5:1 | 5.19:1 |
| 7.5 | 3 | 2.5:1 | 2.70:1 |
| 3.75 | 3 | 1.25:1 | 0.97:1 |
| 1.875 | 3 | 0.625:1 | 0.64:1 |
| 0.375 | 3 | 0.125:1 | 0.11:1 |

Example 2

PEPTag Qualitative Protein Analysis: Simplification of Complex Mixtures

We tested the PEPTag method, described generally herein, on Bovine Serum Albumin (BSA). 200 μL BSA (0.25 mg/mL) was denatured and reduced in a solution containing 0.1% SDS, 5 mM tributyl phosphine and 50 mM Tris buffer (pH 8.5) for 3 min at 100° C. and for 1 hour at 37° C. The side chains of cysteinyl residues were derivatized with a tenfold molar excess of Lys-PEPTag. Tagged protein was digested by trypsin overnight at 37° C. Trypsin activity was quenched with trypsin inhibitor and the peptide mixture bound to anti-HA affinity matrix for 2 hours at 4° C. The anti-HA resin with bound peptides was washed in equilibration-buffer (20mM Tris, pH 7.5; 0.1 M NaCl; 0.1 mM EDTA), 3×10 min. at 4° C. The bound peptides were cleaved from the matrix by incubation with TEV protease for 6 hours at 30° C. The cleaved peptides were analyzed by either Matrix Assisted Laser Desorption Ionization Mass Spectrometry (MALDI MS), or separated and analyzed by μLC-MS/MS. Using the Sequest database searching algorithm (Yates, III et al. U.S. Pat. No. 5,538,897), the resulting MS/MS spectra were correlated with the sequence database.

The sequence of bovine serum albumin is shown below:

```
              SW:ALBU_BOVIN P02769 bos taurus (bovine). serum albumin precursor.
                                    12/1998 [MASS = 69293]

MKWVTFISLL  LLFSSAYSRG  VFRRDTHKSE  IAHRFKDLGE  EHFKGLVLIA  FSQYLQQCPF           (SEQ ID NO: 45)
DEHVKLVNEL  TEFAKTCVAD  ESMAGCEKSL  HTLFGDELCK  VASLRETYGD  MADCCEKQEP
ERNECFLSHK  DDSPDLPKLK  PDPNTLCDEF  KADEKKFWGK  YLYEIARRHP  YFYAPELLYY
ANKYNGVFQE  CCQAEDKGAC  LLPKIETMRE  KVLASSARQR  LRCASIQKFG  ERALKAWSVA
RLSQKFPKAE  FVEVTKLVTD  LTKVHKECCH  GDLLECADDR  ADLAKYICDN  QDTISSKLKE
CCDKPLLEKS  HCIAEVEKDA  IPENLPPLTA  DFAEDKDVCK  NYQEAKDAFL  GSFLYEYSRR
HPEYAVSVLL  RLAKEYEATL  EECCAKDDPH  ACYSTVFDKL  KHLVDEPQNL  IKQNCDQFEK
LGEYGFQNAL  IVRYTRKVPQ  VSTPTLVEVS  RSLGKVGTRC  CTKPESERMP  CTEDYLSLIL
NRLCVLHEKT  PVSEKVTKCC  TESLVRRRPC  FSALTPDETY  VPKAFDEKLF  TFHADICTLP
DTEKQIKKQT  ALVELLKHKP  KATEEQLKTV  MENFVAFVDK  CCAADDKEAC  FAVEGPKLVV  STQTALA
```
>average mass = 69294, pI = 5.82

Cysteine-containing peptides indicated in bold-underline are those detected in the experiment described in example 2. The protein is successfully identified from each peptide tandem MS spectra, and the complex total tryptic mixture of peptides is considerably simplified. The peptides are shown in more detail in the table below, with C# indicating a peptag-modified cysteine residue.

| Position | Mass (MH+) | Peptide sequence |
|---|---|---|
| 89–100 | 1363.57 | SLHTLFGDELC#K (SEQ ID NO: 46) |
| 286–297 | 1387.50 | YIC#DNQDTISSK (SEQ ID NO: 47) |
| 139–151 | 1520.74 | LKPDPNTLC#DEFK (SEQ ID NO: 48) |
| 510–523 | 1571.78 | C#FSALTPDETYVPK (SEQ ID NO: 49) |
| 469–482 | 1668.96 | MPC#TEDYLSLILNR (SEQ ID NO: 50) |

-continued

| Position | Mass (MH+) | Peptide sequence |
|---|---|---|
| 508–523 | 1825.08 | RPC#FSALTPDETYVPK (SEQ ID NO: 51) |
| 123–138 | 1846.02 | NEC#FLSHKDDSPDLPK (SEQ ID NO: 52) |
| 529–544 | 1852.11 | LFTFHADIC#TLPDTEK (SEQ ID NO: 53) |
| 118–138 | 2485.68 | QEPERNEC#FLSHKDDSPDLPK (SEQ ID NO: 54) |
| 461–482 | 2599.99 | CTKPESERMPC#TEDYLSLILNR (SEQ ID NO: 55) |

Example 3

PEPTag Quantitative Protein Analysis: Differential Labeling

Figure 6:
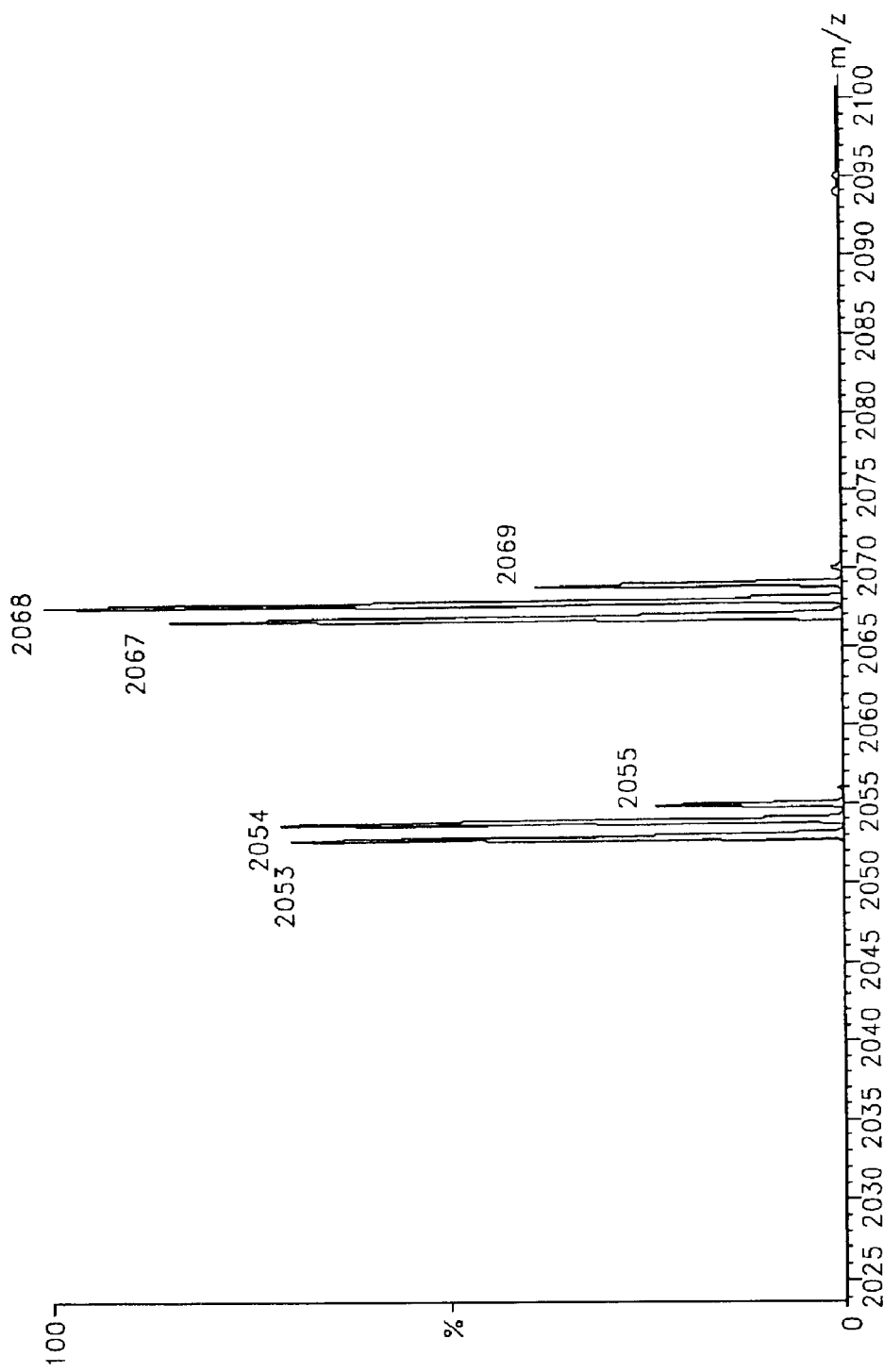
FIG. 6 is a printout showing the MALDI mass spectrum of a pair of PEPTag labeled peptides of identical sequences. The m/z difference depends on the charge state. It is either 14 or 7 for charge state one or two.
Figure 8:
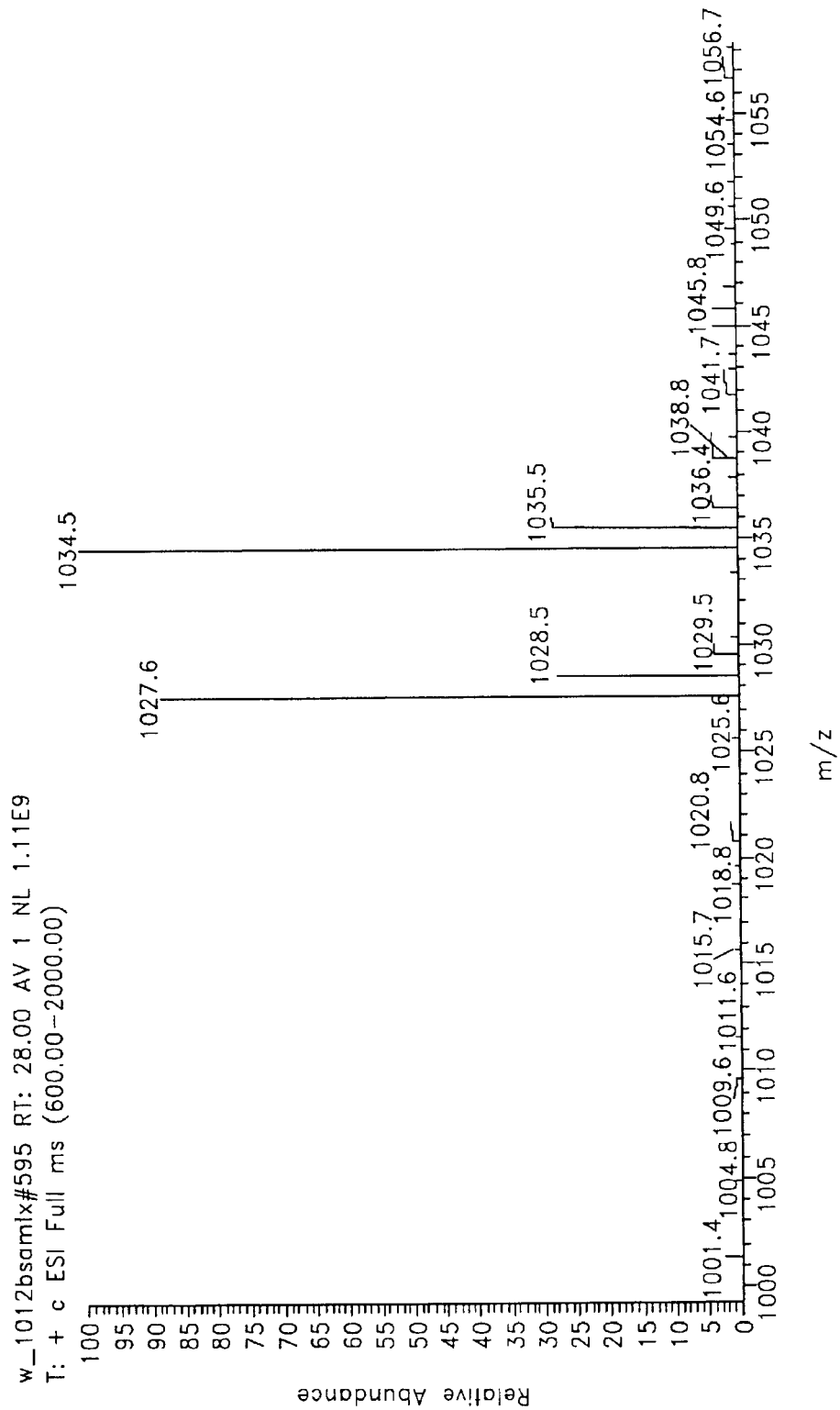
FIG. 8 is a printout of the ESI mass spectrum of the pair of PEPTag labeled peptides of identical sequences. The m/z difference is 7 for doubly charged ions.

We tested the PEPTag quantitative strategy on two mixtures containing the same two proteins at different concentrations. Mixture 1 had 500 pmol BSA (0.1 mg/mL) and 400 pmol β-lactoglobulin (0.1 mg/mL) and was reacted with 9 nmol Lys-PEPTag. Mixture 2 had 250 pmol BSA (0.05 mg/mL) and 800 pmol β-lactoglobulin (0.2 mg/mL) and was reacted with 9 nmol Orn-PEPTag. Protein denaturation, reduction, tagging, and digestion were the same as described above. The two samples were combined after tryptic digestions, and bound to anti-HA matrix. TEV digestion and MS analysis were as described in Example 2. Peptides were quantified by measuring, in the MS mode, the relative signal intensities for pairs of peptide ions of identical sequence, tagged with Lys or Orn-PEPTags, respectively. The results are shown in FIGS. 6, 7, and 8 and the following table.

| Protein | Peptide sequence identified | Observed ratio | Mean ± S.D. | Expected ratio |
|---|---|---|---|---|
| Bovine serum albumin | SLHTLFGDELC#K (SEQ ID NO:56) | 2.19 | 2.05 ± 0.10 | 2.00 |
| | GLVLIAFSQYLQQC#PFDEHVK (SEQ ID NO: 57) | 1.96 | | |
| | GLVLIAFSQYLQQC#PFDEHVKLVNELTEFAK (SEQ ID NO: 58) | 1.99 | | |
| Beta-lactogobulin | VYVEELKPTPEGDGLEILLQKWENDEC#AQKK (SEQ ID NO: 59) | 0.40 | 0.46 ± 0.05 | 0.50 |
| | LSFNPTQLEEQC#HI (SEQ ID NO: 60) | 0.51 | | |

Example 4

Proteome Analysis

A. Perturbed Cell Sample Versus Normal Cell Sample

A biological sample of interest is subjected to a treatment expected to cause physiological changes, such as treating tissue culture cells with a drug sample. Protein samples are prepared from the normal and perturbed cells. The normal cell protein sample is labeled at all cysteine residues using the first (lysine-based) reagent shown above, and the perturbed cell protein sample is labeled at all cysteine residues using the heavier (ornithine-based) version of the reagent as shown above. The two labeled samples are then combined and protease digested, typically with trypsin, to produce a very complex peptide mixture. This complex mixture is then passed over an anti-HA tag affinity tag column that retains only those tryptic fragments containing labeled cysteine residues, allowing all other material to be washed away. The peptides are then released from the column by addition of TEV protease, producing a mixture of peptides labeled with either lysine or ornithine attached via an acetamido group.

This complex mixture is then analyzed using microscale high-performance liquid chromatography-tandem mass spectrometry. Two distinct classes of information are then obtained during the course of a single experiment. Firstly, the relative amounts of each peptide that were produced from the initial normal and perturbed samples are accurately quantified by measuring the ratio of peak areas for a given peak pair differing by 14 amu. Since the two samples have been mixed together very early in the experimental process, variation in sampling handling between the two samples is essentially eliminated as for each pair there is a mutual internal standard present in the same sample. Secondly, the identity of each peptide is determined by tandem mass spectrometric fragmentation and database searching using established methods.

The result of this experiment is simultaneous peptide identification and relative quantification. Thus, for any experimental perturbation that can be applied to cells, it would be possible to identify which proteins were up and down regulated, and quantify the amount of any change detected.

B. Whole Cell Analysis

Another type of experiment is performed using just one of the reagents described above, where massively parallel protein identification is required such as characterizing the proteome of a whole organism or cell type. Using the technique outlined above for enrichment of labeled cysteine containing peptides, the number of proteins that can be identified from a very complex mixture is dramatically increased. This is due to the fact the number of peptides analyzed from each protein, even those of high abundance, is reduced, thus allowing greater coverage of the range of proteins present. This coverage is increased still further by using two-dimensional liquid chromatography prior to tandem mass spectrometry in order to maximize the number of peptides analyzed. It is also possible to perform a further orthogonal chromatography step prior to labeling, thus increasing the number of peptides identified even more. Using such a system, it is possible to describe the entire proteome of a simple organism in a single experiment.

The applications of this method are almost limitless. Any biological sample containing proteins benefits from either a complete description of all the proteins present, or a complete description and quantification of changes that occur in response to a physiological stimulus, or both.

The complete cataloging type of experiment, set forth in Subsection B, above, is best limited to organisms with complete sequences available, although it should be noted that the list now includes humans.

Example 5

Synthesis of Affinity Peptide Encoded Tags (APEPTags)

A pair of APEPTags was synthesized from peptides with following sequences: Ac-AYPYDVPDYASLEVLFQGPK-NH$_2$ (SEQ ID NO: 61) and Ac-AYPYDVPDYASLEVLFQ-GPOrn-NH$_2$ (SEQ ID NO: 62). In dry DMF containing excess (2–3 molar equivalents) DIEA, each of the peptides was mixed with two molar equivalents of iodoacetic anhydride for 10 min at room temperature under N$_2$ gas. The reaction was terminated by adding acetic acid. Solvent was removed by vacuum centrifugation, and the product was purified on a Sephasil_Peptide_C18_5µ_ST_4.6/100 column connected to AKTA purifier Amersham Pharmcia Biotech FPLC system (Uppsala, Sweden). Solvent A was 0.01% v/v TFA/H$_2$O, and solvent B was 0.01% v/v TFA/H$_2$O/90% acetonitrile. A flow rate of 0.8 ml/min was used, with the UV monitored at 280 nm. The gradient was from 0 to 50% B over 35 column volume. The fraction-collected peak was analyzed by MALDI MS (TofSpec 2E, Micromass) with α-cyano4-hydroxy-cinnamic acid as matrix and by ESI MS/MS (API 3, PE Sciex).

Example 6

Synthesis of Immobilized Peptide Encoded Tags (IPEPTags)

A pair of IPEPTags was synthesized from peptides with following sequences: Sepharose gel-CASASLEVLFQGPK-NH$_2$ (SEQ ID NO: 63) and Sepharose gel-CASASLEVLFQGPOrn-NH$_2$ (SEQ ID NO: 64). Pack two 10 ml empty columns with 2 ml of each gel-coupled peptide. Drain the storage buffer completely. Rinse the gel bed three times with 5 ml DMF. Add 2 ml DMF with 2 µmol iodoacetic anhydride and 1 µl DIEA into each column. Mix and react at room temperature for 15 min. Drain reagents completely and rinse the gel with 10× volume of buffer 50 mM tris (pH 8.5) and then store in the same buffer.

Example 7

Growth and Lysis of S. Cerevisiae

Strain BJ5460 was grown to mid log phase (O.D. 0.6) in YPD, centrifuged and washed 1× with buffer (1 M sorbitol, 10 mM KH2PO4, pH 7.5, 50 mM NaCl, 1 mM EDTA). Resuspended cells in buffer, added zymolase (3 mg per 100 OD), and incubate at 30° C. for 45 min. Cells were harvested by centrifugation, wash once and then solubilized in 8 M Urea, 50 mM Tris-HCl pH 8.5 and disrupted in the presence of glass beads on a mixer. The protein concentration was determined by the Bradford assay.

Example 8

APEPTag Analysis of Protein Mixtures

Protein mixtures were denatured and reduced in a buffer containing 8 M Urea, 10 mM tributyl phosphine and 50 mM Tris buffer (pH 8.5) for 30 min at 50° C. The side chains of cysteinyl residues were derivatized with about 5 fold molar excess of APEPTag. Tagged proteins were dialysis against 50 mM Tris buffer (pH 8.5) for 5 hours and then digested by trypsin overnight at 37° C. Trypsin activity was quenched with trypsin inhibitor and the peptide mixture bound to anti-HA affinity matrix for 2 hours at 4° C. The anti-HA resin with bound peptides was washed with 10 volume of equilibration buffer (20 mM Tris, pH 7.5; 0.1 m NaCl; 0.1 mM EDTA), 3×10 min. at 4° C. The bound peptides were cleaved from the matrix by incubation with PreScission protease overnight at 4° C.

For APEPTag quantitative strategy, two protein mixtures were denatured, reduced and then labeled differentially with either Lys-APEPTag or Orn-APEPTag. The two mixtures were combined after their dialysis. Protein denaturation, reduction, tagging, dialysis, digestion, affinity binding and were the same as described above.

Example 9

IPEPTag Analysis of Protein Mixtures

Protein mixtures were denatured and reduced in a buffer containing 8 M Urea, 10 mM tributyl phosphine and 50 mM Tris buffer (pH 8.5) for 30 min at 50° C. The side chains of cysteinyl residues were derivatized with about 10 fold molar excess of IPEPTag beads. Tagged proteins were digested first by Lys-C in 8M urea for 6 hours and then by trypsin in 2 M urea overnight at 37° C. The beads with bound peptides were washed with 10 volume of equilibration buffer (20 mM Tris, pH 7.5; 0.1 m NaCl; 0.1 mM EDTA), 3×10 min. at 4° C. The bound peptides were cleaved from the matrix by incubation with PreScission protease overnight at 4° C.

For IPEPTag quantitative strategy, two protein mixtures were denatured, reduced and then labeled differentially with either Lys-IPEPTag or Orn-IPEPTag beads. Protein denaturation, reduction, tagging, and digestion were the same as described above. Two batches of beads with bound peptides were combined after digestion, followed by wash and preScission cleavage as described above.

Example 10

Chromatography and Mass Spectrometry

Each sample was subjected to MudPIT analysis with modifications to the method described by Link et al. A quaternary HP 1100 HPLC pump (Hewlett-Packard, Palo Alto, Calif.) was interfaced with a Finnigan LCQ ion trap mass spectrometer (Finnigan MAT, San Jose, Calif.). The tip at the end of the 100×365 µm fused silica capillary (J & W Scientific, Folsom, Calif.) was pulled with a P-2000 laser (Sutter Instruments Co., Novato, Calif.). The fritless capillary was first packed with 10 cm of 5 µm Zorbax Eclipse XDB-C18 (Hewlett Packard, Palo Alto, Calif.) and then with 4 cm of 5 µm Partisphere SCX (Whatman, Clifton, N.J.). The column, was connected to a PEEK micro-cross as described elsewhere, in order to split the flow of the HPLC pump to an effective flow rate of 0.15–0.25 µL/min and supply a spray voltage of 1.8 W. The Zorbax 4.6×30 mm Eclipse XDB C18 column for the off-line fractionation was manufactured by Hewlett Packard, Palo Alto, Calif.

Each sample mixture was loaded onto separate microcolumn for the analysis. After loading the microcapillary column, the column was placed in-line with the system. A fully automated 7-step chromatography run was carried out on each sample. The four buffer solutions used for the chromatography were 5% ACN/0.5% acetic acid/0.02% HFBA (buffer A), 80% ACN//0.5% acetic acid/0.02% HFBA (buffer B), 250 mM ammonium acetate/5% ACN/0.5% acetic acid/0.02% HFBA (buffer C), and 1.5 M ammonium acetate/5% ACN/0.5% acetic acid/0.02% HFBA (buffer D). The first step of 80 min consisted of a 70 min gradient from 0 to 80% buffer B and a 10 min hold at 80% buffer B. The next 5 steps were 110 min each with the following profile: 5 min of 100% buffer A, 2 min of x% buffer C, 3 min of 100% buffer A, a 10 min gradient from 0 to 10% buffer B, and a 90 min gradient from 10 to 50% buffer B. The 2 min buffer C percentages (x) in steps 2–13 were as follows: 10, 30, 50, 70 and 100%. Step 7 is 5 min of 100% buffer A, 2 min of 100% buffer D, 3 min of 100% buffer A, a 10 min gradient from 0 to 10% buffer B, and a 90 min gradient from 10 to 100% buffer B, and a 10 min hold at 100% buffer B.

The mass spectrometer was operated in a four step cycle, where the 3 most intense ions were scanned in a MS/MS mode (3 µscans per scan). The scan range for the MS experiment was set to m/z 400–2000.

Example 11

Analysis of SEQUEST Data

A singly charged peptide must be tryptic and the cross-correlation score has to be higher than 1.9. Tryptic or partially tryptic peptides with a charge state +2 must have a cross-correlation score of at least 2.2. Peptides with cross-correlation scores (XCorr) above 3 were accepted regardless of their tryptic nature. Triply charged tryptic or partially tryptic peptides were accepted if their XCorr was above 3.75. If proteins were identified by less than 4 different peptide spectra, the existence of the protein was manually checked by at least one good spectrum. Proteins identified by more than 4 peptides were considered as valid identification. Spectra of good quality need to meet the following criteria. MS/MS spectra have to show fragment ions clearly above the noise level with continuity in the b and y ion series. Y-ions of a protein sequence should be intense. The highest and second best scoring amino acid sequence should differ in their cross-correlation score by 0.1 or more.

Results:

The following data were generated from the application of affinity peptide encoded tags (APEPTags) method on a mixture of six model proteins.

Qualitative analysis: 35 modified cysteine containing peptides were extracted.

In the following sequence, "C#" indicates a modified cysteine, and "M@" indicates an oxidized methionine.

```
ALBU_BOVIN - 35 69293
 1 K.CC#TESLVNR.R                              (SEQ ID
                                                NO:65)
 2 K.DAIPENLPPLTADFAEDKDVC#K.N                 (SEQ ID
                                                NO:66)
 3 K.EYEATLEECC#AK.D                           (SEQ ID
                                                NO:67)
 4 K.EYEATLEECC#AKDDPHACYSTVFDK.L              (SEQ ID
                                                NO:68)
 5 K.LFTFHADIC#TLPDTEK.Q                       (SEQ ID
                                                NO:69)
 6 K.LKEC#CDKPLLEK.S                           (SEQ ID
                                                NO:70)
 7 K.LKPDPNTLC#DEFK.A                          (SEQ ID
                                                NO:71)
 8 R.M@PC#TEDYLSLILNR.L                        (SEQ ID
                                                NO:72)
 9 R.MPC#TEDYLSLILNR.L                         (SEQ ID
                                                NO:73)
10 R.NEC#FLSHKDDSPDLPK.L                       (SEQ ID
                                                NO:74)
11 R.RPC#FSALTPDETYVPK.A                       (SEQ ID
                                                NO:75)
12 K.SHC#IAEVEK.D                              (SEQ ID
                                                NO:76)
13 K.SLHTLFGDELC#K.V                           (SEQ ID
                                                NO:77)
14 K.YIC#DNQDTISSK.L                           (SEQ ID
                                                NO:78)
15 K.YNGVFQECC#QAEDK.G                         (SEQ ID
                                                NO:79)
BGAL_ECOLI -
 1 R.AVVELHTADGTLIEAEAC#DVGFR.E                (SEQ ID
                                                NO:80)
 2 R.IGLNC#QLAQVAER.V                          (SEQ ID
                                                NO:81)
 3 D.PSRPVQYEGGGADTTATDIIC#PM@YAR.V            (SEQ ID
                                                NO:82)
 4 D.PSRPVQYEGGGADTTATDIIC#PMYAR.V             (SEQ ID
                                                NO:83)
 5 R.PVQYEGGGADTTATDIIC#PMYAR.V                (SEQ ID
                                                NO:84)
 6 K.SVDPSRPVQYEGGGADTTATDIIC#PM@YAR.V         (SEQ ID
                                                NO:85)
```

-continued

```
7 K.SVDPSRPVQYEGGGADTTATDIIC#PMYAR.V      (SEQ ID
                                          NO:86)
G3P_RABIT -
 1 K.IVSNASC#TTNCLAPLAK.V                 (SEQ ID
                                          NO:87)
 2 K.IVSNASCTTNC#LAPLAK.V                 (SEQ ID
                                          NO:88)
 3 R.VPTPNVSVVDLTC#R.L                    (SEQ ID
                                          NO:89)
LACB_BOVIN -
 1 R.LSFNPTQLEEQC#HI.-                    (SEQ ID
                                          NO:90)
LCA_BOVIN -
 1 K.DDQNPHSSNIC#NISCDK.F                 (SEQ ID
                                          NO:91)
 2 K.DDQNPHSSNICNISC#DK.F                 (SEQ ID
                                          NO:92)
 3 K.FLDDDLTDDIM@C#VK.K                   (SEQ ID
                                          NO:93)
 4 K.FLDDDLTDDIMC#VK.K                    (SEQ ID
```

-continued

```
                                          NO:94)
 5 K.LDQWLC#EK.L                          (SEQ ID
                                          NO:95)
 6 S.NICNISCDKFLDDDLTDDIMC#VK.K           (SEQ ID
                                          NO:96)
 7 H.SSNIC#NISCDK.F                       (SEQ ID
                                          NO:97)
OVAL_CHICK - 3 42750
 1 R.ADHPFLFC#IK.H                        (SEQ ID
                                          NO:98)
 2 R.YPILPEYLQC#VK.E                      (SEQ ID
                                          NO:99)
```

The following data were generated from immobilized peptide encoded tags applied to a whole cell extract from yeast. 142 unique proteins were identified.

```
Yeast protein extracts:

YAL003W EFB1 1 22627 0.00
  1 N.C#VVEDDKVSLDDLQQSIEEDEDHVQSTDIAAMQK.L   (SEQ ID NO: 100)
YAL005C SSA1 9 69767 0.00
  1 K.AVGIDLGTTYSC#VAH.F                      (SEQ ID NO: 101)
  2 K.AVGIDLGTTYSC#VAHFANDR.V                 (SEQ ID NO: 102)
  3 R.FEELC#ADLFR.S                           (SEQ ID NO: 103)
YAL038W CDC19 20 54545 0.00
  1 R.AEVSDVGNAILDGADC#VMLSGETAK.G            (SEQ ID NO: 104)
  2 V.GNAILDGADC#VMLSGETAK.G                  (SEQ ID NO: 105)
  3 R.NC#TPKPTSTTETVAASAVAAVFEQK.A            (SEQ ID NO: 106)
  4 K.PVIC#ATQMLESMTYNPR.P                    (SEQ ID NO: 107)
  5 K.SNLAGKPVIC#ATQMLESM@TYNPR.P             (SEQ ID NO: 108)
  6 K.SNLAGKPVIC#ATQNLESNTYNPR.P              (SEQ ID NO: 109)
  7 K.YRPNC#PIILVTR.C                         (SEQ ID NO: 110)
YBL024W - 1 77879 0.00
  1 R.LVYSTC#SLNPIENEAVVAEALR.K               (SEQ ID NO: 111)
YBL047C - 1 150783 0.00
  1 R.LPNQTLGEIWALC#DR.D                      (SEQ ID NO: 112)
YBL072C RPS8A 2 22490 0.00
  1 R.C#DGYILEGEELAFYLR.R                     (SEQ ID NO: 113)
YBL075C SSA3 2 70547 0.00
  1 R.AVGIDLGTTYSC#VAHFSNDR.V                 (SEQ ID NO: 114)
YBL087C RPL23A 4 i4473 0.00
  1 R.ISLGLPVGAIM@NC#ADNSGAR.N                (SEQ ID NO: 115)
  2 R.ISLGLPVGAIMNC#ADNSGAR.N                 (SEQ ID NO: 116)
  3 L.PVGAIMNC#ADNSGAR.N                      (SEQ ID NO: 117)
YBR025C - 4 44174 0.00
  1 R.C#PLGNPANYPFATIDPEEAR.V                 (SEQ ID NO: 118)
  2 K.LDLISFFTC#GPDEVR.E                      (SEQ ID NO: 119)
  3 K.PC#IYLINLSER.D                          (SEQ ID NO: 120)
  4 R.SVDSIYQVVR.C                            (SEQ ID NO: 121)
YBR031W RPL4A 5 39092 0.00
  1 R.SGQGAFGNMC#R.G                          (SEQ ID NO: 122)
YBR048W RPS11B 4 17749 0.00
  1 K.C#PFTGLVSIR.G                           (SEQ ID NO: 123)
  3 R.VQVGDIVTVGQC#R.P                        (SEQ ID NO: 124)
  4 R.VQVGDIVTVGQC#RPISK.T                    (SEQ ID NO: 125)
YBR118W TEF2 17 50033 0.00
  1 N.ATVIVLNHPGQISAGYSPVLDC#HTAH.I           (SEQ ID NO: 126)
  2 M.C#VEAFSEYPPLGR.F                        (SEQ ID NO: 127)
  3 F.NATVIVLNHPGQISAGYSPVLDC#HTAH.I          (SEQ ID NO: 128)
  4 K.NM@ITGTSQADC#AILIIAGGVGEFEAGISK.        (SEQ ID NO: 129)
  5 K.NMITGTSQADC#AILIIAGGVGEFEAGISK.D        (SEQ ID NO: 130)
  6 K.PMC#VEAFSEYPPLGR.F                      (SEQ ID NO: 131)
  7 V.PSKPMC#VEAFSEYPPLGR.F                   (SEQ ID NO: 132)
YBR127C VMA2 4 57749 0.00
  1 K.IPIFSASGLPHNEIAAQIC#R.Q                 (SEQ ID NO: 133)
YBR169C SSE2 1 77621 0.00
  1 K.GAAFIC#AIHSPTLR.V                       (SEQ ID NO: 134)
YBR249C ARO4 6 39749 0.00
```

-continued

| Yeast protein extracts: | |
|---|---|
| 1 K.GNEHC#FVILR.G | (SEQ ID NO: 135) |
| 2 K.NGTDGTLNVAVDAC#QAAAHSHHFM@GVTK.H | (SEQ ID NO: 136) |
| 3 K.NGTDGTLNVAVDAC#QAAAHSHHFMGVTK.H | (SEQ ID NO: 137) |
| 4 R.VLVIVGPC#SIHDLEAAQEYALR.L | (SEQ ID NO: 138) |
| 5 K.VNDVVC#EQIANGENAITGVMIESNINEGNQGIPAEGK.A | (SEQ ID NO: 139) |
| 6 K.YGVSITDAC#IGWETTEDVLR.K | (SEQ ID NO: 140) |

YBR263W SHM1 1 62862 0.00
1 K.EISQGC#GAYLMSDMAH.I (SEQ ID NO: 141)
YCL009C ILV6 1 33987 0.00
1 K.LVEPFGVLEC#AR.S (SEQ ID NO: 142)
YCL030C HIS4 1 87790 0.00
1 K.FHAAQLPTETLEVETQPGVLC#SR.F (SEQ ID NO: 143)
YDL014W NOP1 2 34465 0.00
1 R.DHC#IVVGR.Y (SEQ ID NO: 144)
2 R.MLIGMVDC#VFADVAQPDQAR.I (SEQ ID NO: 145)
YDL055C PSA1 3 39566 0.00
1 K.DNSPFFVLNSDVIC#EYPFK.E (SEQ ID NO: 146)
2 K.STIVGWNSTVGQWC#R.L (SEQ ID NO: 147)
3 R.SVVLC#NSTIK.N (SEQ ID NO: 148)
YDL061C RPS29B 1 6728 0.00
1 R.VC#SSHTGLVR.K (SEQ ID NO: 149)
YDL066W IDP1 1 48190 0.00
1 K.C#ATITPDEAR.V (SEQ ID NO: 150)
YDL097C RPN6 1 49774 0.00
1 R.SHFNALYDTLLESNLC#K.I (SEQ ID NO: 151)
YDL126C CDC48 2 91996 0.00
1 K.DTVLIVLIDDELEDGAC#R.I (SEQ ID NO: 152)
2 R.LGDLVTIHPC#PDIK.Y (SEQ ID NO: 153)
YDL131W LYS21 3 48594 0.00
1 R.DIENLVADAVEVNIPFNNPITGFC#AF.T (SEQ ID NO: 154)
2 R.VGIADTVGC#ANPR.Q (SEQ ID NO: 155)
YDL136W RPL35B 1 13910 0.00
1 K.SIAC#VLTVINEQQR.E (SEQ ID NO: 156)
YDL229W SSB1 10 66602 0.00
1 G.ERVNC#KENTLLGEFDLKNIPMMPAGEP.V (SEQ ID NO: 157)
2 R.TFTTC#ADNQTTVQFPVYQGER.V (SEQ ID NO: 158)
YDR002W - 1 22953 0.00
1 K.IC#ANHIIAPEYTLKPNVGSDR.S (SEQ ID NO: 159)
YDR035W ARO3 2 41070 0.00
1 R.IMIDC#SHGNSNK.D (SEQ ID NO: 160)
2 K.LPIAGEMLDTISPQFLSDC#FSLGAIGAR.T (SEQ ID NO: 161)
YDR037W KRS1 2 67959 0.00
1 K.LEC#PPPLTNAR.M (SEQ ID NO: 162)
YDR061W - 1 61191 0.00
1 K.YDSIEVSGGC#PIVIGLR.Y (SEQ ID NO: 163)
YDR091C - 1 66340 0.00
1 R.APESLLTGC#NR.F (SEQ ID NO: 164)
YDR127W ARO1 1 174755 0.00
1 R.ALILAALGEGQC#K.I (SEQ ID NO: 165)
YDR155C CPH1 5 17391 0.00
1 N.AGPNTNGSQFFITTVPC#PWLDGK.H (SEQ ID NO: 166)
2 M.ANAGPNTNGSQFFITTVPC#PWLDGK. (SEQ ID NO: 167)
3 R.PGLLSM@ANAGPNTNGSQFFITTVPC#PWLDGK.H (SEQ ID NO: 168)
YDR158W HOM2 1 39544 0.00
1 R.VAVSDGHTEC#ISLR.F (SEQ ID NO: 169)
YDR188W CCT6 2 59924 0.00
1 R.AAAAQDEITGDGTTTVVC#LVGELLR.Q (SEQ ID NO: 170)
2 R.NAITGATGIASNLLLC#DELLR.A (SEQ ID NO: 171)
YDR190C - 2 50453 0.00
1 K.VPFC#PLVGSELYSVEVK.K (SEQ ID NO: 172)
2 R.YALQLLAPC#GILAQTSNR.K (SEQ ID NO: 173)
YDR226W ADK1 1 24255 0.00
1 K.DELTNNPAC#K.N (SEQ ID NO: 174)
YDR321W ASP1 1 41395 0.00
1 K.SQNAAVNGSGIAC#QQR.S (SEQ ID NO: 175)
YDR353W TRR1 1 34238 0.00
1 R.NKPLAVIGGGDSAC#EEAQFLTK.Y (SEQ ID NO: 176)
YDR385W EFT2 10 93289 0.00
1 R.AEQLYEGPADDANC#IAIK.N (SEQ ID NO: 177)
2 K.IWC#FGPDGNGPNLVIDQTK.A (SEQ ID NO: 178)
3 R.VTDGALVVVDTIEGVC#VQTETVLR.Q (SEQ ID NO: 179)
YDR418W RPL12B 1 17823 0.00
1 K.EILGTAQSVGC#R.V (SEQ ID NO: 180)
YDR447C RPS17B 4 15803 0.00
1 R.LC#DEIATIQSK.R (SEQ ID NO: 181)
YDR487C RIB3 1 22568 0.00
1 R.GHTEAGVDLC#K.L (SEQ ID NO: 182)

-continued

| Yeast protein extracts: | |
|---|---|
| YDR502C SAM2 2 42256 0.00 | |
| 1 K.SLVAAGLC#K.R | (SEQ ID NO: 183) |
| 2 K.TC#NVLVAIEQQSPDIAQGLHYEK.S | (SEQ ID NO: 184) |
| YEL046C GLY1 1 42815 0.00 | |
| 1 R.THLMQPPYSILC#DYR.A | (SEQ ID NO: 185) |
| YEL047C - 2 50844 0.00 | |
| 1 R.LGGSSLLEC#VVFGR.T | (SEQ ID NO: 186) |
| YER007C-A - 1 20278 0.00 | |
| 1 K.FVLSGANIMC#PGLTSAGADLPPAPGYEK.G | (SEQ ID NO: 187) |
| 1 K.HYSKPDGPNNNVAVVC#SAR.S | (SEQ ID NO: 188) |
| YER055C HIS1 1 32266 0.00 | |
| 1 K.C#DLGITGVDQVR.E | (SEQ ID NO: 189) |
| YER091C MET6 2 85860 0.00 | |
| 1 K.GMLTGPITC#LR.W | (SEQ ID NO: 190) |
| YER107C GLE2 1 40523 0.00 | |
| 1 R.AQHESSSPVLC#TR.W | (SEQ ID NO: 191) |
| YBR133W GLC7 2 35907 0.00 | |
| 1 K.IC#GDIHGQYYDLLR.L | (SEQ ID NO: 192) |
| 2 K.IFC#MHGGLSPDLNSMEQIR.R | (SEQ ID NO: 193) |
| YER177W RPL23B 2 30091 0.00 | |
| 1 K.SEHQVELIC#SYR.S | (SEQ ID NO: 194) |
| YFL018C LPD1 1 54010 0.00 | |
| 1 K.AAQLGFNTAC#VEK.R | (SEQ ID NO: 195) |
| YFL039C ACT1 4 41690 0.00 | |
| 1 K.LC#YVALDFEQEMQTAAQSSSIEK.S | (SEQ ID NO: 196) |
| YFL045C SEC53 4 29063 0.00 | |
| 1 K.TYC#LQHVEK.D | (SEQ ID NO: 197) |
| YGL009C LEU1 4 85794 0.00 | |
| 1 R.EAEILVVTGDNFGC#GSSR.E | (SEQ ID NO: 198) |
| 2 K.HC#LVNGLDDIGITLQK.E | (SEQ ID NO: 199) |
| 3 R.VDC#TLATVDHNIPTESR.K | (SEQ ID NO: 200) |
| 4 K.VFIGSC#TNGR.I | (SEQ ID NO: 201) |
| YGL026C TRP5 3 76626 0.00 | |
| 1 R.FGDFGGQYVPEALHAC#LR.E | (SEQ ID NO: 202) |
| 2 K.LPDAVVAC#VGGGSNSTGMFSPFEHDTSVK.L | (SEQ ID NO: 203) |
| 3 R.LTEHC#QGAQIWLK.R | (SEQ ID NO: 204) |
| YGL087C MMS2 1 15545 0.00 | |
| 1 K.INLPC#VNPTTGEVQTDFHTLR.D | (SEQ ID NO: 205) |
| YGL105W ARC1 1 42084 0.00 | |
| 1 K.STAMVLC#GSNDDKVEFVEPPKDSK.A | (SEQ ID NO: 206) |
| YGL135W RPL1B 2 24486 0.00 | |
| 1 K.SC#GVDAMSVDDLK.K | (SEQ ID NO: 207) |
| 2 K.SC#GVDAMSVDDLKK.L | (SEQ ID NO: 208) |
| YGL147C RPL9A 4 21569 0.00 | |
| 1 K.DEIVLSGNSVEDVSQNAADLQQIC#R.V | (SEQ ID NO: 209) |
| 2 N.VKDEIVLSGNSVEDVSQNAADLQQIC#R.V | (SEQ ID NO: 210) |
| YGL148W ARO2 3 40838 0.00 | |
| 1 R.C#PDASVAGLMVK.E | (SEQ ID NO: 211) |
| 2 K.DSIGGVVTC#VVR.N | (SEQ ID NO: 212) |
| YGL157W - 1 38083 0.00 | |
| 1 K.DC#IVDTAAQMLEVQNEA. - | (SEQ ID NO: 213) |
| YGL202W ARO8 1 56178 0.00 | |
| 1 K.DYFPWDNLSVDSPKPPFPQGIGAPIDEQNC#IK.Y | (SEQ ID NO: 214) |
| 1 K.C#VHFQNSYYR.K | (SEQ ID NO: 215) |
| YGL245W - 1 82663 0.00 | |
| 1 K.YSAADVAC#WGALR.S | (SEQ ID NO: 216) |
| YGR192C TDH3 19 35747 0.00 | |
| 1 K.IVSNASCTTNC#LAPLAK.V | (SEQ ID NO: 217) |
| YGR204W ADE3 2 102205 0.00 | |
| 1 K.NGHPFFLPC#TPK.G | (SEQ ID NO: 218) |
| 2 R.SPVTVEDVGC#TGALTALLR.D | (SEQ ID NO: 219) |
| YGR234W YHB1 1 44646 0.00 | |
| 1 K.C#NPNRPIYWIQSSYDEK.T | (SEQ ID NO: 220) |
| YGR240C PFK1 2 107970 0.00 | |
| 1 R.QAAGNLISQGIDALVVC#GGDGSLTGADLFR.H | (SEQ ID NO: 221) |
| YGR254W ENO1 7 46816 0.00 | |
| 2 K.IGLDC#ASSEFFK.D | (SEQ ID NO: 222) |
| YGR285C ZUO1 3 49020 0.00 | |
| 1 R.AQYDSC#DFVADVPPPK.K | (SEQ ID NO: 223) |
| YHR019C DED81 2 62207 0.00 | |
| 2 K.YGTC#PHGGYGIGTER.I | (SEQ ID NO: 224) |
| YHR025W THR1 1 38712 0.00 | |
| 1 K.C#IAIIPQFELSTADSR.G | (SEQ ID NO: 225) |
| YHR030C SLT2 1 55636 0.00 | |
| 1 R.ITVDEALEHPYLSIWHDPADEPVC#SEK.F | (SEQ ID NO: 226) |
| YHR064C PDR13 1 62186 0.00 | |
| 1 K.C#ANGAPAVEVDGK.V | (SEQ ID NO: 227) |

-continued

| Yeast protein extracts: | |
|---|---|
| YHR208W BAT1 3 43596 0.00 | |
| 1 K.EIGWNNEDIHVPLLPGEQC#GALTK.Q | (SEQ ID NO: 228) |
| 2 R.IC#LPTFESEELIK.L | (SEQ ID NO: 229) |
| 3 K.LGANYAPC#ILPQLQAAK.R | (SEQ ID NO: 230) |
| YHR216W - 1 56530 0.00 | |
| 1 L.LGGIGFIHHNC#TPEDQADMVR.R | (SEQ ID NO: 231) |
| YIL022W TIM44 1 48854 0.00 | |
| 1 K.LLAPQDIPVLVVGC#R.A | (SEQ ID NO: 232) |
| YIL041W - 1 36670 0.00 | |
| 1 K.VALNSSEC#LNK.M | (SEQ ID NO: 233) |
| YIL094C LYS12 1 40069 0.00 | |
| 1 K.EQC#QGALFGAVQSPTTK.V | (SEQ ID NO: 234) |
| YIR006C PAN1 1 160267 0.00 | |
| 1 R.SIVTNGSNTVSGANC#R.K | (SEQ ID NO: 235) |
| YIR034C LYS1 1 41465 0.00 | |
| 1 R.GGPFDEIPQADIFINC#IYLSK.P | (SEQ ID NO: 236) |
| YJL045W - 1 69382 0.00 | |
| 1 K.YRNVIAHTLDENEC#APVPPAVR.S | (SEQ ID NO: 237) |
| YJL130C URA2 1 245126 0.00 | |
| 1 R.GHNIPC#TSTISGR.C | (SEQ ID NO: 238) |
| YJL138C TIF2 2 44697 0.00 | |
| 1 K.VHAC#IGGTSFVEDAEGLR.D | (SEQ ID NO: 239) |
| YJL200C - 2 86583 0.00 | |
| 1 K.DLPSSIATNQEVFDFLESC#AK.R | (SEQ ID NO: 240) |
| YJR016C ILV3 2 62861 0.00 | |
| 1 R.EIIADSFETIMMAQHYDANIAIPSC#DK.N | (SEQ ID NO: 241) |
| 2 K.LVSNASNGC#VLDA.- | (SEQ ID NO: 242) |
| YJR109C CPA2 1 123915 0.00 | |
| 1 R.HLGVIGEC#NVQYALQPDGLDYR.V | (SEQ ID NO: 243) |
| YJR148W BAT2 2 41625 0.00 | |
| 1 R.IC#LPTFDPEELITLIGK.L | (SEQ ID NO: 244) |
| 2 K.LGANYAPC#VLPQLQAASR.G | (SEQ ID NO: 245) |
| YKL006W RPL14A 1 15167 0.00 | |
| 1 K.WAAAAVC#EK.W | (SEQ ID NO: 246) |
| YKL060C FBA1 6 39621 0.00 | |
| 1 H.MLDLSEETDEENISTC#VK.Y | (SEQ ID NO: 247) |
| 2 R.SIAPAYGIPVVLHSDHC#AK.K | (SEQ ID NO: 248) |
| 3 K.VNLDTDC#QYAYLTGIR.D | (SEQ ID NO: 249) |
| YKL182W FAS1 2 228691 0.00 | |
| 1 R.GYTC#QFVDMVLPNTALK.T | (SEQ ID NO: 250) |
| 2 R.TC#ILHGPVAAQFTK.V | (SEQ ID NO: 251) |
| YKL216W URA1 2 34801 0.00 | |
| 1 K.DAFEHLLC#GASMLQIGTELQK.E | (SEQ ID NO: 252) |
| 2 K.IQDSEFNGITELNLSC#PNVPGKPQVAYDFDLTK.E | (SEQ ID NO: 253) |
| YLL026W HSP104 1 102035 0.00 | |
| 1 R.LPDSALDLVDISC#AGVAVAR.D | (SEQ ID NO: 254) |
| YLR027C AAT2 1 47793 0.00 | |
| 1 K.LSTVSPVFVC#QSFAK.N | (SEQ ID NO: 255) |
| 2 K.NPVILADACC#SR.H | (SEQ ID NO: 256) |
| YLR058C SHM2 1 52218 0.00 | |
| 1 R.M@EILC#QQR.A | (SEQ ID NO: 257) |
| YLR075W RPL10 3 25361 0.00 | |
| 1 K.MLSC#AGADR.L | (SEQ ID NO: 258) |
| YLR109W - 2 19115 0.00 | |
| 1 K.FQYIAISQSDADSESC#K.M | (SEQ ID NO: 259) |
| YLR153C ACS2 1 75492 0.00 | |
| 1 R.TYLPPVSC#DAEDPLFLLYTSGSTGSPK.G | (SEQ ID NO: 260) |
| YLR249W YEF3 13 115945 0.00 | |
| 1 R.AIANGQVDGFPTQEEC#R.T | (SEQ ID NO: 261) |
| 2 R.FIPSLIQC#IADPTEVPETVHLLGATTF.V | (SEQ ID NO: 262) |
| 3 H.IANQSNLSPSVEPYIVQLVPAIC#TNAGNK.D | (SEQ ID NO: 263) |
| 5 R.KEIEEHC#SMLGLDPEIVSHSR.I | (SEQ ID NO: 264) |
| 6 K.NTYEYEC#SFLLGENIGMK.S | (SEQ ID NO: 265) |
| 8 K.PQITDINFQC#SLSSR.I | (SEQ ID NO: 266) |
| 10 K.STLINVLTGELLPTSGEVYTHENC#R.I | (SEQ ID NO: 267) |
| 13 K.VTNMEFQYPGTSKPQITDINFQC#SLSSR.I | (SEQ ID NO: 268) |
| YLR259C HSP60 3 60752 0.00 | |
| 1 K.NVAAGC#NPM@DLR.R | (SEQ ID NO: 269) |
| 2 K.NVAAGC#NPMDLR.R | (SEQ ID NO: 270) |
| YLR304C ACO1 1 85368 0.00 | |
| 1 R VGLIGSC#TNSSYEDMSR.S | (SEQ ID NO: 271) |
| YLR355C ILV5 5 44368 0.00 | |
| 1 K.YGMDYMYDAC#STTAR.R | (SEQ ID NO: 272) |
| YLR441C RPS1A 3 28743 0.00 | |
| 1 R.VVEVC#LADLQGSEDHSFR.K | (SEQ ID NO: 273) |
| YLR447C VMA6 1 39791 0.00 | |
| 1 R.NITWIAEC#IAQNQR.E | (SEQ ID NO: 274) |

```
                  -continued
            Yeast protein extracts:

YML007W YAP1 1 72533 0.00
  1 S.EFC#SKMNQVCGTRQCPIPKKPISALDK.E         (SEQ ID NO: 275)
YML008C ERG6 2 43431 0.00
  1 R.GDLVLDVGC#GVGGPAR.E                    (SEQ ID NO: 276)
  2 K.VYAIEATC#HAPK.L                        (SEQ ID NO: 277)
YML028W TSA1 3 21590 0.00
  1 R.LVEAFQWTDKNGTVLPC#NWTPGAATIKPTVEDSK.E  (SEQ ID NO: 278)
  2 K.NGTVLPC#NWTPGAATIKPTVEDSK.E            (SEQ ID NO: 279)
YML085C TUB1 1 49800 0.00
  1 K.IGIC#YEPPTATPNSQLATVDR.A               (SEQ ID NO: 280)
YML126C HMGS 2 55014 0.00
  1 R.VGLFSYGSGLAASLYSC#K.I                  (SEQ ID NO: 281)
YMR079W SEC14 1 34901 0.00
  1 R.AAGHLVETSC#TIMDLK.G                    (SEQ ID NO: 282)
YMR116C BEL1 4 34805 0.00
  1 Q.C#LATLLGHNDWVSQVR.V                    (SEQ ID NO: 283)
  2 K.GQC#LATLLGHNDWVSQVR.V                  (SEQ ID NO: 284)
YMR120C ADE17 1 65263 0.00
  1 K.YTQSNSVC#YAR.N                         (SEQ ID NO: 285)
YMR173W-A - 1 43890 0.00
  1 K.C#PHLEIVNLSDNAFGLR.T                   (SEQ ID NO: 286)
YMR260C TIF11 1 17435 0.00
  1 R.VEASC#FDGNKR.M                         (SEQ ID NO: 287)
YMR315W - 1 38216 0.00
  1 K.IAESTPLPVGVAENWLYLPC#IK.I              (SEQ ID NO: 288)
Y:NL104C LEU4 1 68409 0.00
  1 R.GC#GVAATELGMLAGADR.V                   (SEQ ID NO: 289)
YNL134C - 1 41164 0.00
  1 K.IGPQGALLGC#DAAGQIVK.L                  (SEQ ID NO: 290)
YNL178W RPS3 3 26503 0.00
  2 K.GC#EVVVSGK.L                           (SEQ ID NO: 291)
YNL220W ADE12 2 48279 0.00
  1 R.C#AGGNNAGHTIVVDGVK.Y                   (SEQ ID NO: 292)
  2 R.C#GWLDLVVLK.Y                          (SEQ ID NO: 293)
YNL244C SUI1 1 12312 0.00
  1 K.VC#EFMISQLGLQK.K                       (SEQ ID NO: 294)
YNL301C RPL18B 6 20563 0.00
  1 K.AGGEC#ITLDQLAVR.A                      (SEQ ID NO: 295)
YNR050C LYS9 6 48918 0.00
  1 Y.C#GGLPAPEDSDNPLGYK.F                   (SEQ ID NO: 296)
  2 R.GNALDTLC#AR.L                          (SEQ ID NO: 297)
  3 F.LSYC#GGLPAPEDSDNPLGYK.F                (SEQ ID NO: 298)
  4 K.SFLSYC#GGLPAPEDSDNPLGYK.F              (SEQ ID NO: 299)
YOL086C ADH1 5 36849 0.00
  2 Y.ATADAVQAAHIPQGTDLAQVAPILC#AGITVYK.A    (SEQ ID NO: 300)
YOL143C RIB4 1 18556 0.00
  1 K.VDMPVIFGLLTC#MTEEQALAR.A               (SEQ ID NO: 301)
YOR007C SGT2 1 37218 0.00
  1 K.EISEDGADSLNVAMDC#ISEAFGFER.E           (SEQ ID NO: 302)
YOR122C PFY1 1
  1 R.HDAEGVVC#VR.T                          (SEQ ID NO: 303)
YOR187W - 1
  1 R.ELLNEYGFDGDNAPIIMGSALC#ALEGR.Q         (SEQ ID NO: 304)
YOR204W DED1 2
  1 R.DLMAC#AQTGSGK.T                        (SEQ ID NO: 305)
YOR229W WTM2 1
  1 R.FFNNHLFASC#SDDNILR.F                   (SEQ ID NO: 306)
YOR261C RPN8 1
  1 R.C#VGVILGDANSSTIR.V                     (SEQ ID NO: 307)
YPL028W ERG10 2
  1 K.VNVYGGAVALGHPLGC#SGAR.V                (SEQ ID NO: 308)
YPL061W ALD6 6
  1 K.IAPALAMGNVC#ILK.P                      (SEQ ID NO: 309)
  2 K.PAAVTPLNALYFASLC#K.K                   (SEQ ID NO: 310)
YPL117C IDI1 1
  1 K.IIC#ENYLFNWWEQLDDLSEVENDR.Q            (SEQ ID NO: 311)

Totals: #Unique Proteins = 142
        #Unique Peptides = 218
```

CONCLUSION

Thus, it will be appreciated that the compounds and methods described herein are used to identify proteins using mass spectrometry.

One skilled in the art would readily appreciate that the present invention is well adapted to carry out the objects and obtain the ends and advantages mentioned, as well as those inherent therein. The molecular complexes and the methods, procedures, molecules, and specific compounds described herein are presently representative of preferred embodiments and are exemplary and are not intended as limitations on the scope of the invention. Changes therein and other uses will occur to those skilled in the art which are encompassed within the spirit of the invention and are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that the use of such terms and expressions indicates the exclusion of equivalents of the features shown and described or portions thereof. It is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

What is claimed is:

1. A compound selected from the group consisting of Acyl-NH-CASENLYFQG-Lys-ε-iodoacetamide (SEQ ID NO:41), Acyl-NH-CASENLYFQG-Orn-δ-iodoacetamide (SEQ ID NO:42), Acyl-NH-CASENLYFQGP-Lys-ε-iodoacetamide (SEQ ID NO:43), and Acyl-NH-CASENLYFQGP-Orn-δ-iodoacetamide (SEQ ID NO:44).

2. A compound selected from the group consisting of: Acyl-CH$_2$CH$_2$CH$_2$—O-Ph-CH$_2$—G—NH—C(O)—CH$_2$I, Acyl-CH$_2$CH$_2$CH$_2$—O-Ph-CH$_2$—A—NH—C(O)—CH$_2$I, Acyl-CH$_2$CH$_2$CH$_2$—O-Ph-CH$_2$-γ-aminobutyric acid-NH—C(O)—CH$_2$I, and Acyl-CH$_2$CH$_2$CH$_2$—O-Ph-CH$_2$—V—NH—C(O)—CH$_2$I, where Ph is

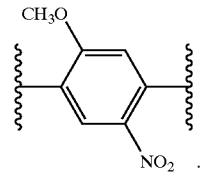

* * * * *

SEQUENCE LISTING

<160> NUMBER OF SEQ ID NOS: 311

<210> SEQ ID NO 1
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 1

Glu Asn Leu Tyr Phe Gln Gly
 1               5

<210> SEQ ID NO 2
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 2

Ala Tyr Pro Tyr Asp Val Pro Asp Tyr Ala Ser Glu Asn Leu Tyr Phe
 1               5                  10                  15

Gln Gly Lys

<210> SEQ ID NO 3
<211> LENGTH: 20
<212> TYPE: PRT
<213> ORGANISM: Artificial Sequence
<220> FEATURE:
<223> OTHER INFORMATION: Synthesized Peptide

<400> SEQUENCE: 3

Ala Tyr Pro Tyr Asp Val Pro Asp Tyr Ala Ser Glu Asn Leu Tyr Phe
 1               5                  10                  15

Gln Gly Gly Lys
            20

<210> SEQ ID NO 4
<211> LENGTH: 20

```
<212> TYPE: PRT
<213> ORGANISM: Artificial Sequence
<220> FEATURE:
<223> OTHER INFORMATION: Synthesized Peptide

<400> SEQUENCE: 4

Ala Tyr Pro Tyr Asp Val Pro Asp Tyr Ala Ser Glu Asn Leu Tyr Phe
 1               5                  10                  15

Gln Gly Ala Lys
         20

<210> SEQ ID NO 5
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 5

Ala Tyr Pro Tyr Asp Val Pro Asp Tyr Ala Ser Glu Asn Leu Tyr Phe
 1               5                  10                  15

Gln Gly Lys

<210> SEQ ID NO 6
<211> LENGTH: 20
<212> TYPE: PRT
<213> ORGANISM: Artificial Sequence
<220> FEATURE:
<223> OTHER INFORMATION: Synthesized Peptide

<400> SEQUENCE: 6

Ala Tyr Pro Tyr Asp Val Pro Asp Tyr Ala Ser Glu Asn Leu Tyr Phe
 1               5                  10                  15

Gln Gly Val Lys
         20

<210> SEQ ID NO 7
<211> LENGTH: 18
<212> TYPE: PRT
<213> ORGANISM: Artificial Sequence
<220> FEATURE:
<223> OTHER INFORMATION: Synthesized Peptide

<400> SEQUENCE: 7

Ala Tyr Pro Tyr Asp Val Pro Asp Tyr Ala Ser Glu Asn Leu Tyr Phe
 1               5                  10                  15

Gln Gly

<210> SEQ ID NO 8
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 8

Ala Tyr Pro Tyr Asp Val Pro Asp Tyr Ala Ser Glu Asn Leu Tyr Phe
 1               5                  10                  15

Gln Gly Gly

<210> SEQ ID NO 9
<211> LENGTH: 19
<212> TYPE: PRT
<213> ORGANISM: Artificial Sequence
```

<220> FEATURE:
<223> OTHER INFORMATION: Synthesized Peptide

<400> SEQUENCE: 9

Ala Tyr Pro Tyr Asp Val Pro Asp Tyr Ala Ser Glu Asn Leu Tyr Phe
 1               5                  10                  15

Gln Gly Ala

<210> SEQ ID NO 10
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 10

Ala Tyr Pro Tyr Asp Val Pro Asp Tyr Ala Ser Glu Asn Leu Tyr Phe
 1               5                  10                  15

Gln Gly Ala

<210> SEQ ID NO 11
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 11

Ala Tyr Pro Tyr Asp Val Pro Asp Tyr Ala Ser Glu Asn Leu Tyr Phe
 1               5                  10                  15

Gln Gly Val

<210> SEQ ID NO 12
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 12

Ala Tyr Pro Tyr Asp Val Pro Asp Tyr Ala Ser Glu Asn Leu Tyr Phe
 1               5                  10                  15

Gln Gly Arg

<210> SEQ ID NO 13
<211> LENGTH: 20
<212> TYPE: PRT
<213> ORGANISM: Artificial Sequence
<220> FEATURE:
<223> OTHER INFORMATION: Synthesized Peptide

<400> SEQUENCE: 13

Ala Tyr Pro Tyr Asp Val Pro Asp Tyr Ala Ser Glu Asn Leu Tyr Phe
 1               5                  10                  15

Gln Gly Gly Arg
            20

<210> SEQ ID NO 14
<211> LENGTH: 20
<212> TYPE: PRT
<213> ORGANISM: Artificial Sequence
<220> FEATURE:
<223> OTHER INFORMATION: Synthesized Peptide

```
<400> SEQUENCE: 14

Ala Tyr Pro Tyr Asp Val Pro Asp Tyr Ala Ser Glu Asn Leu Tyr Phe
 1               5                  10                  15

Gln Gly Ala Arg
            20

<210> SEQ ID NO 15
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 15

Ala Tyr Pro Tyr Asp Val Pro Asp Tyr Ala Ser Glu Asn Leu Tyr Phe
 1               5                  10                  15

Gln Gly Arg

<210> SEQ ID NO 16
<211> LENGTH: 20
<212> TYPE: PRT
<213> ORGANISM: Artificial Sequence
<220> FEATURE:
<223> OTHER INFORMATION: Synthesized Peptide

<400> SEQUENCE: 16

Ala Tyr Pro Tyr Asp Val Pro Asp Tyr Ala Ser Glu Asn Leu Tyr Phe
 1               5                  10                  15

Gln Gly Val Arg
            20

<210> SEQ ID NO 17
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 17

Ala Tyr Pro Tyr Asp Val Pro Asp Tyr Ala Ser Glu Asn Leu Tyr Phe
 1               5                  10                  15

Gln Gly Lys

<210> SEQ ID NO 18
<211> LENGTH: 20
<212> TYPE: PRT
<213> ORGANISM: Artificial Sequence
<220> FEATURE:
<223> OTHER INFORMATION: Synthesized Peptide

<400> SEQUENCE: 18

Ala Tyr Pro Tyr Asp Val Pro Asp Tyr Ala Ser Glu Asn Leu Tyr Phe
 1               5                  10                  15

Gln Gly Gly Lys
            20

<210> SEQ ID NO 19
<211> LENGTH: 20
<212> TYPE: PRT
<213> ORGANISM: Artificial Sequence
<220> FEATURE:
<223> OTHER INFORMATION: Synthesized Peptide

<400> SEQUENCE: 19
```

Ala Tyr Pro Tyr Asp Val Pro Asp Tyr Ala Ser Glu Asn Leu Tyr Phe
1               5                   10                  15

Gln Gly Ala Lys
            20

<210> SEQ ID NO 20
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 20

Ala Tyr Pro Tyr Asp Val Pro Asp Tyr Ala Ser Glu Asn Leu Tyr Phe
1               5                   10                  15

Gln Gly Lys

<210> SEQ ID NO 21
<211> LENGTH: 20
<212> TYPE: PRT
<213> ORGANISM: Artificial Sequence
<220> FEATURE:
<223> OTHER INFORMATION: Synthesized Peptide

<400> SEQUENCE: 21

Ala Tyr Pro Tyr Asp Val Pro Asp Tyr Ala Ser Glu Asn Leu Tyr Phe
1               5                   10                  15

Gln Gly Val Lys
            20

<210> SEQ ID NO 22
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 22

Ala Tyr Pro Tyr Asp Val Pro Asp Tyr Ala Ser Glu Asn Leu Tyr Phe
1               5                   10                  15

Gln Gly Arg

<210> SEQ ID NO 23
<211> LENGTH: 20
<212> TYPE: PRT
<213> ORGANISM: Artificial Sequence
<220> FEATURE:
<223> OTHER INFORMATION: Synthesized Peptide

<400> SEQUENCE: 23

Ala Tyr Pro Tyr Asp Val Pro Asp Tyr Ala Ser Glu Asn Leu Tyr Phe
1               5                   10                  15

Gln Gly Gly Arg
            20

<210> SEQ ID NO 24
<211> LENGTH: 20
<212> TYPE: PRT
<213> ORGANISM: Artificial Sequence
<220> FEATURE:
<223> OTHER INFORMATION: Synthesized Peptide

<400> SEQUENCE: 24

```
Ala Tyr Pro Tyr Asp Val Pro Asp Tyr Ala Ser Glu Asn Leu Tyr Phe
 1               5                  10                  15

Gln Gly Ala Arg
            20

<210> SEQ ID NO 25
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 25

Ala Tyr Pro Tyr Asp Val Pro Asp Tyr Ala Ser Glu Asn Leu Tyr Phe
 1               5                  10                  15

Gln Gly Arg

<210> SEQ ID NO 26
<211> LENGTH: 20
<212> TYPE: PRT
<213> ORGANISM: Artificial Sequence
<220> FEATURE:
<223> OTHER INFORMATION: Synthesized Peptide

<400> SEQUENCE: 26

Ala Tyr Pro Tyr Asp Val Pro Asp Tyr Ala Ser Glu Asn Leu Tyr Phe
 1               5                  10                  15

Gln Gly Val Arg
            20

<210> SEQ ID NO 27
<211> LENGTH: 18
<212> TYPE: PRT
<213> ORGANISM: Artificial Sequence
<220> FEATURE:
<223> OTHER INFORMATION: Synthesized Peptide

<400> SEQUENCE: 27

Ala Tyr Pro Tyr Asp Val Pro Asp Tyr Ala Ser Glu Asn Leu Tyr Phe
 1               5                  10                  15

Gln Gly

<210> SEQ ID NO 28
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 28

Ala Tyr Pro Tyr Asp Val Pro Asp Tyr Ala Ser Glu Asn Leu Tyr Phe
 1               5                  10                  15

Gln Gly Gly

<210> SEQ ID NO 29
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 29

Ala Tyr Pro Tyr Asp Val Pro Asp Tyr Ala Ser Glu Asn Leu Tyr Phe
 1               5                  10                  15
```

Gln Gly Ala

<210> SEQ ID NO 30
<211> LENGTH: 18
<212> TYPE: PRT
<213> ORGANISM: Artificial Sequence
<220> FEATURE:
<223> OTHER INFORMATION: Synthesized Peptide

<400> SEQUENCE: 30

Ala Tyr Pro Tyr Asp Val Pro Asp Tyr Ala Ser Glu Asn Leu Tyr Phe
 1               5                  10                  15

Gln Gly

<210> SEQ ID NO 31
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 31

Ala Tyr Pro Tyr Asp Val Pro Asp Tyr Ala Ser Glu Asn Leu Tyr Phe
 1               5                  10                  15

Gln Gly Val

<210> SEQ ID NO 32
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 32

Ala Tyr Pro Tyr Asp Val Pro Asp Tyr Ala Ser Glu Asn Leu Tyr Pro
 1               5                  10                  15

Gln Gly Lys

<210> SEQ ID NO 33
<211> LENGTH: 18
<212> TYPE: PRT
<213> ORGANISM: Artificial Sequence
<220> FEATURE:
<223> OTHER INFORMATION: Synthesized Peptide

<400> SEQUENCE: 33

Ala Tyr Pro Tyr Asp Val Pro Asp Tyr Ala Ser Glu Asn Leu Tyr Pro
 1               5                  10                  15

Gln Gly

<210> SEQ ID NO 34
<211> LENGTH: 18
<212> TYPE: PRT
<213> ORGANISM: Artificial Sequence
<220> FEATURE:
<223> OTHER INFORMATION: Synthesized Peptide

<400> SEQUENCE: 34

Ala Tyr Pro Tyr Asp Val Pro Asp Tyr Ala Ser Glu Asn Leu Tyr Pro
 1               5                  10                  15

Gln Gly

<210> SEQ ID NO 35
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 35

Ala Tyr Pro Tyr Asp Val Pro Asp Tyr Ala Ser Glu Asn Leu Tyr Pro
 1               5                  10                  15

Gln Gly Lys

<210> SEQ ID NO 36
<211> LENGTH: 16
<212> TYPE: PRT
<213> ORGANISM: Artificial Sequence
<220> FEATURE:
<223> OTHER INFORMATION: Synthesized Peptide

<400> SEQUENCE: 36

Tyr Pro Tyr Asp Val Pro Asp Tyr Ala Glu Asn Leu Tyr Phe Gln Gly
 1               5                  10                  15

<210> SEQ ID NO 37
<211> LENGTH: 16
<212> TYPE: PRT
<213> ORGANISM: Artificial Sequence
<220> FEATURE:
<223> OTHER INFORMATION: Synthesized Peptide

<400> SEQUENCE: 37

Tyr Pro Tyr Asp Val Pro Asp Tyr Ala Glu Asn Leu Tyr Phe Gln Gly
 1               5                  10                  15

<210> SEQ ID NO 38
<211> LENGTH: 9
<212> TYPE: PRT
<213> ORGANISM: Artificial Sequence
<220> FEATURE:
<223> OTHER INFORMATION: Synthesized Peptide

<400> SEQUENCE: 38

Tyr Pro Tyr Asp Val Pro Asp Tyr Ala
 1               5

<210> SEQ ID NO 39
<211> LENGTH: 19
<212> TYPE: PRT
<213> ORGANISM: Artificial Sequence
<220> FEATURE:
<223> OTHER INFORMATION: Synthesized Peptide

<400> SEQUENCE: 39

Ala Tyr Pro Tyr Asp Val Pro Asp Tyr Ala Ser Glu Asn Leu Tyr Phe
 1               5                  10                  15

Gln Gly Lys

<210> SEQ ID NO 40
<211> LENGTH: 19
<212> TYPE: PRT
<213> ORGANISM: Artificial Sequence
<220> FEATURE:
<221> NAME/KEY: VARIANT
<222> LOCATION: 19
<223> OTHER INFORMATION: Xaa = Ornithine
<220> FEATURE:
<223> OTHER INFORMATION: Synthesized Peptide

```
<400> SEQUENCE: 40

Ala Tyr Pro Tyr Asp Val Pro Asp Tyr Ala Ser Glu Asn Leu Tyr Phe
 1               5                  10                  15

Gln Gly Xaa

<210> SEQ ID NO 41
<211> LENGTH: 11
<212> TYPE: PRT
<213> ORGANISM: Artificial Sequence
<220> FEATURE:
<223> OTHER INFORMATION: Synthesized Peptide

<400> SEQUENCE: 41

Cys Ala Ser Glu Asn Leu Tyr Phe Gln Gly Lys
 1               5                  10

<210> SEQ ID NO 42
<211> LENGTH: 11
<212> TYPE: PRT
<213> ORGANISM: Artificial Sequence
<220> FEATURE:
<223> OTHER INFORMATION: Synthesized Peptide
<220> FEATURE:
<221> NAME/KEY: VARIANT
<222> LOCATION: 11
<223> OTHER INFORMATION: Xaa = Orinithine

<400> SEQUENCE: 42

Cys Ala Ser Glu Asn Leu Tyr Phe Gln Gly Xaa
 1               5                  10

<210> SEQ ID NO 43
<211> LENGTH: 12
<212> TYPE: PRT
<213> ORGANISM: Artificial Sequence
<220> FEATURE:
<223> OTHER INFORMATION: Synthesized Peptide

<400> SEQUENCE: 43

Cys Ala Ser Glu Asn Leu Tyr Phe Gln Gly Pro Lys
 1               5                  10

<210> SEQ ID NO 44
<211> LENGTH: 12
<212> TYPE: PRT
<213> ORGANISM: Artificial Sequence
<220> FEATURE:
<223> OTHER INFORMATION: Synthesized Peptide
<220> FEATURE:
<221> NAME/KEY: VARIANT
<222> LOCATION: 12
<223> OTHER INFORMATION: Xaa = Ornithine

<400> SEQUENCE: 44

Cys Ala Ser Glu Asn Leu Tyr Phe Gln Gly Pro Xaa
 1               5                  10

<210> SEQ ID NO 45
<211> LENGTH: 607
<212> TYPE: PRT
<213> ORGANISM: bovine serum albumin

<400> SEQUENCE: 45

Met Lys Trp Val Thr Phe Ile Ser Leu Leu Leu Leu Phe Ser Ser Ala
 1               5                  10                  15
```

```
Tyr Ser Arg Gly Val Phe Arg Arg Asp Thr His Lys Ser Glu Ile Ala
         20                  25                  30

His Arg Phe Lys Asp Leu Gly Glu Glu His Phe Lys Gly Leu Val Leu
         35                  40                  45

Ile Ala Phe Ser Gln Tyr Leu Gln Gln Cys Pro Phe Asp Glu His Val
 50                  55                  60

Lys Leu Val Asn Glu Leu Thr Glu Phe Ala Lys Thr Cys Val Ala Asp
 65                  70                  75                  80

Glu Ser His Ala Gly Cys Glu Lys Ser Leu His Thr Leu Phe Gly Asp
             85                  90                  95

Glu Leu Cys Lys Val Ala Ser Leu Arg Glu Thr Tyr Gly Asp Met Ala
         100                 105                 110

Asp Cys Cys Glu Lys Gln Glu Pro Glu Arg Asn Glu Cys Phe Leu Ser
         115                 120                 125

His Lys Asp Asp Ser Pro Asp Leu Pro Lys Leu Lys Pro Asp Pro Asn
130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
             165                 170                 175

Leu Leu Tyr Tyr Ala Asn Lys Tyr Asn Gly Val Phe Gln Glu Cys Cys
         180                 185                 190

Gln Ala Glu Asp Lys Gly Ala Cys Leu Leu Pro Lys Ile Glu Thr Met
         195                 200                 205

Arg Glu Lys Val Leu Ala Ser Ser Ala Arg Gln Arg Leu Arg Cys Ala
         210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
             245                 250                 255

Leu Val Thr Asp Leu Thr Lys Val His Lys Glu Cys Cys His Gly Asp
         260                 265                 270

Leu Leu Glu Cys Ala Asp Asp Arg Ala Asp Leu Ala Lys Tyr Ile Cys
         275                 280                 285

Asp Asn Gln Asp Thr Ile Ser Ser Lys Leu Lys Glu Cys Cys Asp Lys
290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
             325                 330                 335

Asp Val Cys Lys Asn Tyr Gln Glu Ala Lys Asp Ala Phe Leu Gly Ser
         340                 345                 350

Phe Leu Tyr Glu Tyr Ser Arg Arg His Pro Glu Tyr Ala Val Ser Val
         355                 360                 365

Leu Leu Arg Leu Ala Lys Glu Tyr Glu Ala Thr Leu Glu Glu Cys Cys
         370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
             405                 410                 415

Gln Phe Glu Lys Leu Gly Glu Tyr Gly Phe Gln Asn Ala Leu Ile Val
         420                 425                 430

Arg Tyr Thr Arg Lys Val Pro Gln Val Ser Thr Pro Thr Leu Val Glu
```

```
                435                 440                 445
Val Ser Arg Ser Leu Gly Lys Val Gly Thr Arg Cys Cys Thr Lys Pro
    450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
            500                 505                 510

Ala Leu Thr Pro Asp Glu Thr Tyr Val Pro Lys Ala Phe Asp Glu Lys
        515                 520                 525

Leu Phe Thr Phe His Ala Asp Ile Cys Thr Leu Pro Asp Thr Glu Lys
    530                 535                 540

Gln Ile Lys Lys Gln Thr Ala Leu Val Glu Leu Leu Lys His Lys Pro
545                 550                 555                 560

Lys Ala Thr Glu Glu Gln Leu Lys Thr Val Met Glu Asn Phe Val Ala
                565                 570                 575

Phe Val Asp Lys Cys Cys Ala Ala Asp Asp Lys Glu Ala Cys Phe Ala
            580                 585                 590

Val Glu Gly Pro Lys Leu Val Val Ser Thr Gln Thr Ala Leu Ala
        595                 600                 605

<210> SEQ ID NO 46
<211> LENGTH: 12
<212> TYPE: PRT
<213> ORGANISM: Artificial Sequence
<220> FEATURE:
<221> NAME/KEY: VARIANT
<222> LOCATION: 11
<223> OTHER INFORMATION: Xaa = Peptag-modified Cysteine Residue
<220> FEATURE:
<223> OTHER INFORMATION: Synthesized Peptide

<400> SEQUENCE: 46

Ser Leu His Thr Leu Phe Gly Asp Glu Leu Xaa Lys
1               5                   10

<210> SEQ ID NO 47
<211> LENGTH: 12
<212> TYPE: PRT
<213> ORGANISM: Artificial Sequence
<220> FEATURE:
<221> NAME/KEY: VARIANT
<222> LOCATION: 3
<223> OTHER INFORMATION: Xaa = Peptag-modified Cysteine Residue
<220> FEATURE:
<223> OTHER INFORMATION: Synthesized Peptide

<400> SEQUENCE: 47

Tyr Ile Xaa Asp Asn Gln Asp Thr Ile Ser Ser Lys
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthesized Peptide
<220> FEATURE:
<221> NAME/KEY: VARIANT
<222> LOCATION: 9
<223> OTHER INFORMATION: Xaa = Peptag-modified Cysteine Residue

<400> SEQUENCE: 48
```

```
Leu Lys Pro Asp Pro Asn Thr Leu Xaa Asp Glu Phe Lys
 1               5                  10
```

<210> SEQ ID NO 49
<211> LENGTH: 14
<212> TYPE: PRT
<213> ORGANISM: Artificial Sequence
<220> FEATURE:
<223> OTHER INFORMATION: Synthesized Peptide
<220> FEATURE:
<221> NAME/KEY: VARIANT
<222> LOCATION: 1
<223> OTHER INFORMATION: Xaa = Peptag-modified Cysteine Residue

<400> SEQUENCE: 49

```
Xaa Phe Ser Ala Leu Thr Pro Asp Glu Thr Tyr Val Pro Lys
 1               5                  10
```

<210> SEQ ID NO 50
<211> LENGTH: 14
<212> TYPE: PRT
<213> ORGANISM: Artificial Sequence
<220> FEATURE:
<223> OTHER INFORMATION: Synthesized Peptide
<220> FEATURE:
<221> NAME/KEY: VARIANT
<222> LOCATION: 3
<223> OTHER INFORMATION: Xaa = Peptag-modified Cysteine Residue

<400> SEQUENCE: 50

```
Met Pro Xaa Thr Glu Asp Tyr Leu Ser Leu Ile Leu Asn Arg
 1               5                  10
```

<210> SEQ ID NO 51
<211> LENGTH: 16
<212> TYPE: PRT
<213> ORGANISM: Artificial Sequence
<220> FEATURE:
<223> OTHER INFORMATION: Synthesized Peptide
<220> FEATURE:
<221> NAME/KEY: VARIANT
<222> LOCATION: 3
<223> OTHER INFORMATION: Xaa = Peptag-modified Cysteine Residue

<400> SEQUENCE: 51

```
Arg Pro Xaa Phe Ser Ala Leu Thr Pro Asp Glu Thr Tyr Val Pro Lys
 1               5                  10                  15
```

<210> SEQ ID NO 52
<211> LENGTH: 16
<212> TYPE: PRT
<213> ORGANISM: Artificial Sequence
<220> FEATURE:
<223> OTHER INFORMATION: Synthesized Peptide
<220> FEATURE:
<221> NAME/KEY: VARIANT
<222> LOCATION: 3
<223> OTHER INFORMATION: Xaa = Peptag-modified Cysteine Residue

<400> SEQUENCE: 52

```
Asn Glu Xaa Phe Leu Ser His Lys Asp Asp Ser Pro Asp Leu Pro Lys
 1               5                  10                  15
```

<210> SEQ ID NO 53
<211> LENGTH: 16
<212> TYPE: PRT
<213> ORGANISM: Artificial Sequence
<220> FEATURE:
<223> OTHER INFORMATION: Synthesized Peptide

```
<220> FEATURE:
<221> NAME/KEY: VARIANT
<222> LOCATION: 9
<223> OTHER INFORMATION: Xaa = Peptag-modified Cysteine Residue

<400> SEQUENCE: 53

Leu Phe Thr Phe His Ala Asp Ile Xaa Thr Leu Pro Asp Thr Glu Lys
 1               5                  10                  15

<210> SEQ ID NO 54
<211> LENGTH: 21
<212> TYPE: PRT
<213> ORGANISM: Artificial Sequence
<220> FEATURE:
<223> OTHER INFORMATION: Synthesized Peptide
<220> FEATURE:
<221> NAME/KEY: VARIANT
<222> LOCATION: 8
<223> OTHER INFORMATION: Xaa = Peptag-modified Cysteine Residue

<400> SEQUENCE: 54

Gln Glu Pro Glu Arg Asn Glu Xaa Phe Leu Ser His Lys Asp Asp Ser
 1               5                  10                  15

Pro Asp Leu Pro Lys
            20

<210> SEQ ID NO 55
<211> LENGTH: 22
<212> TYPE: PRT
<213> ORGANISM: Artificial Sequence
<220> FEATURE:
<223> OTHER INFORMATION: Synthesized Peptide
<220> FEATURE:
<221> NAME/KEY: VARIANT
<222> LOCATION: 11
<223> OTHER INFORMATION: Xaa = Peptag-modified Cysteine Residue

<400> SEQUENCE: 55

Cys Thr Lys Pro Glu Ser Glu Arg Met Pro Xaa Thr Glu Asp Tyr Leu
 1               5                  10                  15

Ser Leu Ile Leu Asn Arg
            20

<210> SEQ ID NO 56
<211> LENGTH: 12
<212> TYPE: PRT
<213> ORGANISM: Bovine serum albumin
<220> FEATURE:
<221> NAME/KEY: VARIANT
<222> LOCATION: 11
<223> OTHER INFORMATION: Xaa = Peptag-modified Cysteine Residue

<400> SEQUENCE: 56

Ser Leu His Thr Leu Phe Gly Asp Glu Leu Xaa Lys
 1               5                  10

<210> SEQ ID NO 57
<211> LENGTH: 21
<212> TYPE: PRT
<213> ORGANISM: Bovine serum albumin
<220> FEATURE:
<221> NAME/KEY: VARIANT
<222> LOCATION: 14
<223> OTHER INFORMATION: Xaa = Peptag-modified Cysteine Residue

<400> SEQUENCE: 57

Gly Leu Val Leu Ile Ala Phe Ser Gln Tyr Leu Gln Gln Xaa Pro Phe
 1               5                  10                  15
```

```
Asp Glu His Val Lys
            20

<210> SEQ ID NO 58
<211> LENGTH: 31
<212> TYPE: PRT
<213> ORGANISM: Bovine serum albumin
<220> FEATURE:
<221> NAME/KEY: VARIANT
<222> LOCATION: 14
<223> OTHER INFORMATION: Xaa = Peptag-modified Cysteine Residue

<400> SEQUENCE: 58

Gly Leu Val Leu Ile Ala Phe Ser Gln Tyr Leu Gln Gln Xaa Pro Phe
 1               5                  10                  15

Asp Glu His Val Lys Leu Val Asn Glu Leu Thr Glu Phe Ala Lys
            20                  25                  30

<210> SEQ ID NO 59
<211> LENGTH: 31
<212> TYPE: PRT
<213> ORGANISM: Beta-lactogobulin
<220> FEATURE:
<221> NAME/KEY: VARIANT
<222> LOCATION: 27
<223> OTHER INFORMATION: Xaa = Peptag-modified Cysteine Residue

<400> SEQUENCE: 59

Val Tyr Val Glu Glu Leu Lys Pro Thr Pro Glu Gly Asp Gly Leu Glu
 1               5                  10                  15

Ile Leu Leu Gln Lys Trp Glu Asn Asp Glu Xaa Ala Gln Lys Lys
            20                  25                  30

<210> SEQ ID NO 60
<211> LENGTH: 14
<212> TYPE: PRT
<213> ORGANISM: Beta-lactogobulin
<220> FEATURE:
<221> NAME/KEY: VARIANT
<222> LOCATION: 12
<223> OTHER INFORMATION: Xaa = Peptag-modified Cysteine Residue

<400> SEQUENCE: 60

Leu Ser Phe Asn Pro Thr Gln Leu Glu Glu Gln Xaa His Ile
 1               5                  10

<210> SEQ ID NO 61
<211> LENGTH: 20
<212> TYPE: PRT
<213> ORGANISM: Artificial Sequence
<220> FEATURE:
<223> OTHER INFORMATION: Synthesized Peptide

<400> SEQUENCE: 61

Ala Tyr Pro Tyr Asp Val Pro Asp Tyr Ala Ser Leu Glu Val Leu Phe
 1               5                  10                  15

Gln Gly Pro Lys
            20

<210> SEQ ID NO 62
<211> LENGTH: 20
<212> TYPE: PRT
<213> ORGANISM: Artificial Sequence
<220> FEATURE:
<223> OTHER INFORMATION: Synthesized Peptide
<220> FEATURE:
```

```
<221> NAME/KEY: VARIANT
<222> LOCATION: 20
<223> OTHER INFORMATION: Xaa = Ornithine

<400> SEQUENCE: 62

Ala Tyr Pro Tyr Asp Val Pro Asp Tyr Ala Ser Leu Glu Val Leu Phe
 1               5                  10                  15

Gln Gly Pro Xaa
            20

<210> SEQ ID NO 63
<211> LENGTH: 14
<212> TYPE: PRT
<213> ORGANISM: Artificial Sequence
<220> FEATURE:
<223> OTHER INFORMATION: Synthesized Peptide

<400> SEQUENCE: 63

Cys Ala Ser Ala Ser Leu Glu Val Leu Phe Gln Gly Pro Lys
 1               5                  10

<210> SEQ ID NO 64
<211> LENGTH: 14
<212> TYPE: PRT
<213> ORGANISM: Artificial Sequence
<220> FEATURE:
<223> OTHER INFORMATION: Synthesized Peptide
<220> FEATURE:
<221> NAME/KEY: VARIANT
<222> LOCATION: 14
<223> OTHER INFORMATION: Xaa = Ornithine

<400> SEQUENCE: 64

Cys Ala Ser Ala Ser Leu Glu Val Leu Phe Gln Gly Pro Xaa
 1               5                  10

<210> SEQ ID NO 65
<211> LENGTH: 9
<212> TYPE: PRT
<213> ORGANISM: Borus torus
<220> FEATURE:
<221> NAME/KEY: VARIANT
<222> LOCATION: 2
<223> OTHER INFORMATION: Xaa = Modified Cysteine

<400> SEQUENCE: 65

Cys Xaa Thr Glu Ser Leu Val Asn Arg
 1               5

<210> SEQ ID NO 66
<211> LENGTH: 22
<212> TYPE: PRT
<213> ORGANISM: Borus torus
<220> FEATURE:
<221> NAME/KEY: VARIANT
<222> LOCATION: 21
<223> OTHER INFORMATION: Xaa = Modified Cysteine

<400> SEQUENCE: 66

Asp Ala Ile Pro Glu Asn Leu Pro Pro Leu Thr Ala Asp Phe Ala Glu
 1               5                  10                  15

Asp Lys Asp Val Xaa Lys
            20

<210> SEQ ID NO 67
<211> LENGTH: 12
<212> TYPE: PRT
```

```
<213> ORGANISM: Borus torus
<220> FEATURE:
<221> NAME/KEY: VARIANT
<222> LOCATION: 10
<223> OTHER INFORMATION: Xaa = Modified Cysteine

<400> SEQUENCE: 67

Glu Tyr Glu Ala Thr Leu Glu Glu Cys Xaa Ala Lys
 1               5                  10

<210> SEQ ID NO 68
<211> LENGTH: 25
<212> TYPE: PRT
<213> ORGANISM: Borus torus
<220> FEATURE:
<221> NAME/KEY: VARIANT
<222> LOCATION: 10
<223> OTHER INFORMATION: Xaa = Modified Cysteine

<400> SEQUENCE: 68

Glu Tyr Glu Ala Thr Leu Glu Glu Cys Xaa Ala Lys Asp Asp Pro His
 1               5                  10                  15

Ala Cys Tyr Ser Thr Val Phe Asp Lys
            20                  25

<210> SEQ ID NO 69
<211> LENGTH: 16
<212> TYPE: PRT
<213> ORGANISM: Borus torus
<220> FEATURE:
<221> NAME/KEY: VARIANT
<222> LOCATION: 9
<223> OTHER INFORMATION: Xaa = Modified Cysteine

<400> SEQUENCE: 69

Leu Phe Thr Phe His Ala Asp Ile Xaa Thr Leu Pro Asp Thr Glu Lys
 1               5                  10                  15

<210> SEQ ID NO 70
<211> LENGTH: 12
<212> TYPE: PRT
<213> ORGANISM: Borus torus
<220> FEATURE:
<221> NAME/KEY: VARIANT
<222> LOCATION: 4
<223> OTHER INFORMATION: Xaa = Modified Cysteine

<400> SEQUENCE: 70

Leu Lys Glu Xaa Cys Asp Lys Pro Leu Leu Glu Lys
 1               5                  10

<210> SEQ ID NO 71
<211> LENGTH: 13
<212> TYPE: PRT
<213> ORGANISM: Borus torus
<220> FEATURE:
<221> NAME/KEY: VARIANT
<222> LOCATION: 9
<223> OTHER INFORMATION: Xaa = Modified Cysteine

<400> SEQUENCE: 71

Leu Lys Pro Asp Pro Asn Thr Leu Xaa Asp Glu Phe Lys
 1               5                  10

<210> SEQ ID NO 72
<211> LENGTH: 14
<212> TYPE: PRT
<213> ORGANISM: Borus torus
```

-continued

```
<220> FEATURE:
<221> NAME/KEY: VARIANT
<222> LOCATION: 1
<223> OTHER INFORMATION: Xaa = Oxidized Methionine
<220> FEATURE:
<221> NAME/KEY: VARIANT
<222> LOCATION: 3
<223> OTHER INFORMATION: Xaa = Modified Cysteine

<400> SEQUENCE: 72

Xaa Pro Xaa Thr Glu Asp Tyr Leu Ser Leu Ile Leu Asn Arg
 1               5                  10

<210> SEQ ID NO 73
<211> LENGTH: 14
<212> TYPE: PRT
<213> ORGANISM: Borus torus
<220> FEATURE:
<221> NAME/KEY: VARIANT
<222> LOCATION: 3
<223> OTHER INFORMATION: Xaa = Modified Cysteine

<400> SEQUENCE: 73

Met Pro Xaa Thr Glu Asp Tyr Leu Ser Leu Ile Leu Asn Arg
 1               5                  10

<210> SEQ ID NO 74
<211> LENGTH: 16
<212> TYPE: PRT
<213> ORGANISM: Borus torus
<220> FEATURE:
<221> NAME/KEY: VARIANT
<222> LOCATION: 3
<223> OTHER INFORMATION: Xaa = Modified Cysteine

<400> SEQUENCE: 74

Asn Glu Xaa Phe Leu Ser His Lys Asp Asp Ser Pro Asp Leu Pro Lys
 1               5                  10                  15

<210> SEQ ID NO 75
<211> LENGTH: 16
<212> TYPE: PRT
<213> ORGANISM: Borus torus
<220> FEATURE:
<221> NAME/KEY: VARIANT
<222> LOCATION: 3
<223> OTHER INFORMATION: Xaa = Modified Cysteine

<400> SEQUENCE: 75

Arg Pro Xaa Phe Ser Ala Leu Thr Pro Asp Glu Thr Tyr Val Pro Lys
 1               5                  10                  15

<210> SEQ ID NO 76
<211> LENGTH: 9
<212> TYPE: PRT
<213> ORGANISM: Borus torus
<220> FEATURE:
<221> NAME/KEY: VARIANT
<222> LOCATION: 3
<223> OTHER INFORMATION: Xaa = Modified Cysteine

<400> SEQUENCE: 76

Ser His Xaa Ile Ala Glu Val Glu Lys
 1               5

<210> SEQ ID NO 77
<211> LENGTH: 12
<212> TYPE: PRT
<213> ORGANISM: Borus torus
```

```
<220> FEATURE:
<221> NAME/KEY: VARIANT
<222> LOCATION: 11
<223> OTHER INFORMATION: Xaa = Modified Cysteine

<400> SEQUENCE: 77

Ser Leu His Thr Leu Phe Gly Asp Glu Leu Xaa Lys
  1               5                  10

<210> SEQ ID NO 78
<211> LENGTH: 12
<212> TYPE: PRT
<213> ORGANISM: Borus torus
<220> FEATURE:
<221> NAME/KEY: VARIANT
<222> LOCATION: 3
<223> OTHER INFORMATION: Xaa = Modified Cysteine

<400> SEQUENCE: 78

Tyr Ile Xaa Asp Asn Gln Asp Thr Ile Ser Ser Lys
  1               5                  10

<210> SEQ ID NO 79
<211> LENGTH: 14
<212> TYPE: PRT
<213> ORGANISM: Borus torus
<220> FEATURE:
<221> NAME/KEY: VARIANT
<222> LOCATION: 9
<223> OTHER INFORMATION: Xaa = Modified Cysteine

<400> SEQUENCE: 79

Tyr Asn Gly Val Phe Gln Glu Cys Xaa Gln Ala Glu Asp Lys
  1               5                  10

<210> SEQ ID NO 80
<211> LENGTH: 23
<212> TYPE: PRT
<213> ORGANISM: Eschericia coli
<220> FEATURE:
<221> NAME/KEY: VARIANT
<222> LOCATION: 18
<223> OTHER INFORMATION: Xaa = Modified Cysteine

<400> SEQUENCE: 80

Ala Val Val Glu Leu His Thr Ala Asp Gly Thr Leu Ile Glu Ala Glu
  1               5                  10                  15

Ala Xaa Asp Val Gly Phe Arg
            20

<210> SEQ ID NO 81
<211> LENGTH: 13
<212> TYPE: PRT
<213> ORGANISM: Eschericia coli
<220> FEATURE:
<221> NAME/KEY: VARIANT
<222> LOCATION: 5
<223> OTHER INFORMATION: Xaa = Modified Cysteine

<400> SEQUENCE: 81

Ile Gly Leu Asn Xaa Gln Leu Ala Gln Val Ala Glu Arg
  1               5                  10

<210> SEQ ID NO 82
<211> LENGTH: 26
<212> TYPE: PRT
<213> ORGANISM: Eschericia coli
<220> FEATURE:
```

```
<221> NAME/KEY: VARIANT
<222> LOCATION: 21
<223> OTHER INFORMATION: Xaa = Modified Cysteine
<220> FEATURE:
<221> NAME/KEY: VARIANT
<222> LOCATION: 23
<223> OTHER INFORMATION: Xaa = Oxidized Methionine

<400> SEQUENCE: 82

Pro Ser Arg Pro Val Gln Tyr Glu Gly Gly Gly Ala Asp Thr Thr Ala
 1               5                  10                  15

Thr Asp Ile Ile Xaa Pro Xaa Tyr Ala Arg
            20                  25

<210> SEQ ID NO 83
<211> LENGTH: 26
<212> TYPE: PRT
<213> ORGANISM: Eschericia coli
<220> FEATURE:
<221> NAME/KEY: VARIANT
<222> LOCATION: 21
<223> OTHER INFORMATION: Xaa = Modified Cysteine

<400> SEQUENCE: 83

Pro Ser Arg Pro Val Gln Tyr Glu Gly Gly Gly Ala Asp Thr Thr Ala
 1               5                  10                  15

Thr Asp Ile Ile Xaa Pro Met Tyr Ala Arg
            20                  25

<210> SEQ ID NO 84
<211> LENGTH: 23
<212> TYPE: PRT
<213> ORGANISM: Eschericia coli
<220> FEATURE:
<221> NAME/KEY: VARIANT
<222> LOCATION: 18
<223> OTHER INFORMATION: Xaa = Modified Cysteine

<400> SEQUENCE: 84

Pro Val Gln Tyr Glu Gly Gly Gly Ala Asp Thr Thr Ala Thr Asp Ile
 1               5                  10                  15

Ile Xaa Pro Met Tyr Ala Arg
            20

<210> SEQ ID NO 85
<211> LENGTH: 29
<212> TYPE: PRT
<213> ORGANISM: Eschericia coli
<220> FEATURE:
<221> NAME/KEY: VARIANT
<222> LOCATION: 24
<223> OTHER INFORMATION: Xaa = Modified Cysteine
<220> FEATURE:
<221> NAME/KEY: VARIANT
<222> LOCATION: 26
<223> OTHER INFORMATION: Xaa = Oxidized Methionine

<400> SEQUENCE: 85

Ser Val Asp Pro Ser Arg Pro Val Gln Tyr Glu Gly Gly Gly Ala Asp
 1               5                  10                  15

Thr Thr Ala Thr Asp Ile Ile Xaa Pro Xaa Tyr Ala Arg
            20                  25

<210> SEQ ID NO 86
<211> LENGTH: 29
<212> TYPE: PRT
<213> ORGANISM: Eschericia coli
```

```
<220> FEATURE:
<221> NAME/KEY: VARIANT
<222> LOCATION: 24
<223> OTHER INFORMATION: Xaa = Modified Cysteine

<400> SEQUENCE: 86

Ser Val Asp Pro Ser Arg Pro Val Gln Tyr Glu Gly Gly Gly Ala Asp
1               5                   10                  15
Thr Thr Ala Thr Asp Ile Ile Xaa Pro Met Tyr Ala Arg
            20                  25

<210> SEQ ID NO 87
<211> LENGTH: 17
<212> TYPE: PRT
<213> ORGANISM: Oryctolagus cuniculus
<220> FEATURE:
<221> NAME/KEY: VARIANT
<222> LOCATION: 7
<223> OTHER INFORMATION: Xaa = Modified Cysteine

<400> SEQUENCE: 87

Ile Val Ser Asn Ala Ser Xaa Thr Thr Asn Cys Leu Ala Pro Leu Ala
1               5                   10                  15
Lys

<210> SEQ ID NO 88
<211> LENGTH: 17
<212> TYPE: PRT
<213> ORGANISM: Oryctolagus cuniculus
<220> FEATURE:
<221> NAME/KEY: VARIANT
<222> LOCATION: 11
<223> OTHER INFORMATION: Xaa = Modified Cysteine

<400> SEQUENCE: 88

Ile Val Ser Asn Ala Ser Cys Thr Thr Asn Xaa Leu Ala Pro Leu Ala
1               5                   10                  15
Lys

<210> SEQ ID NO 89
<211> LENGTH: 14
<212> TYPE: PRT
<213> ORGANISM: Oryctolagus cuniculus
<220> FEATURE:
<221> NAME/KEY: VARIANT
<222> LOCATION: 13
<223> OTHER INFORMATION: Xaa = Modified Cysteine

<400> SEQUENCE: 89

Val Pro Thr Pro Asn Val Ser Val Val Asp Leu Thr Xaa Arg
1               5                   10

<210> SEQ ID NO 90
<211> LENGTH: 14
<212> TYPE: PRT
<213> ORGANISM: Bos torus
<220> FEATURE:
<221> NAME/KEY: VARIANT
<222> LOCATION: 12
<223> OTHER INFORMATION: Xaa = Modified Cysteine

<400> SEQUENCE: 90

Leu Ser Phe Asn Pro Thr Gln Leu Glu Glu Gln Xaa His Ile
1               5                   10

<210> SEQ ID NO 91
```

```
<211> LENGTH: 17
<212> TYPE: PRT
<213> ORGANISM: Bos torus
<220> FEATURE:
<221> NAME/KEY: VARIANT
<222> LOCATION: 11
<223> OTHER INFORMATION: Xaa = Modified Cysteine

<400> SEQUENCE: 91

Asp Asp Gln Asn Pro His Ser Ser Asn Ile Xaa Asn Ile Ser Cys Asp
 1               5                  10                  15
Lys

<210> SEQ ID NO 92
<211> LENGTH: 17
<212> TYPE: PRT
<213> ORGANISM: Bos torus
<220> FEATURE:
<221> NAME/KEY: VARIANT
<222> LOCATION: 15
<223> OTHER INFORMATION: Xaa = Modified Cysteine

<400> SEQUENCE: 92

Asp Asp Gln Asn Pro His Ser Ser Asn Ile Cys Asn Ile Ser Xaa Asp
 1               5                  10                  15
Lys

<210> SEQ ID NO 93
<211> LENGTH: 14
<212> TYPE: PRT
<213> ORGANISM: Bos torus
<220> FEATURE:
<221> NAME/KEY: VARIANT
<222> LOCATION: 11
<223> OTHER INFORMATION: Xaa = Oxidized Methionine
<220> FEATURE:
<221> NAME/KEY: VARIANT
<222> LOCATION: 12
<223> OTHER INFORMATION: Xaa = Modified Cysteine

<400> SEQUENCE: 93

Phe Leu Asp Asp Asp Leu Thr Asp Asp Ile Xaa Xaa Val Lys
 1               5                  10

<210> SEQ ID NO 94
<211> LENGTH: 14
<212> TYPE: PRT
<213> ORGANISM: Bos torus
<220> FEATURE:
<221> NAME/KEY: VARIANT
<222> LOCATION: 12
<223> OTHER INFORMATION: Xaa = Modified Cysteine

<400> SEQUENCE: 94

Phe Leu Asp Asp Asp Leu Thr Asp Asp Ile Met Xaa Val Lys
 1               5                  10

<210> SEQ ID NO 95
<211> LENGTH: 8
<212> TYPE: PRT
<213> ORGANISM: Bos torus
<220> FEATURE:
<221> NAME/KEY: VARIANT
<222> LOCATION: 6
<223> OTHER INFORMATION: Xaa = Modified Cysteine

<400> SEQUENCE: 95

Leu Asp Gln Trp Leu Xaa Glu Lys
 1               5
```

-continued

```
<210> SEQ ID NO 96
<211> LENGTH: 23
<212> TYPE: PRT
<213> ORGANISM: Bos torus
<220> FEATURE:
<221> NAME/KEY: VARIANT
<222> LOCATION: 21
<223> OTHER INFORMATION: Xaa = Modified Cysteine

<400> SEQUENCE: 96

Asn Ile Cys Asn Ile Ser Cys Asp Lys Phe Leu Asp Asp Asp Leu Thr
 1               5                  10                  15

Asp Asp Ile Met Xaa Val Lys
            20

<210> SEQ ID NO 97
<211> LENGTH: 11
<212> TYPE: PRT
<213> ORGANISM: Bos torus
<220> FEATURE:
<221> NAME/KEY: VARIANT
<222> LOCATION: 5
<223> OTHER INFORMATION: Xaa = Modified Cysteine

<400> SEQUENCE: 97

Ser Ser Asn Ile Xaa Asn Ile Ser Cys Asp Lys
 1               5                  10

<210> SEQ ID NO 98
<211> LENGTH: 10
<212> TYPE: PRT
<213> ORGANISM: Gallus gallus
<220> FEATURE:
<221> NAME/KEY: VARIANT
<222> LOCATION: 8
<223> OTHER INFORMATION: Xaa = Modified Cysteine

<400> SEQUENCE: 98

Ala Asp His Pro Phe Leu Phe Xaa Ile Lys
 1               5                  10

<210> SEQ ID NO 99
<211> LENGTH: 12
<212> TYPE: PRT
<213> ORGANISM: Gallus gallus
<220> FEATURE:
<221> NAME/KEY: VARIANT
<222> LOCATION: 10
<223> OTHER INFORMATION: Xaa = Modified Cysteine

<400> SEQUENCE: 99

Tyr Pro Ile Leu Pro Glu Tyr Leu Gln Xaa Val Lys
 1               5                  10

<210> SEQ ID NO 100
<211> LENGTH: 34
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 100

Xaa Val Val Glu Asp Asp Lys Val Ser Leu Asp Asp Leu Gln Gln Ser
 1               5                  10                  15
```

Ile Glu Glu Asp Glu Asp His Val Gln Ser Thr Asp Ile Ala Ala Met
            20                  25                  30

Gln Lys

<210> SEQ ID NO 101
<211> LENGTH: 15
<212> TYPE: PRT
<213> ORGANISM: Saccharomyces cerevisiae
<220> FEATURE:
<221> NAME/KEY: VARIANT
<222> LOCATION: 12
<223> OTHER INFORMATION: Xaa = Modified Cysteine

<400> SEQUENCE: 101

Ala Val Gly Ile Asp Leu Gly Thr Thr Tyr Ser Xaa Val Ala His
1               5                   10                  15

<210> SEQ ID NO 102
<211> LENGTH: 20
<212> TYPE: PRT
<213> ORGANISM: Saccharomyces cerevisiae
<220> FEATURE:
<221> NAME/KEY: VARIANT
<222> LOCATION: 12
<223> OTHER INFORMATION: Xaa = Modified Cysteine

<400> SEQUENCE: 102

Ala Val Gly Ile Asp Leu Gly Thr Thr Tyr Ser Xaa Val Ala His Phe
1               5                   10                  15

Ala Asn Asp Arg
            20

<210> SEQ ID NO 103
<211> LENGTH: 10
<212> TYPE: PRT
<213> ORGANISM: Saccharomyces cerevisiae
<220> FEATURE:
<221> NAME/KEY: VARIANT
<222> LOCATION: 5
<223> OTHER INFORMATION: Xaa = Modified Cysteine

<400> SEQUENCE: 103

Phe Glu Glu Leu Xaa Ala Asp Leu Phe Arg
1               5                   10

<210> SEQ ID NO 104
<211> LENGTH: 25
<212> TYPE: PRT
<213> ORGANISM: Saccharomyces cerevisiae
<220> FEATURE:
<221> NAME/KEY: VARIANT
<222> LOCATION: 16
<223> OTHER INFORMATION: Xaa = Modified Cysteine

<400> SEQUENCE: 104

Ala Glu Val Ser Asp Val Gly Asn Ala Ile Leu Asp Gly Ala Asp Xaa
1               5                   10                  15

Val Met Leu Ser Gly Glu Thr Ala Lys
            20                  25

<210> SEQ ID NO 105
<211> LENGTH: 19
<212> TYPE: PRT
<213> ORGANISM: Saccharomyces cerevisiae
<220> FEATURE:
<221> NAME/KEY: VARIANT

```
<222> LOCATION: 10
<223> OTHER INFORMATION: Xaa = Modified Cysteine

<400> SEQUENCE: 105

Gly Asn Ala Ile Leu Asp Gly Ala Asp Xaa Val Met Leu Ser Gly Glu
 1               5                  10                  15

Thr Ala Lys

<210> SEQ ID NO 106
<211> LENGTH: 25
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 106

Asn Xaa Thr Pro Lys Pro Thr Ser Thr Thr Glu Thr Val Ala Ala Ser
 1               5                  10                  15

Ala Val Ala Ala Val Phe Glu Gln Lys
            20                  25

<210> SEQ ID NO 107
<211> LENGTH: 17
<212> TYPE: PRT
<213> ORGANISM: Saccharomyces cerevisiae
<220> FEATURE:
<221> NAME/KEY: VARIANT
<222> LOCATION: 4
<223> OTHER INFORMATION: Xaa = Modified Cysteine

<400> SEQUENCE: 107

Pro Val Ile Xaa Ala Thr Gln Met Leu Glu Ser Met Thr Tyr Asn Pro
 1               5                  10                  15

Arg

<210> SEQ ID NO 108
<211> LENGTH: 23
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine
<220> FEATURE:
<221> NAME/KEY: VARIANT
<222> LOCATION: 18
<223> OTHER INFORMATION: Xaa = Oxidized Methionine

<400> SEQUENCE: 108

Ser Asn Leu Ala Gly Lys Pro Val Ile Xaa Ala Thr Gln Met Leu Glu
 1               5                  10                  15

Ser Xaa Thr Tyr Asn Pro Arg
            20

<210> SEQ ID NO 109
<211> LENGTH: 23
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine

<400> SEQUENCE: 109
```

```
Ser Asn Leu Ala Gly Lys Pro Val Ile Xaa Ala Thr Gln Met Leu Glu
 1               5                  10                  15

Ser Met Thr Tyr Asn Pro Arg
            20
```

<210> SEQ ID NO 110
<211> LENGTH: 12
<212> TYPE: PRT
<213> ORGANISM: Saccharomyces cerevisiae
<220> FEATURE:
<221> NAME/KEY: VARIANT
<222> LOCATION: 5
<223> OTHER INFORMATION: Xaa = Modified Cysteine

<400> SEQUENCE: 110

```
Tyr Arg Pro Asn Xaa Pro Ile Ile Leu Val Thr Arg
 1               5                  10
```

<210> SEQ ID NO 111
<211> LENGTH: 22
<212> TYPE: PRT
<213> ORGANISM: Saccharomyces cerevisiae
<220> FEATURE:
<221> NAME/KEY: VARIANT
<222> LOCATION: 6
<223> OTHER INFORMATION: Xaa = Modified Cysteine

<400> SEQUENCE: 111

```
Leu Val Tyr Ser Thr Xaa Ser Leu Asn Pro Ile Glu Asn Glu Ala Val
 1               5                  10                  15

Val Ala Glu Ala Leu Arg
            20
```

<210> SEQ ID NO 112
<211> LENGTH: 15
<212> TYPE: PRT
<213> ORGANISM: Saccharomyces cerevisiae
<220> FEATURE:
<221> NAME/KEY: VARIANT
<222> LOCATION: 13
<223> OTHER INFORMATION: Xaa = Modified Cysteine

<400> SEQUENCE: 112

```
Leu Pro Asn Gln Thr Leu Gly Glu Ile Trp Ala Leu Xaa Asp Arg
 1               5                  10                  15
```

<210> SEQ ID NO 113
<211> LENGTH: 16
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 113

```
Xaa Asp Gly Tyr Ile Leu Glu Gly Glu Glu Leu Ala Phe Tyr Leu Arg
 1               5                  10                  15
```

<210> SEQ ID NO 114
<211> LENGTH: 20
<212> TYPE: PRT
<213> ORGANISM: Saccharomyces cerevisiae
<220> FEATURE:
<221> NAME/KEY: VARIANT
<222> LOCATION: 12
<223> OTHER INFORMATION: Xaa = Modified Cysteine

```
<400> SEQUENCE: 114

Ala Val Gly Ile Asp Leu Gly Thr Thr Tyr Ser Xaa Val Ala His Phe
 1               5                  10                  15

Ser Asn Asp Arg
            20

<210> SEQ ID NO 115
<211> LENGTH: 20
<212> TYPE: PRT
<213> ORGANISM: Saccharomyces cerevisiae
<220> FEATURE:
<221> NAME/KEY: VARIANT
<222> LOCATION: 11
<223> OTHER INFORMATION: Xaa = Oxidized Methionine
<220> FEATURE:
<221> NAME/KEY: VARIANT
<222> LOCATION: 13
<223> OTHER INFORMATION: Xaa = Modified Cysteine

<400> SEQUENCE: 115

Ile Ser Leu Gly Leu Pro Val Gly Ala Ile Xaa Asn Xaa Ala Asp Asn
 1               5                  10                  15

Ser Gly Ala Arg
            20

<210> SEQ ID NO 116
<211> LENGTH: 20
<212> TYPE: PRT
<213> ORGANISM: Saccharomyces cerevisiae
<220> FEATURE:
<221> NAME/KEY: VARIANT
<222> LOCATION: 13
<223> OTHER INFORMATION: Xaa = Modified Cysteine

<400> SEQUENCE: 116

Ile Ser Leu Gly Leu Pro Val Gly Ala Ile Met Asn Xaa Ala Asp Asn
 1               5                  10                  15

Ser Gly Ala Arg
            20

<210> SEQ ID NO 117
<211> LENGTH: 15
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 117

Pro Val Gly Ala Ile Met Asn Xaa Ala Asp Asn Ser Gly Ala Arg
 1               5                  10                  15

<210> SEQ ID NO 118
<211> LENGTH: 20
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 118

Xaa Pro Leu Gly Asn Pro Ala Asn Tyr Pro Phe Ala Thr Ile Asp Pro
 1               5                  10                  15

Glu Glu Ala Arg
```

```
<210> SEQ ID NO 119
<211> LENGTH: 15
<212> TYPE: PRT
<213> ORGANISM: Saccharomyces cerevisiae
<220> FEATURE:
<221> NAME/KEY: VARIANT
<222> LOCATION: 9
<223> OTHER INFORMATION: Xaa = Modified Cysteine

<400> SEQUENCE: 119

Leu Asp Leu Ile Ser Phe Phe Thr Xaa Gly Pro Asp Glu Val Arg
 1               5                  10                  15

<210> SEQ ID NO 120
<211> LENGTH: 11
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 120

Pro Xaa Ile Tyr Leu Ile Asn Leu Ser Glu Arg
 1               5                  10

<210> SEQ ID NO 121
<211> LENGTH: 10
<212> TYPE: PRT
<213> ORGANISM: Saccharomyces cerevisiae

<400> SEQUENCE: 121

Ser Val Asp Ser Ile Tyr Gln Val Val Arg
 1               5                  10

<210> SEQ ID NO 122
<211> LENGTH: 11
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine

<400> SEQUENCE: 122

Ser Gly Gln Gly Ala Phe Gly Asn Met Xaa Arg
 1               5                  10

<210> SEQ ID NO 123
<211> LENGTH: 10
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 123

Xaa Pro Phe Thr Gly Leu Val Ser Ile Arg
 1               5                  10

<210> SEQ ID NO 124
<211> LENGTH: 13
<212> TYPE: PRT
<213> ORGANISM: Saccharomyces cerevisiae
<220> FEATURE:
```

```
<221> NAME/KEY: VARIANT
<222> LOCATION: 12
<223> OTHER INFORMATION: Xaa = Modified Cysteine

<400> SEQUENCE: 124

Val Gln Val Gly Asp Ile Val Thr Val Gly Gln Xaa Arg
 1               5                  10

<210> SEQ ID NO 125
<211> LENGTH: 17
<212> TYPE: PRT
<213> ORGANISM: Saccharomyces cerevisiae
<220> FEATURE:
<221> NAME/KEY: VARIANT
<222> LOCATION: 12
<223> OTHER INFORMATION: Xaa = Modified Cysteine

<400> SEQUENCE: 125

Val Gln Val Gly Asp Ile Val Thr Val Gly Gln Xaa Arg Pro Ile Ser
 1               5                  10                  15

Lys

<210> SEQ ID NO 126
<211> LENGTH: 26
<212> TYPE: PRT
<213> ORGANISM: Saccharomyces cerevisiae
<220> FEATURE:
<221> NAME/KEY: VARIANT
<222> LOCATION: 22
<223> OTHER INFORMATION: Xaa = Modified Cysteine

<400> SEQUENCE: 126

Ala Thr Val Ile Val Leu Asn His Pro Gly Gln Ile Ser Ala Gly Tyr
 1               5                  10                  15

Ser Pro Val Leu Asp Xaa His Thr Ala His
             20                  25

<210> SEQ ID NO 127
<211> LENGTH: 13
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 127

Xaa Val Glu Ala Phe Ser Glu Tyr Pro Pro Leu Gly Arg
 1               5                  10

<210> SEQ ID NO 128
<211> LENGTH: 27
<212> TYPE: PRT
<213> ORGANISM: Saccharomyces cerevisiae
<220> FEATURE:
<221> NAME/KEY: VARIANT
<222> LOCATION: 23
<223> OTHER INFORMATION: Xaa = Modified Cysteine

<400> SEQUENCE: 128

Asn Ala Thr Val Ile Val Leu Asn His Pro Gly Gln Ile Ser Ala Gly
 1               5                  10                  15

Tyr Ser Pro Val Leu Asp Xaa His Thr Ala His
             20                  25

<210> SEQ ID NO 129
```

```
<211> LENGTH: 29
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Oxidized Methionine
<220> FEATURE:
<221> NAME/KEY: VARIANT
<222> LOCATION: 11
<223> OTHER INFORMATION: Xaa = Modified Cysteine

<400> SEQUENCE: 129

Asn Xaa Ile Thr Gly Thr Ser Gln Ala Asp Xaa Ala Ile Leu Ile Ile
 1               5                  10                  15

Ala Gly Gly Val Gly Glu Phe Glu Ala Gly Ile Ser Lys
            20                  25

<210> SEQ ID NO 130
<211> LENGTH: 29
<212> TYPE: PRT
<213> ORGANISM: Saccharomyces cerevisiae
<220> FEATURE:
<221> NAME/KEY: VARIANT
<222> LOCATION: 11
<223> OTHER INFORMATION: Xaa = Modified Cysteine

<400> SEQUENCE: 130

Asn Met Ile Thr Gly Thr Ser Gln Ala Asp Xaa Ala Ile Leu Ile Ile
 1               5                  10                  15

Ala Gly Gly Val Gly Glu Phe Glu Ala Gly Ile Ser Lys
            20                  25

<210> SEQ ID NO 131
<211> LENGTH: 15
<212> TYPE: PRT
<213> ORGANISM: Saccharomyces cerevisiae
<220> FEATURE:
<221> NAME/KEY: VARIANT
<222> LOCATION: 3
<223> OTHER INFORMATION: Xaa = Modified Cysteine

<400> SEQUENCE: 131

Pro Met Xaa Val Glu Ala Phe Ser Glu Tyr Pro Pro Leu Gly Arg
 1               5                  10                  15

<210> SEQ ID NO 132
<211> LENGTH: 18
<212> TYPE: PRT
<213> ORGANISM: Saccharomyces cerevisiae
<220> FEATURE:
<221> NAME/KEY: VARIANT
<222> LOCATION: 6
<223> OTHER INFORMATION: Xaa = Modified Cysteine

<400> SEQUENCE: 132

Pro Ser Lys Pro Met Xaa Val Glu Ala Phe Ser Glu Tyr Pro Pro Leu
 1               5                  10                  15

Gly Arg

<210> SEQ ID NO 133
<211> LENGTH: 20
<212> TYPE: PRT
<213> ORGANISM: Saccharomyces cerevisiae
<220> FEATURE:
<221> NAME/KEY: VARIANT
<222> LOCATION: 19
<223> OTHER INFORMATION: Xaa = Modified Cysteine
```

-continued

```
<400> SEQUENCE: 133

Ile Pro Ile Phe Ser Ala Ser Gly Leu Pro His Asn Glu Ile Ala Ala
1               5                   10                  15

Gln Ile Xaa Arg
            20

<210> SEQ ID NO 134
<211> LENGTH: 14
<212> TYPE: PRT
<213> ORGANISM: Saccharomyces cerevisiae
<220> FEATURE:
<221> NAME/KEY: VARIANT
<222> LOCATION: 6
<223> OTHER INFORMATION: Xaa = Modified Cysteine

<400> SEQUENCE: 134

Gly Ala Ala Phe Ile Xaa Ala Ile His Ser Pro Thr Leu Arg
1               5                   10

<210> SEQ ID NO 135
<211> LENGTH: 10
<212> TYPE: PRT
<213> ORGANISM: Saccharomyces cerevisiae
<220> FEATURE:
<221> NAME/KEY: VARIANT
<222> LOCATION: 5
<223> OTHER INFORMATION: Xaa = Modified Cysteine

<400> SEQUENCE: 135

Gly Asn Glu His Xaa Phe Val Ile Leu Arg
1               5                   10

<210> SEQ ID NO 136
<211> LENGTH: 28
<212> TYPE: PRT
<213> ORGANISM: Saccharomyces cerevisiae
<220> FEATURE:
<221> NAME/KEY: VARIANT
<222> LOCATION: 14
<223> OTHER INFORMATION: Xaa = Modified Cysteine
<220> FEATURE:
<221> NAME/KEY: VARIANT
<222> LOCATION: 24
<223> OTHER INFORMATION: Xaa = Oxidized Methionine

<400> SEQUENCE: 136

Asn Gly Thr Asp Gly Thr Leu Asn Val Ala Val Asp Ala Xaa Gln Ala
1               5                   10                  15

Ala Ala His Ser His His Phe Xaa Gly Val Thr Lys
            20                  25

<210> SEQ ID NO 137
<211> LENGTH: 28
<212> TYPE: PRT
<213> ORGANISM: Saccharomyces cerevisiae
<220> FEATURE:
<221> NAME/KEY: VARIANT
<222> LOCATION: 14
<223> OTHER INFORMATION: Xaa = Modified Cysteine

<400> SEQUENCE: 137

Asn Gly Thr Asp Gly Thr Leu Asn Val Ala Val Asp Ala Xaa Gln Ala
1               5                   10                  15

Ala Ala His Ser His His Phe Met Gly Val Thr Lys
            20                  25
```

```
<210> SEQ ID NO 138
<211> LENGTH: 22
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 138

Val Leu Val Ile Val Gly Pro Xaa Ser Ile His Asp Leu Glu Ala Ala
 1               5                  10                  15

Gln Glu Tyr Ala Leu Arg
            20

<210> SEQ ID NO 139
<211> LENGTH: 37
<212> TYPE: PRT
<213> ORGANISM: Saccharomyces cerevisiae
<220> FEATURE:
<221> NAME/KEY: VARIANT
<222> LOCATION: 6
<223> OTHER INFORMATION: Xaa = Modified Cysteine

<400> SEQUENCE: 139

Val Asn Asp Val Val Xaa Glu Gln Ile Ala Asn Gly Glu Asn Ala Ile
 1               5                  10                  15

Thr Gly Val Met Ile Glu Ser Asn Ile Asn Glu Gly Asn Gln Gly Ile
            20                  25                  30

Pro Ala Glu Gly Lys
        35

<210> SEQ ID NO 140
<211> LENGTH: 20
<212> TYPE: PRT
<213> ORGANISM: Saccharomyces cerevisiae
<220> FEATURE:
<221> NAME/KEY: VARIANT
<222> LOCATION: 9
<223> OTHER INFORMATION: Xaa = Modified Cysteine

<400> SEQUENCE: 140

Tyr Gly Val Ser Ile Thr Asp Ala Xaa Ile Gly Trp Glu Thr Thr Glu
 1               5                  10                  15

Asp Val Leu Arg
            20

<210> SEQ ID NO 141
<211> LENGTH: 16
<212> TYPE: PRT
<213> ORGANISM: Saccharomyces cerevisiae
<220> FEATURE:
<221> NAME/KEY: VARIANT
<222> LOCATION: 6
<223> OTHER INFORMATION: Xaa = Modified Cysteine

<400> SEQUENCE: 141

Glu Ile Ser Gln Gly Xaa Gly Ala Tyr Leu Met Ser Asp Met Ala His
 1               5                  10                  15

<210> SEQ ID NO 142
<211> LENGTH: 12
<212> TYPE: PRT
<213> ORGANISM: Saccharomyces cerevisiae
<220> FEATURE:
<221> NAME/KEY: VARIANT
```

```
<222> LOCATION: 10
<223> OTHER INFORMATION: Xaa = Any Amino Acid

<400> SEQUENCE: 142

Leu Val Glu Pro Phe Gly Val Leu Glu Xaa Ala Arg
 1               5                  10

<210> SEQ ID NO 143
<211> LENGTH: 23
<212> TYPE: PRT
<213> ORGANISM: Saccharomyces cerevisiae
<220> FEATURE:
<221> NAME/KEY: VARIANT
<222> LOCATION: 21
<223> OTHER INFORMATION: Xaa = Modified Cysteine

<400> SEQUENCE: 143

Phe His Ala Ala Gln Leu Pro Thr Glu Thr Leu Glu Val Glu Thr Gln
 1               5                  10                  15

Pro Gly Val Leu Xaa Ser Arg
            20

<210> SEQ ID NO 144
<211> LENGTH: 8
<212> TYPE: PRT
<213> ORGANISM: Saccharomyces cerevisiae
<220> FEATURE:
<221> NAME/KEY: VARIANT
<222> LOCATION: 3
<223> OTHER INFORMATION: Xaa = Any Amino AcidXaa = Modified Cysteine

<400> SEQUENCE: 144

Asp His Xaa Ile Val Val Gly Arg
 1               5

<210> SEQ ID NO 145
<211> LENGTH: 20
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 145

Met Leu Ile Gly Met Val Asp Xaa Val Phe Ala Asp Val Ala Gln Pro
 1               5                  10                  15

Asp Gln Ala Arg
            20

<210> SEQ ID NO 146
<211> LENGTH: 19
<212> TYPE: PRT
<213> ORGANISM: Saccharomyces cerevisiae
<220> FEATURE:
<221> NAME/KEY: VARIANT
<222> LOCATION: 14
<223> OTHER INFORMATION: Xaa = Modified Cysteine

<400> SEQUENCE: 146

Asp Asn Ser Pro Phe Phe Val Leu Asn Ser Asp Val Ile Xaa Glu Tyr
 1               5                  10                  15

Pro Phe Lys

<210> SEQ ID NO 147
<211> LENGTH: 15
```

```
<212> TYPE: PRT
<213> ORGANISM: Saccharomyces cerevisiae
<220> FEATURE:
<221> NAME/KEY: VARIANT
<222> LOCATION: 14
<223> OTHER INFORMATION: Xaa = Modified Cysteine

<400> SEQUENCE: 147

Ser Thr Ile Val Gly Trp Asn Ser Thr Val Gly Gln Trp Xaa Arg
1               5                  10                  15

<210> SEQ ID NO 148
<211> LENGTH: 10
<212> TYPE: PRT
<213> ORGANISM: Saccharomyces cerevisiae
<220> FEATURE:
<221> NAME/KEY: VARIANT
<222> LOCATION: 5
<223> OTHER INFORMATION: Xaa = Modified Cysteine

<400> SEQUENCE: 148

Ser Val Val Leu Xaa Asn Ser Thr Ile Lys
1               5                  10

<210> SEQ ID NO 149
<211> LENGTH: 10
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 149

Val Xaa Ser Ser His Thr Gly Leu Val Arg
1               5                  10

<210> SEQ ID NO 150
<211> LENGTH: 10
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 150

Xaa Ala Thr Ile Thr Pro Asp Glu Ala Arg
1               5                  10

<210> SEQ ID NO 151
<211> LENGTH: 17
<212> TYPE: PRT
<213> ORGANISM: Saccharomyces cerevisiae
<220> FEATURE:
<221> NAME/KEY: VARIANT
<222> LOCATION: 16
<223> OTHER INFORMATION: Xaa = Modified Cysteine

<400> SEQUENCE: 151

Ser His Phe Asn Ala Leu Tyr Asp Thr Leu Leu Glu Ser Asn Leu Xaa
1               5                  10                  15

Lys

<210> SEQ ID NO 152
<211> LENGTH: 18
<212> TYPE: PRT
<213> ORGANISM: Saccharomyces cerevisiae
```

```
<220> FEATURE:
<221> NAME/KEY: VARIANT
<222> LOCATION: 17
<223> OTHER INFORMATION: Xaa = Modified Cysteine

<400> SEQUENCE: 152

Asp Thr Val Leu Ile Val Leu Ile Asp Asp Glu Leu Glu Asp Gly Ala
 1               5                  10                  15

Xaa Arg

<210> SEQ ID NO 153
<211> LENGTH: 14
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine

<400> SEQUENCE: 153

Leu Gly Asp Leu Val Thr Ile His Pro Xaa Pro Asp Ile Lys
 1               5                  10

<210> SEQ ID NO 154
<211> LENGTH: 26
<212> TYPE: PRT
<213> ORGANISM: Saccharomyces cerevisiae
<220> FEATURE:
<221> NAME/KEY: VARIANT
<222> LOCATION: 24
<223> OTHER INFORMATION: Xaa = Modified Cysteine

<400> SEQUENCE: 154

Asp Ile Glu Asn Leu Val Ala Asp Ala Val Glu Val Asn Ile Pro Phe
 1               5                  10                  15

Asn Asn Pro Ile Thr Gly Phe Xaa Ala Phe
             20                  25

<210> SEQ ID NO 155
<211> LENGTH: 13
<212> TYPE: PRT
<213> ORGANISM: Saccharomyces cerevisiae
<220> FEATURE:
<221> NAME/KEY: VARIANT
<222> LOCATION: 9
<223> OTHER INFORMATION: Xaa = Modified Cysteine

<400> SEQUENCE: 155

Val Gly Ile Ala Asp Thr Val Gly Xaa Ala Asn Pro Arg
 1               5                  10

<210> SEQ ID NO 156
<211> LENGTH: 14
<212> TYPE: PRT
<213> ORGANISM: Saccharomyces cerevisiae
<220> FEATURE:
<221> NAME/KEY: VARIANT
<222> LOCATION: 4
<223> OTHER INFORMATION: Xaa = Modified Cysteine

<400> SEQUENCE: 156

Ser Ile Ala Xaa Val Leu Thr Val Ile Asn Glu Gln Gln Arg
 1               5                  10

<210> SEQ ID NO 157
<211> LENGTH: 27
<212> TYPE: PRT
```

```
<213> ORGANISM: Saccharomyces cerevisiae
<220> FEATURE:
<221> NAME/KEY: VARIANT
<222> LOCATION: 5
<223> OTHER INFORMATION: Xaa = Modified Cysteine

<400> SEQUENCE: 157

Glu Arg Val Asn Xaa Lys Glu Asn Thr Leu Leu Gly Glu Phe Asp Leu
 1               5                  10                  15

Lys Asn Ile Pro Met Met Pro Ala Gly Glu Pro
            20                  25

<210> SEQ ID NO 158
<211> LENGTH: 21
<212> TYPE: PRT
<213> ORGANISM: Saccharomyces cerevisiae
<220> FEATURE:
<221> NAME/KEY: VARIANT
<222> LOCATION: 5
<223> OTHER INFORMATION: Xaa = Modified Cysteine

<400> SEQUENCE: 158

Thr Phe Thr Thr Xaa Ala Asp Asn Gln Thr Thr Val Gln Phe Pro Val
 1               5                  10                  15

Tyr Gln Gly Glu Arg
            20

<210> SEQ ID NO 159
<211> LENGTH: 21
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 159

Ile Xaa Ala Asn His Ile Ile Ala Pro Glu Tyr Thr Leu Lys Pro Asn
 1               5                  10                  15

Val Gly Ser Asp Arg
            20

<210> SEQ ID NO 160
<211> LENGTH: 12
<212> TYPE: PRT
<213> ORGANISM: Saccharomyces cerevisiae
<220> FEATURE:
<221> NAME/KEY: VARIANT
<222> LOCATION: 5
<223> OTHER INFORMATION: Xaa = Modified Cysteine

<400> SEQUENCE: 160

Ile Met Ile Asp Xaa Ser His Gly Asn Ser Asn Lys
 1               5                  10

<210> SEQ ID NO 161
<211> LENGTH: 28
<212> TYPE: PRT
<213> ORGANISM: Saccharomyces cerevisiae
<220> FEATURE:
<221> NAME/KEY: VARIANT
<222> LOCATION: 19
<223> OTHER INFORMATION: Xaa = Modified Cysteine

<400> SEQUENCE: 161

Leu Pro Ile Ala Gly Glu Met Leu Asp Thr Ile Ser Pro Gln Phe Leu
 1               5                  10                  15
```

```
Ser Asp Xaa Phe Ser Leu Gly Ala Ile Gly Ala Arg
          20                  25
```

<210> SEQ ID NO 162
<211> LENGTH: 11
<212> TYPE: PRT
<213> ORGANISM: Saccharomyces cerevisiae
<220> FEATURE:
<221> NAME/KEY: VARIANT
<222> LOCATION: 3
<223> OTHER INFORMATION: Xaa = Modified Cysteine

<400> SEQUENCE: 162

```
Leu Glu Xaa Pro Pro Leu Thr Asn Ala Arg
 1               5                  10
```

<210> SEQ ID NO 163
<211> LENGTH: 17
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine

<400> SEQUENCE: 163

```
Tyr Asp Ser Ile Glu Val Ser Gly Gly Xaa Pro Ile Val Ile Gly Leu
 1               5                  10                  15
Arg
```

<210> SEQ ID NO 164
<211> LENGTH: 11
<212> TYPE: PRT
<213> ORGANISM: Saccharomyces cerevisiae
<220> FEATURE:
<221> NAME/KEY: VARIANT
<222> LOCATION: 9
<223> OTHER INFORMATION: Xaa = Modified Cysteine

<400> SEQUENCE: 164

```
Ala Pro Glu Ser Leu Leu Thr Gly Xaa Asn Arg
 1               5                  10
```

<210> SEQ ID NO 165
<211> LENGTH: 13
<212> TYPE: PRT
<213> ORGANISM: Saccharomyces cerevisiae
<220> FEATURE:
<221> NAME/KEY: VARIANT
<222> LOCATION: 12
<223> OTHER INFORMATION: Xaa = Modified Cysteine

<400> SEQUENCE: 165

```
Ala Leu Ile Leu Ala Ala Leu Gly Glu Gly Gln Xaa Lys
 1               5                  10
```

<210> SEQ ID NO 166
<211> LENGTH: 23
<212> TYPE: PRT
<213> ORGANISM: Saccharomyces cerevisiae
<220> FEATURE:
<221> NAME/KEY: VARIANT
<222> LOCATION: 17
<223> OTHER INFORMATION: Xaa = Modified Cysteine

<400> SEQUENCE: 166

```
Ala Gly Pro Asn Thr Asn Gly Ser Gln Phe Phe Ile Thr Thr Val Pro
```

```
                    1               5              10              15
Xaa Pro Trp Leu Asp Gly Lys
                   20
```

<210> SEQ ID NO 167
<211> LENGTH: 25
<212> TYPE: PRT
<213> ORGANISM: Saccharomyces cerevisiae
<220> FEATURE:
<221> NAME/KEY: VARIANT
<222> LOCATION: 19
<223> OTHER INFORMATION: Xaa = Modified Cysteine

<400> SEQUENCE: 167

```
Ala Asn Ala Gly Pro Asn Thr Asn Gly Ser Gln Phe Phe Ile Thr Thr
 1               5                  10                  15
Val Pro Xaa Pro Trp Leu Asp Gly Lys
                20                  25
```

<210> SEQ ID NO 168
<211> LENGTH: 31
<212> TYPE: PRT
<213> ORGANISM: Saccharomyces cerevisiae
<220> FEATURE:
<221> NAME/KEY: VARIANT
<222> LOCATION: 6
<223> OTHER INFORMATION: Xaa = Oxidized Methionine
<220> FEATURE:
<221> NAME/KEY: VARIANT
<222> LOCATION: 25
<223> OTHER INFORMATION: Xaa = Modified Cysteine

<400> SEQUENCE: 168

```
Pro Gly Leu Leu Ser Xaa Ala Asn Ala Gly Pro Asn Thr Asn Gly Ser
 1               5                  10                  15
Gln Phe Phe Ile Thr Thr Val Pro Xaa Pro Trp Leu Asp Gly Lys
                20                  25                  30
```

<210> SEQ ID NO 169
<211> LENGTH: 14
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine

<400> SEQUENCE: 169

```
Val Ala Val Ser Asp Gly His Thr Glu Xaa Ile Ser Leu Arg
 1               5                  10
```

<210> SEQ ID NO 170
<211> LENGTH: 25
<212> TYPE: PRT
<213> ORGANISM: Saccharomyces cerevisiae
<220> FEATURE:
<221> NAME/KEY: VARIANT
<222> LOCATION: 18
<223> OTHER INFORMATION: Xaa = Modified Cysteine

<400> SEQUENCE: 170

```
Ala Ala Ala Ala Gln Asp Glu Ile Thr Gly Asp Gly Thr Thr Thr Val
 1               5                  10                  15
Val Xaa Leu Val Gly Glu Leu Leu Arg
                20                  25
```

```
<210> SEQ ID NO 171
<211> LENGTH: 21
<212> TYPE: PRT
<213> ORGANISM: Saccharomyces cerevisiae
<220> FEATURE:
<221> NAME/KEY: VARIANT
<222> LOCATION: 16
<223> OTHER INFORMATION: Xaa = Modified Cysteine

<400> SEQUENCE: 171

Asn Ala Ile Thr Gly Ala Thr Gly Ile Ala Ser Asn Leu Leu Leu Xaa
 1               5                  10                  15

Asp Glu Leu Leu Arg
            20

<210> SEQ ID NO 172
<211> LENGTH: 17
<212> TYPE: PRT
<213> ORGANISM: Saccharomyces cerevisiae
<220> FEATURE:
<221> NAME/KEY: VARIANT
<222> LOCATION: 4
<223> OTHER INFORMATION: Xaa = Modified Cysteine

<400> SEQUENCE: 172

Val Pro Phe Xaa Pro Leu Val Gly Ser Glu Leu Tyr Ser Val Glu Val
 1               5                  10                  15

Lys

<210> SEQ ID NO 173
<211> LENGTH: 18
<212> TYPE: PRT
<213> ORGANISM: Saccharomyces cerevisiae
<220> FEATURE:
<221> NAME/KEY: VARIANT
<222> LOCATION: 9
<223> OTHER INFORMATION: Xaa = Modified Cysteine

<400> SEQUENCE: 173

Tyr Ala Leu Gln Leu Leu Ala Pro Xaa Gly Ile Leu Ala Gln Thr Ser
 1               5                  10                  15

Asn Arg

<210> SEQ ID NO 174
<211> LENGTH: 10
<212> TYPE: PRT
<213> ORGANISM: Saccharomyces cerevisiae
<220> FEATURE:
<221> NAME/KEY: VARIANT
<222> LOCATION: 9
<223> OTHER INFORMATION: Xaa = Modified Cysteine

<400> SEQUENCE: 174

Asp Glu Leu Thr Asn Asn Pro Ala Xaa Lys
 1               5                  10

<210> SEQ ID NO 175
<211> LENGTH: 16
<212> TYPE: PRT
<213> ORGANISM: Saccharomyces cerevisiae
<220> FEATURE:
<221> NAME/KEY: VARIANT
<222> LOCATION: 13
<223> OTHER INFORMATION: Xaa = Modified Cysteine

<400> SEQUENCE: 175

Ser Gln Asn Ala Ala Val Asn Gly Ser Gly Ile Ala Xaa Gln Gln Arg
```

```
<210> SEQ ID NO 176
<211> LENGTH: 22
<212> TYPE: PRT
<213> ORGANISM: Saccharomyces cerevisiae
<220> FEATURE:
<221> NAME/KEY: VARIANT
<222> LOCATION: 14
<223> OTHER INFORMATION: Xaa = Modified Cysteine

<400> SEQUENCE: 176

Asn Lys Pro Leu Ala Val Ile Gly Gly Gly Asp Ser Ala Xaa Glu Glu
 1               5                  10                  15

Ala Gln Phe Leu Thr Lys
            20

<210> SEQ ID NO 177
<211> LENGTH: 18
<212> TYPE: PRT
<213> ORGANISM: Saccharomyces cerevisiae
<220> FEATURE:
<221> NAME/KEY: VARIANT
<222> LOCATION: 14
<223> OTHER INFORMATION: Xaa = Modified Cysteine

<400> SEQUENCE: 177

Ala Glu Gln Leu Tyr Glu Gly Pro Ala Asp Asp Ala Asn Xaa Ile Ala
 1               5                  10                  15

Ile Lys

<210> SEQ ID NO 178
<211> LENGTH: 19
<212> TYPE: PRT
<213> ORGANISM: Saccharomyces cerevisiae
<220> FEATURE:
<221> NAME/KEY: VARIANT
<222> LOCATION: 3
<223> OTHER INFORMATION: Xaa = Modified Cysteine

<400> SEQUENCE: 178

Ile Trp Xaa Phe Gly Pro Asp Gly Asn Gly Pro Asn Leu Val Ile Asp
 1               5                  10                  15

Gln Thr Lys

<210> SEQ ID NO 179
<211> LENGTH: 24
<212> TYPE: PRT
<213> ORGANISM: Saccharomyces cerevisiae
<220> FEATURE:
<221> NAME/KEY: VARIANT
<222> LOCATION: 16
<223> OTHER INFORMATION: Xaa = Modified Cysteine

<400> SEQUENCE: 179

Val Thr Asp Gly Ala Leu Val Val Val Asp Thr Ile Glu Gly Val Xaa
 1               5                  10                  15

Val Gln Thr Glu Thr Val Leu Arg
            20

<210> SEQ ID NO 180
<211> LENGTH: 12
<212> TYPE: PRT
<213> ORGANISM: Saccharomyces cerevisiae
<220> FEATURE:
<221> NAME/KEY: VARIANT
```

```
<222> LOCATION: 11
<223> OTHER INFORMATION: Xaa = Modified Cysteine

<400> SEQUENCE: 180

Glu Ile Leu Gly Thr Ala Gln Ser Val Gly Xaa Arg
 1               5                  10

<210> SEQ ID NO 181
<211> LENGTH: 11
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 181

Leu Xaa Asp Glu Ile Ala Thr Ile Gln Ser Lys
 1               5                  10

<210> SEQ ID NO 182
<211> LENGTH: 11
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine

<400> SEQUENCE: 182

Gly His Thr Glu Ala Gly Val Asp Leu Xaa Lys
 1               5                  10

<210> SEQ ID NO 183
<211> LENGTH: 9
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 183

Ser Leu Val Ala Ala Gly Leu Xaa Lys
 1               5

<210> SEQ ID NO 184
<211> LENGTH: 23
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 184

Thr Xaa Asn Val Leu Val Ala Ile Glu Gln Gln Ser Pro Asp Ile Ala
 1               5                  10                  15

Gln Gly Leu His Tyr Glu Lys
            20

<210> SEQ ID NO 185
<211> LENGTH: 15
<212> TYPE: PRT
<213> ORGANISM: Saccharomyces cerevisiae
<220> FEATURE:
<221> NAME/KEY: VARIANT
<222> LOCATION: 12
```

<223> OTHER INFORMATION: Xaa = Modified Cysteine

<400> SEQUENCE: 185

Thr His Leu Met Gln Pro Pro Tyr Ser Ile Leu Xaa Asp Tyr Arg
1               5                   10                  15

<210> SEQ ID NO 186
<211> LENGTH: 14
<212> TYPE: PRT
<213> ORGANISM: Saccharomyces cerevisiae
<220> FEATURE:
<221> NAME/KEY: VARIANT
<222> LOCATION: 9
<223> OTHER INFORMATION: Xaa = Modified Cysteine

<400> SEQUENCE: 186

Leu Gly Gly Ser Ser Leu Leu Glu Xaa Val Val Phe Gly Arg
1               5                   10

<210> SEQ ID NO 187
<211> LENGTH: 28
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine

<400> SEQUENCE: 187

Phe Val Leu Ser Gly Ala Asn Ile Met Xaa Pro Gly Leu Thr Ser Ala
1               5                   10                  15

Gly Ala Asp Leu Pro Pro Ala Pro Gly Tyr Glu Lys
            20                  25

<210> SEQ ID NO 188
<211> LENGTH: 19
<212> TYPE: PRT
<213> ORGANISM: Saccharomyces cerevisiae
<220> FEATURE:
<221> NAME/KEY: VARIANT
<222> LOCATION: 16
<223> OTHER INFORMATION: Xaa = Modified Cysteine

<400> SEQUENCE: 188

His Tyr Ser Lys Pro Asp Gly Pro Asn Asn Asn Val Ala Val Val Xaa
1               5                   10                  15

Ser Ala Arg

<210> SEQ ID NO 189
<211> LENGTH: 12
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 189

Xaa Asp Leu Gly Ile Thr Gly Val Asp Gln Val Arg
1               5                   10

<210> SEQ ID NO 190
<211> LENGTH: 11
<212> TYPE: PRT
<213> ORGANISM: Saccharomyces cerevisiae
<220> FEATURE:
<221> NAME/KEY: VARIANT

```
<222> LOCATION: 9
<223> OTHER INFORMATION: Xaa = Modified Cysteine

<400> SEQUENCE: 190

Gly Met Leu Thr Gly Pro Ile Thr Xaa Leu Arg
1               5                   10

<210> SEQ ID NO 191
<211> LENGTH: 13
<212> TYPE: PRT
<213> ORGANISM: Saccharomyces cerevisiae
<220> FEATURE:
<221> NAME/KEY: VARIANT
<222> LOCATION: 11
<223> OTHER INFORMATION: Xaa = Modified Cysteine

<400> SEQUENCE: 191

Ala Gln His Glu Ser Ser Ser Pro Val Leu Xaa Thr Arg
1               5                   10

<210> SEQ ID NO 192
<211> LENGTH: 14
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 192

Ile Xaa Gly Asp Ile His Gly Gln Tyr Tyr Asp Leu Leu Arg
1               5                   10

<210> SEQ ID NO 193
<211> LENGTH: 19
<212> TYPE: PRT
<213> ORGANISM: Saccharomyces cerevisiae
<220> FEATURE:
<221> NAME/KEY: VARIANT
<222> LOCATION: 3
<223> OTHER INFORMATION: Xaa = Modified Cysteine

<400> SEQUENCE: 193

Ile Phe Xaa Met His Gly Gly Leu Ser Pro Asp Leu Asn Ser Met Glu
1               5                   10                  15

Gln Ile Arg

<210> SEQ ID NO 194
<211> LENGTH: 12
<212> TYPE: PRT
<213> ORGANISM: Saccharomyces cerevisiae
<220> FEATURE:
<221> NAME/KEY: VARIANT
<222> LOCATION: 9
<223> OTHER INFORMATION: Xaa = Modified Cysteine

<400> SEQUENCE: 194

Ser Glu His Gln Val Glu Leu Ile Xaa Ser Tyr Arg
1               5                   10

<210> SEQ ID NO 195
<211> LENGTH: 13
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine
```

-continued

```
<400> SEQUENCE: 195

Ala Ala Gln Leu Gly Phe Asn Thr Ala Xaa Val Glu Lys
 1               5                  10

<210> SEQ ID NO 196
<211> LENGTH: 23
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 196

Leu Xaa Tyr Val Ala Leu Asp Phe Glu Gln Glu Met Gln Thr Ala Ala
 1               5                  10                  15

Gln Ser Ser Ser Ile Glu Lys
            20

<210> SEQ ID NO 197
<211> LENGTH: 9
<212> TYPE: PRT
<213> ORGANISM: Saccharomyces cerevisiae
<220> FEATURE:
<221> NAME/KEY: VARIANT
<222> LOCATION: 3
<223> OTHER INFORMATION: Xaa = Modified Cysteine

<400> SEQUENCE: 197

Thr Tyr Xaa Leu Gln His Val Glu Lys
 1               5

<210> SEQ ID NO 198
<211> LENGTH: 18
<212> TYPE: PRT
<213> ORGANISM: Saccharomyces cerevisiae
<220> FEATURE:
<221> NAME/KEY: VARIANT
<222> LOCATION: 14
<223> OTHER INFORMATION: Xaa = Modified Cysteine

<400> SEQUENCE: 198

Glu Ala Glu Ile Leu Val Val Thr Gly Asp Asn Phe Gly Xaa Gly Ser
 1               5                  10                  15

Ser Arg

<210> SEQ ID NO 199
<211> LENGTH: 16
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 199

His Xaa Leu Val Asn Gly Leu Asp Asp Ile Gly Ile Thr Leu Gln Lys
 1               5                  10                  15

<210> SEQ ID NO 200
<211> LENGTH: 17
<212> TYPE: PRT
<213> ORGANISM: Saccharomyces cerevisiae
<220> FEATURE:
<221> NAME/KEY: VARIANT
<222> LOCATION: 3
```

-continued

<223> OTHER INFORMATION: Xaa = Modified Cysteine

<400> SEQUENCE: 200

Val Asp Xaa Thr Leu Ala Thr Val Asp His Asn Ile Pro Thr Glu Ser
1               5                   10                  15
Arg

<210> SEQ ID NO 201
<211> LENGTH: 10
<212> TYPE: PRT
<213> ORGANISM: Saccharomyces cerevisiae
<220> FEATURE:
<221> NAME/KEY: VARIANT
<222> LOCATION: 6
<223> OTHER INFORMATION: Xaa = Modified Cysteine

<400> SEQUENCE: 201

Val Phe Ile Gly Ser Xaa Thr Asn Gly Arg
1               5                   10

<210> SEQ ID NO 202
<211> LENGTH: 18
<212> TYPE: PRT
<213> ORGANISM: Saccharomyces cerevisiae
<220> FEATURE:
<221> NAME/KEY: VARIANT
<222> LOCATION: 16
<223> OTHER INFORMATION: Xaa = Modified Cysteine

<400> SEQUENCE: 202

Phe Gly Asp Phe Gly Gly Gln Tyr Val Pro Glu Ala Leu His Ala Xaa
1               5                   10                  15
Leu Arg

<210> SEQ ID NO 203
<211> LENGTH: 29
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 203

Leu Pro Asp Ala Val Val Ala Xaa Val Gly Gly Ser Asn Ser Thr
1               5                   10                  15
Gly Met Phe Ser Pro Phe Glu His Asp Thr Ser Val Lys
            20                  25

<210> SEQ ID NO 204
<211> LENGTH: 13
<212> TYPE: PRT
<213> ORGANISM: Saccharomyces cerevisiae
<220> FEATURE:
<221> NAME/KEY: VARIANT
<222> LOCATION: 5
<223> OTHER INFORMATION: Xaa = Modified Cysteine

<400> SEQUENCE: 204

Leu Thr Glu His Xaa Gln Gly Ala Gln Ile Trp Leu Lys
1               5                   10

<210> SEQ ID NO 205
<211> LENGTH: 21
<212> TYPE: PRT
<213> ORGANISM: Saccharomyces cerevisiae

```
<220> FEATURE:
<221> NAME/KEY: VARIANT
<222> LOCATION: 5
<223> OTHER INFORMATION: Xaa = Modified Cysteine

<400> SEQUENCE: 205

Ile Asn Leu Pro Xaa Val Asn Pro Thr Thr Gly Glu Val Gln Thr Asp
 1               5                  10                  15

Phe His Thr Leu Arg
            20

<210> SEQ ID NO 206
<211> LENGTH: 24
<212> TYPE: PRT
<213> ORGANISM: Saccharomyces cerevisiae
<220> FEATURE:
<221> NAME/KEY: VARIANT
<222> LOCATION: 7
<223> OTHER INFORMATION: Xaa = Modified Cysteine

<400> SEQUENCE: 206

Ser Thr Ala Met Val Leu Xaa Gly Ser Asn Asp Asp Lys Val Glu Phe
 1               5                  10                  15

Val Glu Pro Pro Lys Asp Ser Lys
            20

<210> SEQ ID NO 207
<211> LENGTH: 13
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 207

Ser Xaa Gly Val Asp Ala Met Ser Val Asp Asp Leu Lys
 1               5                  10

<210> SEQ ID NO 208
<211> LENGTH: 14
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 208

Ser Xaa Gly Val Asp Ala Met Ser Val Asp Asp Leu Lys Lys
 1               5                  10

<210> SEQ ID NO 209
<211> LENGTH: 25
<212> TYPE: PRT
<213> ORGANISM: Saccharomyces cerevisiae
<220> FEATURE:
<221> NAME/KEY: VARIANT
<222> LOCATION: 24
<223> OTHER INFORMATION: Xaa = Modified Cysteine

<400> SEQUENCE: 209

Asp Glu Ile Val Leu Ser Gly Asn Ser Val Glu Asp Val Ser Gln Asn
 1               5                  10                  15

Ala Ala Asp Leu Gln Gln Ile Xaa Arg
            20                  25
```

```
<210> SEQ ID NO 210
<211> LENGTH: 27
<212> TYPE: PRT
<213> ORGANISM: Saccharomyces cerevisiae
<220> FEATURE:
<221> NAME/KEY: VARIANT
<222> LOCATION: 26
<223> OTHER INFORMATION: Xaa = Modified Cysteine

<400> SEQUENCE: 210

Val Lys Asp Glu Ile Val Leu Ser Gly Asn Ser Val Glu Asp Val Ser
 1               5                  10                  15

Gln Asn Ala Ala Asp Leu Gln Gln Ile Xaa Arg
            20                  25

<210> SEQ ID NO 211
<211> LENGTH: 12
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 211

Xaa Pro Asp Ala Ser Val Ala Gly Leu Met Val Lys
 1               5                  10

<210> SEQ ID NO 212
<211> LENGTH: 12
<212> TYPE: PRT
<213> ORGANISM: Saccharomyces cerevisiae
<220> FEATURE:
<221> NAME/KEY: VARIANT
<222> LOCATION: 9
<223> OTHER INFORMATION: Xaa = Modified Cysteine

<400> SEQUENCE: 212

Asp Ser Ile Gly Gly Val Val Thr Xaa Val Val Arg
 1               5                  10

<210> SEQ ID NO 213
<211> LENGTH: 17
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 213

Asp Xaa Ile Val Asp Thr Ala Ala Gln Met Leu Glu Val Gln Asn Glu
 1               5                  10                  15

Ala

<210> SEQ ID NO 214
<211> LENGTH: 32
<212> TYPE: PRT
<213> ORGANISM: Saccharomyces cerevisiae
<220> FEATURE:
<221> NAME/KEY: VARIANT
<222> LOCATION: 30
<223> OTHER INFORMATION: Xaa = Modified Cysteine

<400> SEQUENCE: 214

Asp Tyr Phe Pro Trp Asp Asn Leu Ser Val Asp Ser Pro Lys Pro Pro
 1               5                  10                  15
```

```
Phe Pro Gln Gly Ile Gly Ala Pro Ile Asp Glu Gln Asn Xaa Ile Lys
            20                  25                  30
```

<210> SEQ ID NO 215
<211> LENGTH: 10
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 215

```
Xaa Val His Phe Gln Asn Ser Tyr Tyr Arg
 1               5                  10
```

<210> SEQ ID NO 216
<211> LENGTH: 13
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 216

```
Tyr Ser Ala Ala Asp Val Ala Xaa Trp Gly Ala Leu Arg
 1               5                  10
```

<210> SEQ ID NO 217
<211> LENGTH: 17
<212> TYPE: PRT
<213> ORGANISM: Saccharomyces cerevisiae
<220> FEATURE:
<221> NAME/KEY: VARIANT
<222> LOCATION: 11
<223> OTHER INFORMATION: Xaa = Modified Cysteine

<400> SEQUENCE: 217

```
Ile Val Ser Asn Ala Ser Cys Thr Thr Asn Xaa Leu Ala Pro Leu Ala
 1               5                  10                  15

Lys
```

<210> SEQ ID NO 218
<211> LENGTH: 12
<212> TYPE: PRT
<213> ORGANISM: Saccharomyces cerevisiae
<220> FEATURE:
<221> NAME/KEY: VARIANT
<222> LOCATION: 9
<223> OTHER INFORMATION: Xaa = Modified Cysteine

<400> SEQUENCE: 218

```
Asn Gly His Pro Phe Phe Leu Pro Xaa Thr Pro Lys
 1               5                  10
```

<210> SEQ ID NO 219
<211> LENGTH: 19
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine

<400> SEQUENCE: 219

```
Ser Pro Val Thr Val Glu Asp Val Gly Xaa Thr Gly Ala Leu Thr Ala
```

-continued

```
              1               5                  10                 15
Leu Leu Arg

<210> SEQ ID NO 220
<211> LENGTH: 17
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 220

Xaa Asn Pro Asn Arg Pro Ile Tyr Trp Ile Gln Ser Ser Tyr Asp Glu
  1               5                  10                 15

Lys

<210> SEQ ID NO 221
<211> LENGTH: 30
<212> TYPE: PRT
<213> ORGANISM: Saccharomyces cerevisiae
<220> FEATURE:
<221> NAME/KEY: VARIANT
<222> LOCATION: 17
<223> OTHER INFORMATION: Xaa = Modified Cysteine

<400> SEQUENCE: 221

Gln Ala Ala Gly Asn Leu Ile Ser Gln Gly Ile Asp Ala Leu Val Val
  1               5                  10                 15

Xaa Gly Gly Asp Gly Ser Leu Thr Gly Ala Asp Leu Phe Arg
            20                  25                  30

<210> SEQ ID NO 222
<211> LENGTH: 12
<212> TYPE: PRT
<213> ORGANISM: Saccharomyces cerevisiae
<220> FEATURE:
<221> NAME/KEY: VARIANT
<222> LOCATION: 5
<223> OTHER INFORMATION: Xaa = Modified Cysteine

<400> SEQUENCE: 222

Ile Gly Leu Asp Xaa Ala Ser Ser Glu Phe Phe Lys
  1               5                  10

<210> SEQ ID NO 223
<211> LENGTH: 16
<212> TYPE: PRT
<213> ORGANISM: Saccharomyces cerevisiae
<220> FEATURE:
<221> NAME/KEY: VARIANT
<222> LOCATION: 6
<223> OTHER INFORMATION: Xaa = Modified Cysteine

<400> SEQUENCE: 223

Ala Gln Tyr Asp Ser Xaa Asp Phe Val Ala Asp Val Pro Pro Pro Lys
  1               5                  10                 15

<210> SEQ ID NO 224
<211> LENGTH: 15
<212> TYPE: PRT
<213> ORGANISM: Saccharomyces cerevisiae
<220> FEATURE:
<221> NAME/KEY: VARIANT
<222> LOCATION: 4
<223> OTHER INFORMATION: Xaa = Modified Cysteine
```

```
<400> SEQUENCE: 224

Tyr Gly Thr Xaa Pro His Gly Gly Tyr Gly Ile Gly Thr Glu Arg
  1               5                  10                  15

<210> SEQ ID NO 225
<211> LENGTH: 16
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 225

Xaa Ile Ala Ile Ile Pro Gln Phe Glu Leu Ser Thr Ala Asp Ser Arg
  1               5                  10                  15

<210> SEQ ID NO 226
<211> LENGTH: 27
<212> TYPE: PRT
<213> ORGANISM: Saccharomyces cerevisiae
<220> FEATURE:
<221> NAME/KEY: VARIANT
<222> LOCATION: 24
<223> OTHER INFORMATION: Xaa = Modified Cysteine

<400> SEQUENCE: 226

Ile Thr Val Asp Glu Ala Leu Glu His Pro Tyr Leu Ser Ile Trp His
  1               5                  10                  15

Asp Pro Ala Asp Glu Pro Val Xaa Ser Glu Lys
             20                  25

<210> SEQ ID NO 227
<211> LENGTH: 13
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 227

Xaa Ala Asn Gly Ala Pro Ala Val Glu Val Asp Gly Lys
  1               5                  10

<210> SEQ ID NO 228
<211> LENGTH: 24
<212> TYPE: PRT
<213> ORGANISM: Saccharomyces cerevisiae
<220> FEATURE:
<221> NAME/KEY: VARIANT
<222> LOCATION: 19
<223> OTHER INFORMATION: Xaa = Modified Cysteine

<400> SEQUENCE: 228

Glu Ile Gly Trp Asn Asn Glu Asp Ile His Val Pro Leu Leu Pro Gly
  1               5                  10                  15

Glu Gln Xaa Gly Ala Leu Thr Lys
             20

<210> SEQ ID NO 229
<211> LENGTH: 13
<212> TYPE: PRT
<213> ORGANISM: Saccharomyces cerevisiae
<220> FEATURE:
<221> NAME/KEY: VARIANT
<222> LOCATION: 2
```

-continued

<223> OTHER INFORMATION: Xaa = Modified Cysteine

<400> SEQUENCE: 229

Ile Xaa Leu Pro Thr Phe Glu Ser Glu Glu Leu Ile Lys
1               5                   10

<210> SEQ ID NO 230
<211> LENGTH: 17
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 230

Leu Gly Ala Asn Tyr Ala Pro Xaa Ile Leu Pro Gln Leu Gln Ala Ala
1               5                   10                  15

Lys

<210> SEQ ID NO 231
<211> LENGTH: 21
<212> TYPE: PRT
<213> ORGANISM: Saccharomyces cerevisiae
<220> FEATURE:
<221> NAME/KEY: VARIANT
<222> LOCATION: 11
<223> OTHER INFORMATION: Xaa = Modified Cysteine

<400> SEQUENCE: 231

Leu Gly Gly Ile Gly Phe Ile His His Asn Xaa Thr Pro Glu Asp Gln
1               5                   10                  15

Ala Asp Met Val Arg
            20

<210> SEQ ID NO 232
<211> LENGTH: 15
<212> TYPE: PRT
<213> ORGANISM: Saccharomyces cerevisiae
<220> FEATURE:
<221> NAME/KEY: VARIANT
<222> LOCATION: 14
<223> OTHER INFORMATION: Xaa = Modified Cysteine

<400> SEQUENCE: 232

Leu Leu Ala Pro Gln Asp Ile Pro Val Leu Val Val Gly Xaa Arg
1               5                   10                  15

<210> SEQ ID NO 233
<211> LENGTH: 11
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 233

Val Ala Leu Asn Ser Ser Glu Xaa Leu Asn Lys
1               5                   10

<210> SEQ ID NO 234
<211> LENGTH: 17
<212> TYPE: PRT
<213> ORGANISM: Saccharomyces cerevisiae
<220> FEATURE:
<221> NAME/KEY: VARIANT -continued

```
<222> LOCATION: 3
<223> OTHER INFORMATION: Xaa = Modified Cysteine

<400> SEQUENCE: 234
```

Glu Gln Xaa Gln Gly Ala Leu Phe Gly Ala Val Gln Ser Pro Thr Thr
1               5                   10                  15

Lys

```
<210> SEQ ID NO 235
<211> LENGTH: 16
<212> TYPE: PRT
<213> ORGANISM: Saccharomyces cerevisiae
<220> FEATURE:
<221> NAME/KEY: VARIANT
<222> LOCATION: 15
<223> OTHER INFORMATION: Xaa = Modified Cysteine

<400> SEQUENCE: 235
```

Ser Ile Val Thr Asn Gly Ser Asn Thr Val Ser Gly Ala Asn Xaa Arg
1               5                   10                  15

```
<210> SEQ ID NO 236
<211> LENGTH: 21
<212> TYPE: PRT
<213> ORGANISM: Saccharomyces cerevisiae
<220> FEATURE:
<221> NAME/KEY: VARIANT
<222> LOCATION: 16
<223> OTHER INFORMATION: Xaa = Modified Cysteine

<400> SEQUENCE: 236
```

Gly Gly Pro Phe Asp Glu Ile Pro Gln Ala Asp Ile Phe Ile Asn Xaa
1               5                   10                  15

Ile Tyr Leu Ser Lys
            20

```
<210> SEQ ID NO 237
<211> LENGTH: 22
<212> TYPE: PRT
<213> ORGANISM: Saccharomyces cerevisiae
<220> FEATURE:
<221> NAME/KEY: VARIANT
<222> LOCATION: 14
<223> OTHER INFORMATION: Xaa = Modified Cysteine

<400> SEQUENCE: 237
```

Tyr Arg Asn Val Ile Ala His Thr Leu Asp Glu Asn Glu Xaa Ala Pro
1               5                   10                  15

Val Pro Pro Ala Val Arg
            20

```
<210> SEQ ID NO 238
<211> LENGTH: 13
<212> TYPE: PRT
<213> ORGANISM: Saccharomyces cerevisiae
<220> FEATURE:
<221> NAME/KEY: VARIANT
<222> LOCATION: 6
<223> OTHER INFORMATION: Xaa = Modified Cysteine

<400> SEQUENCE: 238
```

Gly His Asn Ile Pro Xaa Thr Ser Thr Ile Ser Gly Arg
1               5                   10

```
<210> SEQ ID NO 239
<211> LENGTH: 18
```

-continued

```
<212> TYPE: PRT
<213> ORGANISM: Saccharomyces cerevisiae
<220> FEATURE:
<221> NAME/KEY: VARIANT
<222> LOCATION: 4
<223> OTHER INFORMATION: Xaa = Modified Cysteine

<400> SEQUENCE: 239

Val His Ala Xaa Ile Gly Gly Thr Ser Phe Val Glu Asp Ala Glu Gly
1               5                   10                  15

Leu Arg

<210> SEQ ID NO 240
<211> LENGTH: 21
<212> TYPE: PRT
<213> ORGANISM: Saccharomyces cerevisiae
<220> FEATURE:
<221> NAME/KEY: VARIANT
<222> LOCATION: 19
<223> OTHER INFORMATION: Xaa = Modified Cysteine

<400> SEQUENCE: 240

Asp Leu Pro Ser Ser Ile Ala Thr Asn Gln Glu Val Phe Asp Phe Leu
1               5                   10                  15

Glu Ser Xaa Ala Lys
            20

<210> SEQ ID NO 241
<211> LENGTH: 27
<212> TYPE: PRT
<213> ORGANISM: Saccharomyces cerevisiae
<220> FEATURE:
<221> NAME/KEY: VARIANT
<222> LOCATION: 25
<223> OTHER INFORMATION: Xaa = Modified Cysteine

<400> SEQUENCE: 241

Glu Ile Ile Ala Asp Ser Phe Glu Thr Ile Met Met Ala Gln His Tyr
1               5                   10                  15

Asp Ala Asn Ile Ala Ile Pro Ser Xaa Asp Lys
            20                  25

<210> SEQ ID NO 242
<211> LENGTH: 13
<212> TYPE: PRT
<213> ORGANISM: Saccharomyces cerevisiae
<220> FEATURE:
<221> NAME/KEY: VARIANT
<222> LOCATION: 9
<223> OTHER INFORMATION: Xaa = Modified Cysteine

<400> SEQUENCE: 242

Leu Val Ser Asn Ala Ser Asn Gly Xaa Val Leu Asp Ala
1               5                   10

<210> SEQ ID NO 243
<211> LENGTH: 22
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 243

His Leu Gly Val Ile Gly Glu Xaa Asn Val Gln Tyr Ala Leu Gln Pro
1               5                   10                  15
```

-continued

```
Asp Gly Leu Asp Tyr Arg
            20

<210> SEQ ID NO 244
<211> LENGTH: 17
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 244

Ile Xaa Leu Pro Thr Phe Asp Pro Glu Glu Leu Ile Thr Leu Ile Gly
1               5                   10                  15

Lys

<210> SEQ ID NO 245
<211> LENGTH: 18
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 245

Leu Gly Ala Asn Tyr Ala Pro Xaa Val Leu Pro Gln Leu Gln Ala Ala
1               5                   10                  15

Ser Arg

<210> SEQ ID NO 246
<211> LENGTH: 9
<212> TYPE: PRT
<213> ORGANISM: Saccharomyces cerevisiae
<220> FEATURE:
<221> NAME/KEY: VARIANT
<222> LOCATION: 7
<223> OTHER INFORMATION: Xaa = Modified Cysteine

<400> SEQUENCE: 246

Trp Ala Ala Ala Ala Val Xaa Glu Lys
1               5

<210> SEQ ID NO 247
<211> LENGTH: 18
<212> TYPE: PRT
<213> ORGANISM: Saccharomyces cerevisiae
<220> FEATURE:
<221> NAME/KEY: VARIANT
<222> LOCATION: 16
<223> OTHER INFORMATION: Xaa = Modified Cysteine

<400> SEQUENCE: 247

Met Leu Asp Leu Ser Glu Glu Thr Asp Glu Glu Asn Ile Ser Thr Xaa
1               5                   10                  15

Val Lys

<210> SEQ ID NO 248
<211> LENGTH: 19
<212> TYPE: PRT
<213> ORGANISM: Saccharomyces cerevisiae
<220> FEATURE:
<221> NAME/KEY: VARIANT
<222> LOCATION: 17
<223> OTHER INFORMATION: Xaa = Modified Cysteine
```

-continued

```
<400> SEQUENCE: 248

Ser Ile Ala Pro Ala Tyr Gly Ile Pro Val Val Leu His Ser Asp His
1               5                   10                  15

Xaa Ala Lys

<210> SEQ ID NO 249
<211> LENGTH: 16
<212> TYPE: PRT
<213> ORGANISM: Saccharomyces cerevisiae
<220> FEATURE:
<221> NAME/KEY: VARIANT
<222> LOCATION: 7
<223> OTHER INFORMATION: Xaa = Modified Cysteine

<400> SEQUENCE: 249

Val Asn Leu Asp Thr Asp Xaa Gln Tyr Ala Tyr Leu Thr Gly Ile Arg
1               5                   10                  15

<210> SEQ ID NO 250
<211> LENGTH: 17
<212> TYPE: PRT
<213> ORGANISM: Saccharomyces cerevisiae
<220> FEATURE:
<221> NAME/KEY: VARIANT
<222> LOCATION: 4
<223> OTHER INFORMATION: Xaa = Modified Cysteine

<400> SEQUENCE: 250

Gly Tyr Thr Xaa Gln Phe Val Asp Met Val Leu Pro Asn Thr Ala Leu
1               5                   10                  15

Lys

<210> SEQ ID NO 251
<211> LENGTH: 14
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 251

Thr Xaa Ile Leu His Gly Pro Val Ala Ala Gln Phe Thr Lys
1               5                   10

<210> SEQ ID NO 252
<211> LENGTH: 21
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 252

Asp Ala Phe Glu His Leu Leu Xaa Gly Ala Ser Met Leu Gln Ile Gly
1               5                   10                  15

Thr Glu Leu Gln Lys
            20

<210> SEQ ID NO 253
<211> LENGTH: 33
<212> TYPE: PRT
<213> ORGANISM: Saccharomyces cerevisiae
<220> FEATURE:
```

```
<221> NAME/KEY: VARIANT
<222> LOCATION: 16
<223> OTHER INFORMATION: Xaa = Modified Cysteine

<400> SEQUENCE: 253

Ile Gln Asp Ser Glu Phe Asn Gly Ile Thr Glu Leu Asn Leu Ser Xaa
 1               5                  10                  15

Pro Asn Val Pro Gly Lys Pro Gln Val Ala Tyr Asp Phe Asp Leu Thr
            20                  25                  30

Lys

<210> SEQ ID NO 254
<211> LENGTH: 20
<212> TYPE: PRT
<213> ORGANISM: Saccharomyces cerevisiae
<220> FEATURE:
<221> NAME/KEY: VARIANT
<222> LOCATION: 13
<223> OTHER INFORMATION: Xaa = Modified Cysteine

<400> SEQUENCE: 254

Leu Pro Asp Ser Ala Leu Asp Leu Val Asp Ile Ser Xaa Ala Gly Val
 1               5                  10                  15

Ala Val Ala Arg
            20

<210> SEQ ID NO 255
<211> LENGTH: 15
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine

<400> SEQUENCE: 255

Leu Ser Thr Val Ser Pro Val Phe Val Xaa Gln Ser Phe Ala Lys
 1               5                  10                  15

<210> SEQ ID NO 256
<211> LENGTH: 12
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine

<400> SEQUENCE: 256

Asn Pro Val Ile Leu Ala Asp Ala Cys Xaa Ser Arg
 1               5                  10

<210> SEQ ID NO 257
<211> LENGTH: 8
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Oxidized Methionine
<220> FEATURE:
<221> NAME/KEY: VARIANT
<222> LOCATION: 5
<223> OTHER INFORMATION: Xaa = Modified Cysteine

<400> SEQUENCE: 257

Xaa Glu Ile Leu Xaa Gln Gln Arg
 1               5
```

```
<210> SEQ ID NO 258
<211> LENGTH: 9
<212> TYPE: PRT
<213> ORGANISM: Saccharomyces cerevisiae
<220> FEATURE:
<221> NAME/KEY: VARIANT
<222> LOCATION: 4
<223> OTHER INFORMATION: Xaa = Modified Cysteine

<400> SEQUENCE: 258

Met Leu Ser Xaa Ala Gly Ala Asp Arg
1               5

<210> SEQ ID NO 259
<211> LENGTH: 17
<212> TYPE: PRT
<213> ORGANISM: Saccharomyces cerevisiae
<220> FEATURE:
<221> NAME/KEY: VARIANT
<222> LOCATION: 16
<223> OTHER INFORMATION: Xaa = Modified Cysteine

<400> SEQUENCE: 259

Phe Gln Tyr Ile Ala Ile Ser Gln Ser Asp Ala Asp Ser Glu Ser Xaa
1               5                   10                  15

Lys

<210> SEQ ID NO 260
<211> LENGTH: 27
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 260

Thr Tyr Leu Pro Pro Val Ser Xaa Asp Ala Glu Asp Pro Leu Phe Leu
1               5                   10                  15

Leu Tyr Thr Ser Gly Ser Thr Gly Ser Pro Lys
            20                  25

<210> SEQ ID NO 261
<211> LENGTH: 17
<212> TYPE: PRT
<213> ORGANISM: Saccharomyces cerevisiae
<220> FEATURE:
<221> NAME/KEY: VARIANT
<222> LOCATION: 16
<223> OTHER INFORMATION: Xaa = Modified Cysteine

<400> SEQUENCE: 261

Ala Ile Ala Asn Gly Gln Val Asp Gly Phe Pro Thr Gln Glu Glu Xaa
1               5                   10                  15

Arg

<210> SEQ ID NO 262
<211> LENGTH: 27
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine
```

-continued

```
<400> SEQUENCE: 262

Phe Ile Pro Ser Leu Ile Gln Xaa Ile Ala Asp Pro Thr Glu Val Pro
1               5                   10                  15

Glu Thr Val His Leu Leu Gly Ala Thr Thr Phe
            20                  25

<210> SEQ ID NO 263
<211> LENGTH: 29
<212> TYPE: PRT
<213> ORGANISM: Saccharomyces cerevisiae
<220> FEATURE:
<221> NAME/KEY: VARIANT
<222> LOCATION: 23
<223> OTHER INFORMATION: Xaa = Modified Cysteine

<400> SEQUENCE: 263

Ile Ala Asn Gln Ser Asn Leu Ser Pro Ser Val Glu Pro Tyr Ile Val
1               5                   10                  15

Gln Leu Val Pro Ala Ile Xaa Thr Asn Ala Gly Asn Lys
            20                  25

<210> SEQ ID NO 264
<211> LENGTH: 21
<212> TYPE: PRT
<213> ORGANISM: Saccharomyces cerevisiae
<220> FEATURE:
<221> NAME/KEY: VARIANT
<222> LOCATION: 7
<223> OTHER INFORMATION: Xaa = Modified Cysteine

<400> SEQUENCE: 264

Lys Glu Ile Glu Glu His Xaa Ser Met Leu Gly Leu Asp Pro Glu Ile
1               5                   10                  15

Val Ser His Ser Arg
            20

<210> SEQ ID NO 265
<211> LENGTH: 18
<212> TYPE: PRT
<213> ORGANISM: Saccharomyces cerevisiae
<220> FEATURE:
<221> NAME/KEY: VARIANT
<222> LOCATION: 7
<223> OTHER INFORMATION: Xaa = Modified Cysteine

<400> SEQUENCE: 265

Asn Thr Tyr Glu Tyr Glu Xaa Ser Phe Leu Leu Gly Glu Asn Ile Gly
1               5                   10                  15

Met Lys

<210> SEQ ID NO 266
<211> LENGTH: 15
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine

<400> SEQUENCE: 266

Pro Gln Ile Thr Asp Ile Asn Phe Gln Xaa Ser Leu Ser Ser Arg
1               5                   10                  15

<210> SEQ ID NO 267
<211> LENGTH: 25
```

```
<212> TYPE: PRT
<213> ORGANISM: Saccharomyces cerevisiae
<220> FEATURE:
<221> NAME/KEY: VARIANT
<222> LOCATION: 24
<223> OTHER INFORMATION: Xaa = Modified Cysteine

<400> SEQUENCE: 267

Ser Thr Leu Ile Asn Val Leu Thr Gly Glu Leu Leu Pro Thr Ser Gly
 1               5                  10                  15

Glu Val Tyr Thr His Glu Asn Xaa Arg
             20                  25

<210> SEQ ID NO 268
<211> LENGTH: 28
<212> TYPE: PRT
<213> ORGANISM: Saccharomyces cerevisiae
<220> FEATURE:
<221> NAME/KEY: VARIANT
<222> LOCATION: 23
<223> OTHER INFORMATION: Xaa = Modified Cysteine

<400> SEQUENCE: 268

Val Thr Asn Met Glu Phe Gln Tyr Pro Gly Thr Ser Lys Pro Gln Ile
 1               5                  10                  15

Thr Asp Ile Asn Phe Gln Xaa Ser Leu Ser Ser Arg
             20                  25

<210> SEQ ID NO 269
<211> LENGTH: 12
<212> TYPE: PRT
<213> ORGANISM: Saccharomyces cerevisiae
<220> FEATURE:
<221> NAME/KEY: VARIANT
<222> LOCATION: 6, 9
<223> OTHER INFORMATION: Xaa = Modified Cysteine
<220> FEATURE:
<221> NAME/KEY: VARIANT
<222> LOCATION: 9
<223> OTHER INFORMATION: Xaa = Oxidized Methionine

<400> SEQUENCE: 269

Asn Val Ala Ala Gly Xaa Asn Pro Xaa Asp Leu Arg
 1               5                  10

<210> SEQ ID NO 270
<211> LENGTH: 12
<212> TYPE: PRT
<213> ORGANISM: Saccharomyces cerevisiae
<220> FEATURE:
<221> NAME/KEY: VARIANT
<222> LOCATION: 6
<223> OTHER INFORMATION: Xaa = Modified Cysteine

<400> SEQUENCE: 270

Asn Val Ala Ala Gly Xaa Asn Pro Met Asp Leu Arg
 1               5                  10

<210> SEQ ID NO 271
<211> LENGTH: 17
<212> TYPE: PRT
<213> ORGANISM: Saccharomyces cerevisiae
<220> FEATURE:
<221> NAME/KEY: VARIANT
<222> LOCATION: 7
<223> OTHER INFORMATION: Xaa = Modified Cysteine

<400> SEQUENCE: 271
```

-continued

```
Val Gly Leu Ile Gly Ser Xaa Thr Asn Ser Ser Tyr Glu Asp Met Ser
1               5                   10                  15

Arg

<210> SEQ ID NO 272
<211> LENGTH: 15
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine

<400> SEQUENCE: 272

Tyr Gly Met Asp Tyr Met Tyr Asp Ala Xaa Ser Thr Thr Ala Arg
1               5                   10                  15

<210> SEQ ID NO 273
<211> LENGTH: 18
<212> TYPE: PRT
<213> ORGANISM: Saccharomyces cerevisiae
<220> FEATURE:
<221> NAME/KEY: VARIANT
<222> LOCATION: 5
<223> OTHER INFORMATION: Xaa = Modified Cysteine

<400> SEQUENCE: 273

Val Val Glu Val Xaa Leu Ala Asp Leu Gln Gly Ser Glu Asp His Ser
1               5                   10                  15

Phe Arg

<210> SEQ ID NO 274
<211> LENGTH: 14
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 274

Asn Ile Thr Trp Ile Ala Glu Xaa Ile Ala Gln Asn Gln Arg
1               5                   10

<210> SEQ ID NO 275
<211> LENGTH: 27
<212> TYPE: PRT
<213> ORGANISM: Saccharomyces cerevisiae
<220> FEATURE:
<221> NAME/KEY: VARIANT
<222> LOCATION: 3
<223> OTHER INFORMATION: Xaa = Modified Cysteine

<400> SEQUENCE: 275

Glu Phe Xaa Ser Lys Met Asn Gln Val Cys Gly Thr Arg Gln Cys Pro
1               5                   10                  15

Ile Pro Lys Lys Pro Ile Ser Ala Leu Asp Lys
            20                  25

<210> SEQ ID NO 276
<211> LENGTH: 16
<212> TYPE: PRT
<213> ORGANISM: Saccharomyces cerevisiae
<220> FEATURE:
<221> NAME/KEY: VARIANT
<222> LOCATION: 9
<223> OTHER INFORMATION: Xaa = Modified Cysteine
```

-continued

```
<400> SEQUENCE: 276

Gly Asp Leu Val Leu Asp Val Gly Xaa Gly Val Gly Gly Pro Ala Arg
1               5                   10                  15

<210> SEQ ID NO 277
<211> LENGTH: 12
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 277

Val Tyr Ala Ile Glu Ala Thr Xaa His Ala Pro Lys
1               5                   10

<210> SEQ ID NO 278
<211> LENGTH: 34
<212> TYPE: PRT
<213> ORGANISM: Saccharomyces cerevisiae
<220> FEATURE:
<221> NAME/KEY: VARIANT
<222> LOCATION: 17
<223> OTHER INFORMATION: Xaa = Modified Cysteine

<400> SEQUENCE: 278

Leu Val Glu Ala Phe Gln Trp Thr Asp Lys Asn Gly Thr Val Leu Pro
1               5                   10                  15

Xaa Asn Trp Thr Pro Gly Ala Ala Thr Ile Lys Pro Thr Val Glu Asp
            20                  25                  30

Ser Lys

<210> SEQ ID NO 279
<211> LENGTH: 24
<212> TYPE: PRT
<213> ORGANISM: Saccharomyces cerevisiae
<220> FEATURE:
<221> NAME/KEY: VARIANT
<222> LOCATION: 7
<223> OTHER INFORMATION: Xaa = Modified Cysteine

<400> SEQUENCE: 279

Asn Gly Thr Val Leu Pro Xaa Asn Trp Thr Pro Gly Ala Ala Thr Ile
1               5                   10                  15

Lys Pro Thr Val Glu Asp Ser Lys
            20

<210> SEQ ID NO 280
<211> LENGTH: 21
<212> TYPE: PRT
<213> ORGANISM: Saccharomyces cerevisiae
<220> FEATURE:
<221> NAME/KEY: VARIANT
<222> LOCATION: 4
<223> OTHER INFORMATION: Xaa = Modified Cysteine

<400> SEQUENCE: 280

Ile Gly Ile Xaa Tyr Glu Pro Pro Thr Ala Thr Pro Asn Ser Gln Leu
1               5                   10                  15

Ala Thr Val Asp Arg
            20

<210> SEQ ID NO 281
```

```
<211> LENGTH: 18
<212> TYPE: PRT
<213> ORGANISM: Saccharomyces cerevisiae
<220> FEATURE:
<221> NAME/KEY: VARIANT
<222> LOCATION: 17
<223> OTHER INFORMATION: Xaa = Modified Cysteine

<400> SEQUENCE: 281

Val Gly Leu Phe Ser Tyr Gly Ser Gly Leu Ala Ala Ser Leu Tyr Ser
 1               5                  10                  15

Xaa Lys

<210> SEQ ID NO 282
<211> LENGTH: 16
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine

<400> SEQUENCE: 282

Ala Ala Gly His Leu Val Glu Thr Ser Xaa Thr Ile Met Asp Leu Lys
 1               5                  10                  15

<210> SEQ ID NO 283
<211> LENGTH: 16
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 283

Xaa Leu Ala Thr Leu Leu Gly His Asn Asp Trp Val Ser Gln Val Arg
 1               5                  10                  15

<210> SEQ ID NO 284
<211> LENGTH: 18
<212> TYPE: PRT
<213> ORGANISM: Saccharomyces cerevisiae
<220> FEATURE:
<221> NAME/KEY: VARIANT
<222> LOCATION: 3
<223> OTHER INFORMATION: Xaa = Modified Cysteine

<400> SEQUENCE: 284

Gly Gln Xaa Leu Ala Thr Leu Leu Gly His Asn Asp Trp Val Ser Gln
 1               5                  10                  15

Val Arg

<210> SEQ ID NO 285
<211> LENGTH: 11
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 285

Tyr Thr Gln Ser Asn Ser Val Xaa Tyr Ala Arg
 1               5                  10

<210> SEQ ID NO 286
```

```
<211> LENGTH: 17
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 286

Xaa Pro His Leu Glu Ile Val Asn Leu Ser Asp Asn Ala Phe Gly Leu
 1               5                  10                  15

Arg

<210> SEQ ID NO 287
<211> LENGTH: 11
<212> TYPE: PRT
<213> ORGANISM: Saccharomyces cerevisiae
<220> FEATURE:
<221> NAME/KEY: VARIANT
<222> LOCATION: 5
<223> OTHER INFORMATION: Xaa = Modified Cysteine

<400> SEQUENCE: 287

Val Glu Ala Ser Xaa Phe Asp Gly Asn Lys Arg
 1               5                  10

<210> SEQ ID NO 288
<211> LENGTH: 22
<212> TYPE: PRT
<213> ORGANISM: Saccharomyces cerevisiae
<220> FEATURE:
<221> NAME/KEY: VARIANT
<222> LOCATION: 20
<223> OTHER INFORMATION: Xaa = Modified Cysteine

<400> SEQUENCE: 288

Ile Ala Glu Ser Thr Pro Leu Pro Val Gly Val Ala Glu Asn Trp Leu
 1               5                  10                  15

Tyr Leu Pro Xaa Ile Lys
                20

<210> SEQ ID NO 289
<211> LENGTH: 17
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 289

Gly Xaa Gly Val Ala Ala Thr Glu Leu Gly Met Leu Ala Gly Ala Asp
 1               5                  10                  15

Arg

<210> SEQ ID NO 290
<211> LENGTH: 18
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine

<400> SEQUENCE: 290

Ile Gly Pro Gln Gly Ala Leu Leu Gly Xaa Asp Ala Ala Gly Gln Ile
 1               5                  10                  15
```

Val Lys

<210> SEQ ID NO 291
<211> LENGTH: 9
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 291

Gly Xaa Glu Val Val Val Ser Gly Lys
 1               5

<210> SEQ ID NO 292
<211> LENGTH: 17
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 292

Xaa Ala Gly Gly Asn Asn Ala Gly His Thr Ile Val Val Asp Gly Val
 1               5                  10                  15

Lys

<210> SEQ ID NO 293
<211> LENGTH: 10
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 293

Xaa Gly Trp Leu Asp Leu Val Val Leu Lys
 1               5                  10

<210> SEQ ID NO 294
<211> LENGTH: 13
<212> TYPE: PRT
<213> ORGANISM: Saccharomyces cerevisiae
<220> FEATURE:
<221> NAME/KEY: VARIANT
<222> LOCATION: 2
<223> OTHER INFORMATION: Xaa = Modified Cysteine

<400> SEQUENCE: 294

Val Xaa Glu Phe Met Ile Ser Gln Leu Gly Leu Gln Lys
 1               5                  10

<210> SEQ ID NO 295
<211> LENGTH: 14
<212> TYPE: PRT
<213> ORGANISM: Saccharomyces cerevisiae
<220> FEATURE:
<221> NAME/KEY: VARIANT
<222> LOCATION: 5
<223> OTHER INFORMATION: Xaa = Modified Cysteine

<400> SEQUENCE: 295

Ala Gly Gly Glu Xaa Ile Thr Leu Asp Gln Leu Ala Val Arg
 1               5                  10

```
<210> SEQ ID NO 296
<211> LENGTH: 17
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 296

Xaa Gly Gly Leu Pro Ala Pro Glu Asp Ser Asp Asn Pro Leu Gly Tyr
 1               5                  10                  15

Lys

<210> SEQ ID NO 297
<211> LENGTH: 10
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 297

Gly Asn Ala Leu Asp Thr Leu Xaa Ala Arg
 1               5                  10

<210> SEQ ID NO 298
<211> LENGTH: 20
<212> TYPE: PRT
<213> ORGANISM: Saccharomyces cerevisiae
<220> FEATURE:
<221> NAME/KEY: VARIANT
<222> LOCATION: 4
<223> OTHER INFORMATION: Xaa = Modified Cysteine

<400> SEQUENCE: 298

Leu Ser Tyr Xaa Gly Gly Leu Pro Ala Pro Glu Asp Ser Asp Asn Pro
 1               5                  10                  15

Leu Gly Tyr Lys
            20

<210> SEQ ID NO 299
<211> LENGTH: 22
<212> TYPE: PRT
<213> ORGANISM: Saccharomyces cerevisiae
<220> FEATURE:
<221> NAME/KEY: VARIANT
<222> LOCATION: 6
<223> OTHER INFORMATION: Xaa = Modified Cysteine

<400> SEQUENCE: 299

Ser Phe Leu Ser Tyr Xaa Gly Gly Leu Pro Ala Pro Glu Asp Ser Asp
 1               5                  10                  15

Asn Pro Leu Gly Tyr Lys
            20

<210> SEQ ID NO 300
<211> LENGTH: 32
<212> TYPE: PRT
<213> ORGANISM: Saccharomyces cerevisiae
<220> FEATURE:
<221> NAME/KEY: VARIANT
<222> LOCATION: 25
<223> OTHER INFORMATION: Xaa = Modified Cysteine
```

-continued

```
<400> SEQUENCE: 300

Ala Thr Ala Asp Ala Val Gln Ala His Ile Pro Gln Gly Thr Asp
 1               5                  10                  15

Leu Ala Gln Val Ala Pro Ile Leu Xaa Ala Gly Ile Thr Val Tyr Lys
             20                  25                  30

<210> SEQ ID NO 301
<211> LENGTH: 21
<212> TYPE: PRT
<213> ORGANISM: Saccharomyces cerevisiae
<220> FEATURE:
<221> NAME/KEY: VARIANT
<222> LOCATION: 12
<223> OTHER INFORMATION: Xaa = Modified Cysteine

<400> SEQUENCE: 301

Val Asp Met Pro Val Ile Phe Gly Leu Leu Thr Xaa Met Thr Glu Glu
 1               5                  10                  15

Gln Ala Leu Ala Arg
             20

<210> SEQ ID NO 302
<211> LENGTH: 25
<212> TYPE: PRT
<213> ORGANISM: Saccharomyces cerevisiae
<220> FEATURE:
<221> NAME/KEY: VARIANT
<222> LOCATION: 16
<223> OTHER INFORMATION: Xaa = Modified Cysteine

<400> SEQUENCE: 302

Glu Ile Ser Glu Asp Gly Ala Asp Ser Leu Asn Val Ala Met Asp Xaa
 1               5                  10                  15

Ile Ser Glu Ala Phe Gly Phe Glu Arg
             20                  25

<210> SEQ ID NO 303
<211> LENGTH: 10
<212> TYPE: PRT
<213> ORGANISM: Saccharomyces cerevisiae
<220> FEATURE:
<221> NAME/KEY: VARIANT
<222> LOCATION: 8
<223> OTHER INFORMATION: Xaa = Modified Cysteine

<400> SEQUENCE: 303

His Asp Ala Glu Gly Val Val Xaa Val Arg
 1               5                  10

<210> SEQ ID NO 304
<211> LENGTH: 27
<212> TYPE: PRT
<213> ORGANISM: Saccharomyces cerevisiae
<220> FEATURE:
<221> NAME/KEY: VARIANT
<222> LOCATION: 22
<223> OTHER INFORMATION: Xaa = Modified Cysteine

<400> SEQUENCE: 304

Glu Leu Leu Asn Glu Tyr Gly Phe Asp Gly Asp Asn Ala Pro Ile Ile
 1               5                  10                  15

Met Gly Ser Ala Leu Xaa Ala Leu Glu Gly Arg
             20                  25

<210> SEQ ID NO 305
```

```
<211> LENGTH: 12
<212> TYPE: PRT
<213> ORGANISM: Saccharomyces cerevisiae
<220> FEATURE:
<221> NAME/KEY: VARIANT
<222> LOCATION: 5
<223> OTHER INFORMATION: Xaa = Modified Cysteine

<400> SEQUENCE: 305

Asp Leu Met Ala Xaa Ala Gln Thr Gly Ser Gly Lys
 1               5                  10

<210> SEQ ID NO 306
<211> LENGTH: 17
<212> TYPE: PRT
<213> ORGANISM: Saccharomyces cerevisiae
<220> FEATURE:
<221> NAME/KEY: VARIANT
<222> LOCATION: 10
<223> OTHER INFORMATION: Xaa = Modified Cysteine

<400> SEQUENCE: 306

Phe Phe Asn Asn His Leu Phe Ala Ser Xaa Ser Asp Asp Asn Ile Leu
 1               5                  10                  15

Arg

<210> SEQ ID NO 307
<211> LENGTH: 15
<212> TYPE: PRT
<213> ORGANISM: Saccharomyces cerevisiae
<220> FEATURE:
<221> NAME/KEY: VARIANT
<222> LOCATION: 1
<223> OTHER INFORMATION: Xaa = Modified Cysteine

<400> SEQUENCE: 307

Xaa Val Gly Val Ile Leu Gly Asp Ala Asn Ser Ser Thr Ile Arg
 1               5                  10                  15

<210> SEQ ID NO 308
<211> LENGTH: 20
<212> TYPE: PRT
<213> ORGANISM: Saccharomyces cerevisiae
<220> FEATURE:
<221> NAME/KEY: VARIANT
<222> LOCATION: 16
<223> OTHER INFORMATION: Xaa = Modified Cysteine

<400> SEQUENCE: 308

Val Asn Val Tyr Gly Gly Ala Val Ala Leu Gly His Pro Leu Gly Xaa
 1               5                  10                  15

Ser Gly Ala Arg
            20

<210> SEQ ID NO 309
<211> LENGTH: 14
<212> TYPE: PRT
<213> ORGANISM: Saccharomyces cerevisiae
<220> FEATURE:
<221> NAME/KEY: VARIANT
<222> LOCATION: 11
<223> OTHER INFORMATION: Xaa = Modified Cysteine

<400> SEQUENCE: 309

Ile Ala Pro Ala Leu Ala Met Gly Asn Val Xaa Ile Leu Lys
 1               5                  10
```

```
<210> SEQ ID NO 310
<211> LENGTH: 17
<212> TYPE: PRT
<213> ORGANISM: Saccharomyces cerevisiae
<220> FEATURE:
<221> NAME/KEY: VARIANT
<222> LOCATION: 16
<223> OTHER INFORMATION: Xaa = Modified Cysteine

<400> SEQUENCE: 310

Pro Ala Ala Val Thr Pro Leu Asn Ala Leu Tyr Phe Ala Ser Leu Xaa
 1               5                  10                  15

Lys

<210> SEQ ID NO 311
<211> LENGTH: 24
<212> TYPE: PRT
<213> ORGANISM: Saccharomyces cerevisiae
<220> FEATURE:
<221> NAME/KEY: VARIANT
<222> LOCATION: 3
<223> OTHER INFORMATION: Xaa = Modified Cysteine

<400> SEQUENCE: 311

Ile Ile Xaa Glu Asn Tyr Leu Phe Asn Trp Trp Glu Gln Leu Asp Asp
 1               5                  10                  15

Leu Ser Glu Val Glu Asn Asp Arg
            20
```